(12) United States Patent
Zdeblick

(10) Patent No.: US 9,084,566 B2
(45) Date of Patent: Jul. 21, 2015

(54) SMART PARENTERAL ADMINISTRATION SYSTEM

(75) Inventor: Mark Zdeblick, Portola Valley, CA (US)

(73) Assignee: Proteus Digital Health, Inc., Redwood City, CA (US)

( * ) Notice: Subject to any disclaimer, the term of this patent is extended or adjusted under 35 U.S.C. 154(b) by 1208 days.

(21) Appl. No.: 12/349,453

(22) Filed: Jan. 6, 2009

(65) Prior Publication Data

US 2009/0118594 A1 May 7, 2009

Related U.S. Application Data

(63) Continuation of application No. PCT/US2007/015547, filed on Jul. 6, 2007.

(60) Provisional application No. 60/819,750, filed on Jul. 7, 2006, provisional application No. 60/891,883, filed on Feb. 27, 2007, provisional application No. 60/940,631, filed on May 29, 2007, provisional application No. 60/946,706, filed on Jun. 27, 2007.

(51) Int. Cl.
*A61B 5/117* (2006.01)
*A61M 16/00* (2006.01)
(Continued)

(52) U.S. Cl.
CPC ............... *A61B 5/117* (2013.01); *A61B 5/411* (2013.01); *A61M 5/14* (2013.01); *A61M 15/0068* (2014.02);
(Continued)

(58) Field of Classification Search
CPC ... A61M 5/172; A61M 5/168; A61M 5/1723; A61M 15/00; A61M 15/0086; A61M 15/0088; A61M 15/002; A61M 15/0021; A61M 15/008; A61M 15/009; A61M 15/0005; A61M 16/00; A61M 16/0057; A61M 16/06; A61M 16/0633; A61M 16/0051; A61M 16/0666; A61M 16/0677; A61M 11/00; A61M 16/161; A61M 15/0068; A61M 15/0065; A61M 5/14; G06F 19/3468; G06F 19/3481; G06F 19/3406; G06F 19/00; G06F 21/00; G06F 19/3418; G06F 19/3462; G06F 21/31; G06F 21/6245; A61N 1/30; A61N 1/32; A61N 1/044; A61N 1/325; A61N 1/303; F04D 29/052; F04D 25/166; A61B 5/0408; A61B 5/08; A61B 5/087; A61B 5/04085; A61B 5/0878; A61B 5/6803; A61B 5/0205; A61B 5/7264; A61B 5/0836; A61B 5/00; A61B 5/0002; A61B 5/4839; A61B 5/117; A61B 5/411; G06Q 50/22; A62B 7/00; A62B 9/00; A61G 10/00; H04B 13/005; F16K 31/02
USPC ............. 128/200.11–200.24, 203.12, 203.15, 128/204.18, 204.21, 204.23, 205.23, 898; 604/501, 220, 66, 503; 600/544
See application file for complete search history.

(56) References Cited

U.S. PATENT DOCUMENTS

| | | |
|---|---|---|
| 3,812,854 A | 5/1974 | Michaels et al. |
| 3,880,146 A | 4/1975 | Everett et al. |

(Continued)

FOREIGN PATENT DOCUMENTS

| | | |
|---|---|---|
| EP | 0329306 | 8/1989 |
| EP | 2248461 | 11/2010 |

(Continued)

OTHER PUBLICATIONS

Aade, "AADE 37th Annual Meeting San Antonio Aug. 4-7, 2010" American Association of Diabetes Educators (2010); http://www.diabeteseducator.org/annualmeeting/2010/index.html; 2 pp.

(Continued)

*Primary Examiner* — Annette Dixon
(74) *Attorney, Agent, or Firm* — K&L Gates LLP

(57) ABSTRACT

The invention provides methods and systems for evaluating a fluid transfer event between a parenteral fluid delivery and a patient. The evaluation of the fluid transfer event can be prospective real-time and/or historic, as desired, and take a variety of different formats.

10 Claims, 42 Drawing Sheets

(51) Int. Cl.
*A61B 5/00* (2006.01)
*A61M 5/14* (2006.01)
*H04B 13/00* (2006.01)
*A61M 1/16* (2006.01)
*A61M 1/28* (2006.01)
*A61M 5/178* (2006.01)
*A61M 15/00* (2006.01)

(52) U.S. Cl.
CPC ............... *H04B 13/005* (2013.01); *A61M 1/16* (2013.01); *A61M 1/28* (2013.01); *A61M 5/1782* (2013.01); *A61M 15/00* (2013.01); *A61M 2016/0021* (2013.01); *A61M 2016/0027* (2013.01); *A61M 2205/13* (2013.01); *A61M 2205/3523* (2013.01); *A61M 2205/3538* (2013.01); *A61M 2205/3553* (2013.01); *A61M 2205/3561* (2013.01); *A61M 2205/3592* (2013.01); *A61M 2205/52* (2013.01); *A61M 2205/581* (2013.01); *A61M 2205/583* (2013.01); *A61M 2205/6018* (2013.01); *A61M 2205/6081* (2013.01); *A61M 2230/06* (2013.01); *A61M 2230/30* (2013.01); *A61M 2230/42* (2013.01); *A61M 2230/50* (2013.01); *A61M 2230/63* (2013.01)

(56) References Cited

U.S. PATENT DOCUMENTS

| | | | |
|---|---|---|---|
| 4,403,989 | A | 9/1983 | Christensen et al. |
| 4,475,905 | A | 10/1984 | Himmelstrup |
| 4,487,602 | A | 12/1984 | Christensen et al. |
| 4,529,401 | A | 7/1985 | Leslie et al. |
| 4,533,346 | A * | 8/1985 | Cosgrove et al. ............... 604/66 |
| 4,551,133 | A | 11/1985 | Zegers de Beyl et al. |
| 4,621,644 | A | 11/1986 | Ellers |
| 4,669,479 | A | 6/1987 | Dunseath, Jr. |
| 4,705,503 | A | 11/1987 | Dorman et al. |
| 4,795,429 | A | 1/1989 | Feldstein |
| 4,850,967 | A | 7/1989 | Cosmai |
| 4,911,916 | A | 3/1990 | Cleary |
| 4,922,901 | A | 5/1990 | Brooks et al. |
| 5,006,342 | A | 4/1991 | Cleary et al. |
| 5,125,888 | A | 6/1992 | Howard et al. |
| 5,135,479 | A | 8/1992 | Sibalis et al. |
| 5,156,911 | A | 10/1992 | Stewart |
| 5,167,649 | A | 12/1992 | Zook |
| 5,190,522 | A | 3/1993 | Wojcicki et al. |
| 5,205,292 | A | 4/1993 | Czar et al. |
| 5,213,568 | A | 5/1993 | Lattin et al. |
| 5,224,927 | A * | 7/1993 | Tapper ............... 604/20 |
| 5,246,418 | A | 9/1993 | Haynes et al. |
| 5,284,133 | A | 2/1994 | Burns et al. |
| 5,289,824 | A | 3/1994 | Mills et al. |
| 5,300,299 | A | 4/1994 | Sweet et al. |
| 5,317,506 | A | 5/1994 | Coutre et al. |
| 5,331,953 | A | 7/1994 | Andersson et al. |
| 5,351,695 | A | 10/1994 | Mills et al. |
| 5,363,842 | A | 11/1994 | Mishelevich et al. |
| 5,364,838 | A | 11/1994 | Rubsamen |
| 5,394,866 | A | 3/1995 | Ritson et al. |
| 5,404,871 | A | 4/1995 | Goodman et al. |
| 5,415,866 | A | 5/1995 | Zook |
| 5,423,750 | A | 6/1995 | Spiller |
| 5,479,920 | A | 1/1996 | Piper et al. |
| 5,487,378 | A | 1/1996 | Robertson et al. |
| 5,505,195 | A | 4/1996 | Wolf |
| 5,505,958 | A | 4/1996 | Bello et al. |
| 5,507,277 | A | 4/1996 | Rubsamen et al. |
| 5,509,404 | A | 4/1996 | Lloyd et al. |
| 5,522,378 | A | 6/1996 | Ritson et al. |
| 5,527,288 | A | 6/1996 | Gross et al. |
| 5,536,503 | A | 7/1996 | Kitchell et al. |
| 5,540,669 | A | 7/1996 | Sage, Jr. et al. |
| 5,542,410 | A | 8/1996 | Goodman et al. |
| 5,556,421 | A | 9/1996 | Prutchi et al. |
| 5,570,682 | A | 11/1996 | Johnson |
| 5,586,550 | A | 12/1996 | Ivri et al. |
| 5,587,237 | A | 12/1996 | Korpman |
| 5,593,390 | A | 1/1997 | Castellano et al. |
| RE35,474 | E | 3/1997 | Woodard et al. |
| 5,608,647 | A | 3/1997 | Rubsamen et al. |
| 5,616,124 | A | 4/1997 | Hague et al. |
| 5,622,162 | A | 4/1997 | Johansson et al. |
| 5,622,180 | A | 4/1997 | Tammi et al. |
| 5,634,899 | A | 6/1997 | Shapland et al. |
| 5,645,855 | A | 7/1997 | Lorenz |
| 5,655,516 | A | 8/1997 | Goodman et al. |
| 5,655,523 | A | 8/1997 | Hodson et al. |
| 5,656,286 | A | 8/1997 | Miranda et al. |
| 5,666,945 | A | 9/1997 | Davenport |
| 5,676,129 | A | 10/1997 | Rocci, Jr. et al. |
| 5,686,099 | A | 11/1997 | Sablotsky et al. |
| 5,688,232 | A | 11/1997 | Flower |
| 5,694,919 | A | 12/1997 | Rubsamen et al. |
| 5,694,920 | A | 12/1997 | Abrams et al. |
| 5,697,899 | A | 12/1997 | Hillman et al. |
| 5,709,202 | A | 1/1998 | Lloyd et al. |
| 5,713,349 | A | 2/1998 | Keaney |
| 5,724,986 | A | 3/1998 | Jones, Jr. et al. |
| 5,740,793 | A | 4/1998 | Hodson et al. |
| 5,746,711 | A | 5/1998 | Sibalis et al. |
| 5,781,442 | A | 7/1998 | Engleson et al. |
| 5,794,612 | A | 8/1998 | Wachter et al. |
| 5,807,375 | A | 9/1998 | Gross et al. |
| 5,809,997 | A | 9/1998 | Wolf |
| 5,810,888 | A | 9/1998 | Fenn |
| 5,813,397 | A | 9/1998 | Goodman et al. |
| 5,823,179 | A | 10/1998 | Grychowski et al. |
| 5,826,570 | A | 10/1998 | Goodman et al. |
| 5,830,175 | A | 11/1998 | Flower |
| 5,839,430 | A | 11/1998 | Cama |
| 5,843,014 | A | 12/1998 | Lattin et al. |
| 5,848,991 | A | 12/1998 | Gross et al. |
| 5,851,197 | A | 12/1998 | Marano et al. |
| 5,857,994 | A | 1/1999 | Flower |
| 5,860,957 | A | 1/1999 | Jacobsen et al. |
| 5,865,786 | A | 2/1999 | Sibalis et al. |
| 5,865,787 | A | 2/1999 | Shapland et al. |
| 5,873,835 | A | 2/1999 | Hastings et al. |
| 5,894,841 | A | 4/1999 | Voges |
| 5,906,579 | A | 5/1999 | Vander Salm et al. |
| 5,906,597 | A | 5/1999 | McPhee |
| 5,921,237 | A | 7/1999 | Eisele et al. |
| 5,924,997 | A | 7/1999 | Campbell |
| 5,925,021 | A | 7/1999 | Castellano et al. |
| 5,928,201 | A | 7/1999 | Poulsen et al. |
| 5,960,792 | A | 10/1999 | Lloyd et al. |
| 5,967,986 | A | 10/1999 | Cimochowski et al. |
| 5,967,989 | A | 10/1999 | Cimochowski et al. |
| 5,991,655 | A | 11/1999 | Gross et al. |
| 5,997,501 | A | 12/1999 | Gross et al. |
| 6,006,747 | A | 12/1999 | Eisele et al. |
| 6,012,454 | A | 1/2000 | Hodson et al. |
| 6,018,680 | A | 1/2000 | Flower |
| 6,024,976 | A | 2/2000 | Miranda et al. |
| 6,029,083 | A | 2/2000 | Flower et al. |
| 6,053,873 | A | 4/2000 | Govari et al. |
| 6,053,888 | A | 4/2000 | Kong |
| 6,055,980 | A | 5/2000 | Mecikalski et al. |
| RE36,754 | E | 6/2000 | Noel |
| 6,076,519 | A | 6/2000 | Johnson |
| 6,085,740 | A | 7/2000 | Ivri et al. |
| 6,085,742 | A | 7/2000 | Wachter |
| 6,095,141 | A | 8/2000 | Armer et al. |
| 6,105,571 | A | 8/2000 | Coffee |
| 6,109,260 | A | 8/2000 | Bathe |
| 6,116,233 | A | 9/2000 | Denyer et al. |
| 6,119,684 | A | 9/2000 | Nohl et al. |
| 6,125,844 | A | 10/2000 | Samiotes |
| 6,142,146 | A | 11/2000 | Abrams et al. |
| 6,148,815 | A | 11/2000 | Wolf |
| 6,152,130 | A | 11/2000 | Abrams et al. |

(56) References Cited

U.S. PATENT DOCUMENTS

| | | |
|---|---|---|
| 6,196,218 B1 | 3/2001 | Voges |
| 6,196,219 B1 | 3/2001 | Hess et al. |
| 6,198,966 B1 | 3/2001 | Heruth |
| 6,202,642 B1 | 3/2001 | McKinnon et al. |
| 6,221,383 B1 | 4/2001 | Miranda et al. |
| 6,231,560 B1 | 5/2001 | Bui et al. |
| 6,237,398 B1 | 5/2001 | Porat et al. |
| 6,237,589 B1 | 5/2001 | Denyer et al. |
| 6,237,594 B1 | 5/2001 | Davenport |
| 6,245,026 B1 | 6/2001 | Campbell et al. |
| 6,251,079 B1 | 6/2001 | Gambale et al. |
| 6,254,573 B1 | 7/2001 | Haim et al. |
| 6,256,533 B1 | 7/2001 | Yuzhakov et al. |
| 6,260,549 B1 | 7/2001 | Sosiak |
| 6,269,340 B1 | 7/2001 | Ford et al. |
| 6,272,370 B1 | 8/2001 | Gillies et al. |
| 6,283,951 B1 | 9/2001 | Flaherty et al. |
| 6,283,953 B1 | 9/2001 | Ayer et al. |
| 6,309,370 B1 | 10/2001 | Haim et al. |
| 6,315,719 B1 | 11/2001 | Rose et al. |
| 6,316,022 B1 | 11/2001 | Mantelle |
| 6,318,361 B1 | 11/2001 | Sosiak |
| 6,327,486 B1 | 12/2001 | Nissila et al. |
| 6,340,357 B1 | 1/2002 | Poulsen et al. |
| 6,349,724 B1 * | 2/2002 | Burton et al. ............ 128/204.18 |
| 6,352,715 B1 | 3/2002 | Hwang et al. |
| 6,377,848 B1 | 4/2002 | Garde et al. |
| 6,378,520 B1 | 4/2002 | Davenport |
| 6,385,488 B1 | 5/2002 | Flower et al. |
| 6,390,088 B1 | 5/2002 | Nohl et al. |
| 6,394,997 B1 | 5/2002 | Lemelson |
| 6,397,838 B1 | 6/2002 | Zimlich et al. |
| 6,406,426 B1 | 6/2002 | Reuss et al. |
| 6,413,238 B1 | 7/2002 | Maget |
| 6,422,236 B1 | 7/2002 | Nilsson |
| 6,425,392 B1 | 7/2002 | Sosiak |
| 6,427,684 B2 | 8/2002 | Ritsche et al. |
| 6,431,171 B1 | 8/2002 | Burton |
| 6,435,175 B1 | 8/2002 | Stenzler |
| 6,443,146 B1 | 9/2002 | Voges |
| 6,448,303 B1 | 9/2002 | Paul |
| 6,453,195 B1 | 9/2002 | Thompson |
| 6,468,242 B1 | 10/2002 | Wilson et al. |
| 6,484,721 B1 | 11/2002 | Bliss |
| 6,485,461 B1 | 11/2002 | Mason et al. |
| 6,516,796 B1 | 2/2003 | Cox et al. |
| 6,517,481 B2 | 2/2003 | Hoek et al. |
| 6,517,527 B2 | 2/2003 | Gambale et al. |
| 6,520,928 B1 | 2/2003 | Junior et al. |
| 6,527,759 B1 | 3/2003 | Tachibana et al. |
| 6,533,733 B1 | 3/2003 | Ericson et al. |
| 6,536,423 B2 | 3/2003 | Conway |
| 6,540,154 B1 | 4/2003 | Ivri et al. |
| 6,564,093 B1 | 5/2003 | Ostrow et al. |
| 6,568,390 B2 | 5/2003 | Nichols et al. |
| 6,575,932 B1 | 6/2003 | O'Brien et al. |
| 6,578,741 B2 | 6/2003 | Ritsche et al. |
| 6,582,393 B2 | 6/2003 | Sage |
| 6,584,971 B1 | 7/2003 | Denyer et al. |
| 6,585,698 B1 | 7/2003 | Packman et al. |
| 6,589,229 B1 | 7/2003 | Connelly et al. |
| 6,599,281 B1 | 7/2003 | Struys et al. |
| 6,605,072 B2 | 8/2003 | Struys et al. |
| 6,606,989 B1 | 8/2003 | Brand et al. |
| 6,607,508 B2 | 8/2003 | Knauer |
| 6,615,827 B2 | 9/2003 | Greenwood et al. |
| 6,629,524 B1 | 10/2003 | Goodall et al. |
| 6,640,804 B2 | 11/2003 | Ivri et al. |
| 6,651,651 B1 | 11/2003 | Bonney et al. |
| 6,655,381 B2 | 12/2003 | Keane et al. |
| 6,656,148 B2 | 12/2003 | Das et al. |
| 6,678,555 B2 | 1/2004 | Flower et al. |
| 6,685,648 B2 | 2/2004 | Flaherty et al. |
| 6,705,316 B2 | 3/2004 | Blythe et al. |
| 6,715,487 B2 | 4/2004 | Nichols et al. |
| 6,723,077 B2 | 4/2004 | Pickup et al. |
| 6,726,661 B2 | 4/2004 | Munk et al. |
| 6,728,574 B2 | 4/2004 | Ujhelyi et al. |
| 6,738,662 B1 * | 5/2004 | Frank ............... 604/20 |
| 6,745,761 B2 | 6/2004 | Christup et al. |
| 6,745,764 B2 | 6/2004 | Hickle |
| 6,746,429 B2 | 6/2004 | Sadowski et al. |
| 6,748,945 B2 | 6/2004 | Grychowski et al. |
| 6,796,305 B1 * | 9/2004 | Banner et al. ............ 128/204.21 |
| 6,796,956 B2 | 9/2004 | Hartlaub et al. |
| 6,807,965 B1 | 10/2004 | Hickle |
| 6,810,290 B2 | 10/2004 | Lebel et al. |
| 6,854,461 B2 | 2/2005 | Nichols et al. |
| 6,858,011 B2 | 2/2005 | Sehgal |
| 6,866,037 B1 | 3/2005 | Aslin et al. |
| 6,886,557 B2 | 5/2005 | Childers et al. |
| 6,893,415 B2 | 5/2005 | Madsen et al. |
| 6,902,740 B2 | 6/2005 | Schaberg et al. |
| 6,923,784 B2 | 8/2005 | Stein et al. |
| 6,941,168 B2 | 9/2005 | Girouard et al. |
| 6,949,081 B1 | 9/2005 | Chance |
| 6,958,691 B1 | 10/2005 | Anderson et al. |
| 6,961,601 B2 | 11/2005 | Matthews et al. |
| 6,971,383 B2 | 12/2005 | Hickey et al. |
| 6,981,499 B2 | 1/2006 | Anderson et al. |
| 6,983,652 B2 | 1/2006 | Blakley et al. |
| 6,985,771 B2 | 1/2006 | Fischell et al. |
| 6,985,870 B2 | 1/2006 | Martucci et al. |
| 6,990,975 B1 | 1/2006 | Jones et al. |
| 6,999,854 B2 | 2/2006 | Roth |
| 7,010,337 B2 | 3/2006 | Furnary et al. |
| 7,034,692 B2 | 4/2006 | Hickle |
| 7,040,314 B2 | 5/2006 | Nguyen et al. |
| 7,044,911 B2 | 5/2006 | Drinan et al. |
| 7,047,964 B2 | 5/2006 | Bacon |
| 7,054,782 B2 | 5/2006 | Hartlaub |
| 7,072,802 B2 | 7/2006 | Hartlaub |
| 7,089,935 B1 | 8/2006 | Rand |
| 7,097,853 B1 | 8/2006 | Garbe et al. |
| 7,104,972 B2 | 9/2006 | Moller et al. |
| 7,107,988 B2 | 9/2006 | Pinon et al. |
| 7,108,680 B2 | 9/2006 | Rohr et al. |
| 7,117,867 B2 | 10/2006 | Cox et al. |
| 7,138,088 B2 | 11/2006 | Wariar et al. |
| 7,147,170 B2 | 12/2006 | Nguyen et al. |
| 7,168,597 B1 | 1/2007 | Jones et al. |
| 7,181,261 B2 | 2/2007 | Silver et al. |
| 7,191,777 B2 | 3/2007 | Brand et al. |
| 7,198,172 B2 | 4/2007 | Harvey et al. |
| 7,201,734 B2 | 4/2007 | Hickle |
| 7,204,823 B2 | 4/2007 | Estes et al. |
| 7,220,240 B2 | 5/2007 | Struys et al. |
| 7,225,805 B2 | 6/2007 | Bacon |
| 7,232,435 B2 | 6/2007 | Hildebrand et al. |
| 7,242,981 B2 | 7/2007 | Ginggen |
| 7,247,154 B2 | 7/2007 | Hickle |
| 7,261,733 B1 | 8/2007 | Brown et al. |
| 7,267,121 B2 | 9/2007 | Ivri et al. |
| 7,278,983 B2 | 10/2007 | Ireland et al. |
| 7,291,126 B2 | 11/2007 | Shekalim |
| 7,320,675 B2 | 1/2008 | Pastore et al. |
| 7,322,352 B2 | 1/2008 | Minshull et al. |
| 7,322,355 B2 | 1/2008 | Jones et al. |
| 7,331,340 B2 | 2/2008 | Barney |
| 7,342,660 B2 | 3/2008 | Altobelli et al. |
| 7,347,200 B2 | 3/2008 | Jones et al. |
| 7,347,202 B2 | 3/2008 | Aslin et al. |
| 7,347,851 B1 | 3/2008 | Kriksunov |
| 7,367,968 B2 | 5/2008 | Rosenberg et al. |
| 7,380,550 B2 | 6/2008 | Sexton et al. |
| 7,382,263 B2 | 6/2008 | Danowski et al. |
| 7,383,837 B2 | 6/2008 | Robertson et al. |
| 7,387,121 B2 | 6/2008 | Harvey |
| 7,390,311 B2 | 6/2008 | Hildebrand et al. |
| 7,397,730 B2 | 7/2008 | Skyggebjerg et al. |
| 7,415,384 B2 | 8/2008 | Hartlaub |
| 7,424,888 B2 | 9/2008 | Harvey et al. |
| 7,455,667 B2 | 11/2008 | Uhland et al. |
| 7,458,373 B2 | 12/2008 | Nichols et al. |

(56) References Cited

U.S. PATENT DOCUMENTS

| | | | |
|---|---|---|---|
| 7,467,629 B2 | 12/2008 | Rand | |
| 7,483,743 B2 | 1/2009 | Mann et al. | |
| 7,488,305 B2 | 2/2009 | Mickley et al. | |
| 7,495,546 B2 | 2/2009 | Lintell et al. | |
| 7,510,551 B2 | 3/2009 | Uhland et al. | |
| 7,517,332 B2 | 4/2009 | Tonelli et al. | |
| 7,520,278 B2 | 4/2009 | Crowder et al. | |
| 7,530,352 B2 | 5/2009 | Childers et al. | |
| 7,530,975 B2 | 5/2009 | Hunter | |
| 7,537,590 B2 | 5/2009 | Santini et al. | |
| 7,542,798 B2 | 6/2009 | Girouard | |
| 7,544,190 B2 | 6/2009 | Pickup et al. | |
| 7,548,314 B2 | 6/2009 | Altobelli et al. | |
| 7,549,421 B2 | 6/2009 | Levi et al. | |
| 7,552,728 B2 | 6/2009 | Bonney et al. | |
| 7,554,090 B2 | 6/2009 | Coleman et al. | |
| 7,575,003 B2 | 8/2009 | Rasmusssen et al. | |
| 7,581,540 B2 | 9/2009 | Hale et al. | |
| 7,597,099 B2 | 10/2009 | Jones et al. | |
| 7,631,643 B2 | 12/2009 | Morrison et al. | |
| 7,670,329 B2 | 3/2010 | Flaherty et al. | |
| 7,672,726 B2 | 3/2010 | Ginggen | |
| 7,677,467 B2 | 3/2010 | Fink et al. | |
| 7,686,788 B2 | 3/2010 | Freyman et al. | |
| 7,699,060 B2 | 4/2010 | Bahm | |
| 7,699,829 B2 | 4/2010 | Harris et al. | |
| 7,708,011 B2 | 5/2010 | Hochrainer et al. | |
| 7,713,229 B2 | 5/2010 | Veit et al. | |
| 7,715,919 B2 | 5/2010 | Osorio et al. | |
| 7,717,877 B2 | 5/2010 | Lavi et al. | |
| 7,725,161 B2 | 5/2010 | Karmarkar et al. | |
| 7,783,344 B2 | 8/2010 | Lackey et al. | |
| 7,904,133 B2 * | 3/2011 | Gehman et al. | 600/391 |
| 8,016,798 B2 | 9/2011 | Sparks et al. | |
| 8,162,899 B2 | 4/2012 | Tennican | |
| 8,777,894 B2 | 7/2014 | Butterfield | |
| 2001/0000802 A1 | 5/2001 | Soykan et al. | |
| 2001/0022279 A1 | 9/2001 | Denyer et al. | |
| 2002/0000225 A1 | 1/2002 | Schuler et al. | |
| 2002/0002349 A1 | 1/2002 | Flaherty et al. | |
| 2002/0010432 A1 | 1/2002 | Klitmose et al. | |
| 2002/0013615 A1 | 1/2002 | Haim et al. | |
| 2002/0026940 A1 | 3/2002 | Brooker et al. | |
| 2002/0077852 A1 | 6/2002 | Ford et al. | |
| 2002/0099328 A1 | 7/2002 | Scheiner et al. | |
| 2002/0120236 A1 | 8/2002 | Diaz et al. | |
| 2002/0153006 A1 | 10/2002 | Zimlich et al. | |
| 2002/0189612 A1 | 12/2002 | Rand et al. | |
| 2002/0189615 A1 | 12/2002 | Henry et al. | |
| 2002/0198493 A1 | 12/2002 | Diaz et al. | |
| 2003/0004236 A1 | 1/2003 | Meade et al. | |
| 2003/0078561 A1 | 4/2003 | Gambale et al. | |
| 2003/0079744 A1 | 5/2003 | Bonney et al. | |
| 2003/0094508 A1 | 5/2003 | Peng et al. | |
| 2003/0136418 A1 | 7/2003 | Behm et al. | |
| 2003/0140921 A1 | 7/2003 | Smith et al. | |
| 2003/0150446 A1 | 8/2003 | Patel et al. | |
| 2003/0159693 A1 | 8/2003 | Melker et al. | |
| 2003/0168057 A1 | 9/2003 | Snyder et al. | |
| 2003/0171738 A1 | 9/2003 | Konieczynski et al. | |
| 2003/0176804 A1 | 9/2003 | Melker | |
| 2003/0176808 A1 | 9/2003 | Masuo | |
| 2003/0183226 A1 | 10/2003 | Brand et al. | |
| 2003/0205229 A1 | 11/2003 | Crockford et al. | |
| 2004/0004133 A1 | 1/2004 | Ivri et al. | |
| 2004/0019321 A1 | 1/2004 | Sage et al. | |
| 2004/0025871 A1 | 2/2004 | Davies et al. | |
| 2004/0031331 A1 | 2/2004 | Blakley et al. | |
| 2004/0050385 A1 | 3/2004 | Bonney et al. | |
| 2004/0089299 A1 | 5/2004 | Bonney et al. | |
| 2004/0098117 A1 | 5/2004 | Hossainy et al. | |
| 2004/0106902 A1 | 6/2004 | Diaz et al. | |
| 2004/0122530 A1 | 6/2004 | Hansen et al. | |
| 2004/0133154 A1 | 7/2004 | Flaherty et al. | |
| 2004/0139963 A1 | 7/2004 | Ivri et al. | |
| 2004/0158167 A1 | 8/2004 | Smith et al. | |
| 2004/0181196 A1 | 9/2004 | Pickup et al. | |
| 2004/0187864 A1 | 9/2004 | Adams et al. | |
| 2004/0193453 A1 | 9/2004 | Butterfield et al. | |
| 2004/0210199 A1 | 10/2004 | Atterbury et al. | |
| 2004/0254435 A1 | 12/2004 | Mathews et al. | |
| 2005/0010166 A1 | 1/2005 | Hickle | |
| 2005/0045734 A1 | 3/2005 | Peng et al. | |
| 2005/0059924 A1 | 3/2005 | Katz et al. | |
| 2005/0072421 A1 | 4/2005 | Suman et al. | |
| 2005/0081845 A1 | 4/2005 | Barney et al. | |
| 2005/0087189 A1 | 4/2005 | Crockford et al. | |
| 2005/0137626 A1 | 6/2005 | Pastore et al. | |
| 2005/0139651 A1 * | 6/2005 | Lim et al. | 235/380 |
| 2005/0155602 A1 | 7/2005 | Lipp | |
| 2005/0165342 A1 | 7/2005 | Odland | |
| 2005/0171451 A1 | 8/2005 | Yeo et al. | |
| 2005/0172956 A1 | 8/2005 | Childers et al. | |
| 2005/0172958 A1 | 8/2005 | Singer et al. | |
| 2005/0183725 A1 | 8/2005 | Gumaste et al. | |
| 2005/0203637 A1 | 9/2005 | Edman et al. | |
| 2005/0235732 A1 | 10/2005 | Rush | |
| 2005/0236501 A1 | 10/2005 | Zimlich et al. | |
| 2005/0245906 A1 | 11/2005 | Makower et al. | |
| 2005/0247312 A1 | 11/2005 | Davies | |
| 2005/0251289 A1 | 11/2005 | Bonney et al. | |
| 2005/0274378 A1 | 12/2005 | Bonney et al. | |
| 2006/0005842 A1 * | 1/2006 | Rashad et al. | 128/207.18 |
| 2006/0030813 A1 | 2/2006 | Chance | |
| 2006/0031099 A1 | 2/2006 | Vitello et al. | |
| 2006/0037612 A1 | 2/2006 | Herder et al. | |
| 2006/0042632 A1 | 3/2006 | Bishop et al. | |
| 2006/0058593 A1 | 3/2006 | Drinan et al. | |
| 2006/0090752 A1 | 5/2006 | Imondi et al. | |
| 2006/0130832 A1 | 6/2006 | Schechter et al. | |
| 2006/0131350 A1 | 6/2006 | Schechter et al. | |
| 2006/0167530 A1 | 7/2006 | Flaherty et al. | |
| 2006/0178586 A1 | 8/2006 | Dobak | |
| 2006/0184087 A1 | 8/2006 | Wariar et al. | |
| 2006/0191534 A1 | 8/2006 | Hickey et al. | |
| 2006/0201499 A1 | 9/2006 | Muellinger et al. | |
| 2006/0204532 A1 | 9/2006 | John et al. | |
| 2006/0231093 A1 | 10/2006 | Burge et al. | |
| 2006/0243277 A1 | 11/2006 | Denyer et al. | |
| 2006/0253005 A1 | 11/2006 | Drinan | |
| 2006/0283465 A1 | 12/2006 | Nickel | |
| 2007/0023034 A1 | 2/2007 | Jongejan et al. | |
| 2007/0023036 A1 | 2/2007 | Grychowski et al. | |
| 2007/0043591 A1 | 2/2007 | Meretei et al. | |
| 2007/0044793 A1 | 3/2007 | Kleinstreuer et al. | |
| 2007/0060800 A1 | 3/2007 | Drinan et al. | |
| 2007/0074722 A1 | 4/2007 | Giroux et al. | |
| 2007/0088334 A1 | 4/2007 | Hillis et al. | |
| 2007/0091273 A1 | 4/2007 | Sullivan et al. | |
| 2007/0107517 A1 | 5/2007 | Arnold et al. | |
| 2007/0123829 A1 | 5/2007 | Atterbury et al. | |
| 2007/0125370 A1 | 6/2007 | Denyer et al. | |
| 2007/0157931 A1 | 7/2007 | Parker et al. | |
| 2007/0161879 A1 | 7/2007 | Say et al. | |
| 2007/0169778 A1 | 7/2007 | Smith et al. | |
| 2007/0197954 A1 | 8/2007 | Keenan | |
| 2007/0203411 A1 | 8/2007 | Say et al. | |
| 2007/0208322 A1 | 9/2007 | Rantala et al. | |
| 2007/0209659 A1 | 9/2007 | Ivri et al. | |
| 2007/0213658 A1 | 9/2007 | Hickle | |
| 2007/0221218 A1 | 9/2007 | Warden et al. | |
| 2007/0224128 A1 | 9/2007 | Dennis et al. | |
| 2007/0240712 A1 | 10/2007 | Fleming et al. | |
| 2007/0256688 A1 | 11/2007 | Schuster et al. | |
| 2007/0258894 A1 | 11/2007 | Melker et al. | |
| 2007/0295329 A1 | 12/2007 | Lieberman et al. | |
| 2007/0299550 A1 | 12/2007 | Nishijima et al. | |
| 2008/0009800 A1 | 1/2008 | Nickel | |
| 2008/0021379 A1 | 1/2008 | Hickle | |
| 2008/0039700 A1 | 2/2008 | Drinan et al. | |
| 2008/0051667 A1 | 2/2008 | Goldreich | |
| 2008/0058703 A1 | 3/2008 | Subramony et al. | |
| 2008/0077080 A1 | 3/2008 | Hengstenberg et al. | |
| 2008/0078382 A1 | 4/2008 | LeMahieu et al. | |

(56) References Cited

U.S. PATENT DOCUMENTS

| | | | |
|---|---|---|---|
| 2008/0078385 A1 | 4/2008 | Xiao et al. | |
| 2008/0082001 A1 | 4/2008 | Hatlestad et al. | |
| 2008/0086112 A1 | 4/2008 | Lo et al. | |
| 2008/0091138 A1 | 4/2008 | Pastore et al. | |
| 2008/0114299 A1 | 5/2008 | Damgaard-Sorensen et al. | |
| 2008/0125759 A1 | 5/2008 | Konieczynski et al. | |
| 2008/0142002 A1 | 6/2008 | Fink et al. | |
| 2008/0147004 A1 | 6/2008 | Mann et al. | |
| 2008/0147050 A1 | 6/2008 | Mann et al. | |
| 2008/0173301 A1 | 7/2008 | Deaton et al. | |
| 2008/0177246 A1 | 7/2008 | Sullican et al. | |
| 2008/0178872 A1 | 7/2008 | Genova et al. | |
| 2008/0200804 A1 | 8/2008 | Hartlep et al. | |
| 2008/0216834 A1 | 9/2008 | Easley et al. | |
| 2008/0221408 A1 | 9/2008 | Hoarau et al. | |
| 2008/0262469 A1 | 10/2008 | Brister et al. | |
| 2008/0269689 A1 | 10/2008 | Edwards et al. | |
| 2008/0281276 A1 | 11/2008 | Shekalim | |
| 2008/0306436 A1 | 12/2008 | Edwards et al. | |
| 2008/0306444 A1 | 12/2008 | Brister et al. | |
| 2008/0306449 A1 | 12/2008 | Kristensen et al. | |
| 2009/0005763 A1 | 1/2009 | Makower et al. | |
| 2009/0024112 A1 | 1/2009 | Edwards et al. | |
| 2009/0025714 A1 | 1/2009 | Denyer et al. | |
| 2009/0025718 A1 | 1/2009 | Denyer et al. | |
| 2009/0030285 A1* | 1/2009 | Andersen | 600/300 |
| 2009/0048526 A1 | 2/2009 | Aarts et al. | |
| 2009/0048556 A1 | 2/2009 | Durand | |
| 2009/0056708 A1 | 3/2009 | Stenzler et al. | |
| 2009/0064997 A1 | 3/2009 | Li | |
| 2009/0082829 A1 | 3/2009 | Panken et al. | |
| 2009/0107503 A1 | 4/2009 | Baran | |
| 2009/0151718 A1 | 6/2009 | Hunter et al. | |
| 2009/0156952 A1 | 6/2009 | Hunter et al. | |
| 2009/0163781 A1 | 6/2009 | Say et al. | |
| 2009/0187167 A1 | 7/2009 | Sexton et al. | |
| 2009/0194104 A1 | 8/2009 | Van Sickle | |
| 2009/0211576 A1 | 8/2009 | Lehtonen et al. | |
| 2009/0213373 A1 | 8/2009 | Altobelli et al. | |
| 2009/0216194 A1 | 8/2009 | Elgard et al. | |
| 2009/0221087 A1 | 9/2009 | Martin et al. | |
| 2009/0227941 A1 | 9/2009 | Say et al. | |
| 2009/0229607 A1 | 9/2009 | Brunnberg et al. | |
| 2009/0241951 A1 | 10/2009 | Jafari et al. | |
| 2009/0241955 A1 | 10/2009 | Jafari et al. | |
| 2009/0270752 A1 | 10/2009 | Coifman | |
| 2009/0301472 A1 | 12/2009 | Kim et al. | |
| 2009/0314372 A1 | 12/2009 | Ruskewicz et al. | |
| 2009/0326509 A1 | 12/2009 | Muse et al. | |
| 2009/0326510 A1 | 12/2009 | Haefner et al. | |
| 2010/0012120 A1 | 1/2010 | Herder et al. | |
| 2010/0031957 A1 | 2/2010 | McIntosh et al. | |
| 2010/0049004 A1 | 2/2010 | Edman et al. | |
| 2010/0049172 A1 | 2/2010 | Chance | |
| 2010/0078015 A1 | 4/2010 | Imran | |
| 2010/0094099 A1 | 4/2010 | Levy et al. | |
| 2010/0099967 A1 | 4/2010 | Say et al. | |
| 2010/0100078 A1 | 4/2010 | Say et al. | |
| 2010/0100160 A1 | 4/2010 | Edman et al. | |
| 2010/0106098 A1 | 4/2010 | Atterbury et al. | |
| 2010/0114026 A1 | 5/2010 | Karratt et al. | |
| 2010/0114060 A1 | 5/2010 | Ginggen et al. | |
| 2010/0116070 A1 | 5/2010 | Farina et al. | |
| 2010/0121314 A1 | 5/2010 | Iobbi | |
| 2010/0122697 A1 | 5/2010 | Przekwas et al. | |
| 2010/0268111 A1 | 10/2010 | Drinan et al. | |
| 2011/0224912 A1 | 9/2011 | Bhavaraju et al. | |
| 2011/0230732 A1 | 9/2011 | Edman et al. | |

FOREIGN PATENT DOCUMENTS

| | | |
|---|---|---|
| JP | 6296633 | 10/1994 |
| JP | 2001-061799 | 3/2001 |
| JP | 2008-525063 | 7/2008 |
| WO | WO8102982 | 10/1981 |
| WO | WO8607269 | 12/1986 |
| WO | WO9207599 | 5/1992 |
| WO | WO9209324 | 6/1992 |
| WO | WO9211808 | 7/1992 |
| WO | WO9215353 | 9/1992 |
| WO | WO9217231 | 10/1992 |
| WO | WO9306803 | 4/1993 |
| WO | WO9312823 | 7/1993 |
| WO | WO9405359 | 3/1994 |
| WO | WO9408655 | 4/1994 |
| WO | WO9416755 | 8/1994 |
| WO | WO9416756 | 8/1994 |
| WO | WO9416759 | 8/1994 |
| WO | WO9427653 | 12/1994 |
| WO | WO9507723 | 3/1995 |
| WO | WO9507724 | 3/1995 |
| WO | WO9513838 | 5/1995 |
| WO | WO9526769 | 10/1995 |
| WO | WO9610440 | 4/1996 |
| WO | WO9616686 | 6/1996 |
| WO | WO9625186 | 8/1996 |
| WO | WO9625978 | 8/1996 |
| WO | WO9627341 | 9/1996 |
| WO | WO9630078 | 10/1996 |
| WO | WO9707896 | 3/1997 |
| WO | WO9711655 | 4/1997 |
| WO | WO9711742 | 4/1997 |
| WO | WO9711743 | 4/1997 |
| WO | WO9726934 | 7/1997 |
| WO | WO9733640 | 9/1997 |
| WO | WO9733645 | 9/1997 |
| WO | WO9748431 | 12/1997 |
| WO | WO9800188 | 1/1998 |
| WO | WO9801168 | 1/1998 |
| WO | WO9806450 | 2/1998 |
| WO | WO9814235 | 4/1998 |
| WO | WO9832479 | 7/1998 |
| WO | WO9839057 | 9/1998 |
| WO | WO9844984 | 10/1998 |
| WO | WO9850095 | 11/1998 |
| WO | WO9900144 | 1/1999 |
| WO | WO9930760 | 6/1999 |
| WO | WO9965551 | 12/1999 |
| WO | WO0001434 | 1/2000 |
| WO | WO0007652 | 2/2000 |
| WO | WO0018339 | 4/2000 |
| WO | WO0021598 | 4/2000 |
| WO | WO0027278 | 5/2000 |
| WO | WO0032267 | 6/2000 |
| WO | WO0038770 | 7/2000 |
| WO | WO0043059 | 7/2000 |
| WO | WO0047253 | 8/2000 |
| WO | WO0050111 | 8/2000 |
| WO | WO0053247 | 9/2000 |
| WO | WO0059483 | 10/2000 |
| WO | 01/05463 | 1/2001 |
| WO | WO0113973 | 3/2001 |
| WO | WO0124851 | 4/2001 |
| WO | WO0130419 | 5/2001 |
| WO | WO0158236 | 8/2001 |
| WO | WO0168169 | 9/2001 |
| WO | WO0183007 | 11/2001 |
| WO | WO0185027 | 11/2001 |
| WO | WO0187378 | 11/2001 |
| WO | WO0189607 | 11/2001 |
| WO | WO0200280 | 1/2002 |
| WO | WO0202052 | 1/2002 |
| WO | WO0204043 | 1/2002 |
| WO | WO0217988 | 3/2002 |
| WO | WO0217998 | 3/2002 |
| WO | WO0224257 | 3/2002 |
| WO | WO0224268 | 3/2002 |
| WO | WO0234318 | 5/2002 |
| WO | WO0236181 | 5/2002 |
| WO | WO02053223 | 7/2002 |
| WO | WO02072178 | 9/2002 |
| WO | WO02076533 | 10/2002 |
| WO | WO02078535 | 10/2002 |

(56) References Cited

FOREIGN PATENT DOCUMENTS

| | | |
|---|---|---|
| WO | WO02081016 | 10/2002 |
| WO | WO02089879 | 11/2002 |
| WO | WO02089884 | 11/2002 |
| WO | WO02096489 | 12/2002 |
| WO | WO03006091 | 1/2003 |
| WO | WO03008014 | 1/2003 |
| WO | WO03020349 | 3/2003 |
| WO | WO03022327 | 3/2003 |
| WO | WO03028797 | 4/2003 |
| WO | WO03035172 | 5/2003 |
| WO | WO03038566 | 5/2003 |
| WO | WO03045302 | 6/2003 |
| WO | WO03059413 | 7/2003 |
| WO | WO03071930 | 9/2003 |
| WO | WO03073977 | 9/2003 |
| WO | WO03086505 | 10/2003 |
| WO | WO03090821 | 11/2003 |
| WO | WO03097120 | 11/2003 |
| WO | WO2004009161 | 1/2004 |
| WO | WO2004011067 | 2/2004 |
| WO | WO2004012801 | 2/2004 |
| WO | WO2004020024 | 3/2004 |
| WO | WO2004021882 | 3/2004 |
| WO | WO2004022128 | 3/2004 |
| WO | WO2004022153 | 3/2004 |
| WO | WO2004022242 | 3/2004 |
| WO | WO2004026380 | 4/2004 |
| WO | WO2004032989 | 4/2004 |
| WO | WO2004034998 | 4/2004 |
| WO | WO2004041334 | 5/2004 |
| WO | WO2004041339 | 5/2004 |
| WO | WO2004045690 | 6/2004 |
| WO | WO2004060436 | 7/2004 |
| WO | WO2004060443 | 7/2004 |
| WO | WO2004060447 | 7/2004 |
| WO | WO2004080522 | 9/2004 |
| WO | WO2004088567 | 10/2004 |
| WO | WO2005009514 | 2/2005 |
| WO | WO2005011779 | 2/2005 |
| WO | WO2005028008 | 3/2005 |
| WO | WO2005031317 | 4/2005 |
| WO | WO2005039750 | 5/2005 |
| WO | WO2005046559 | 5/2005 |
| WO | WO2005051177 | 6/2005 |
| WO | WO2005072798 | 8/2005 |
| WO | WO2005084275 | 9/2005 |
| WO | WO2005084738 | 9/2005 |
| WO | WO2005087299 | 9/2005 |
| WO | WO2005102412 | 11/2005 |
| WO | WO2005102417 | 11/2005 |
| WO | WO2005102418 | 11/2005 |
| WO | WO2005102428 | 11/2005 |
| WO | WO2005120615 | 12/2005 |
| WO | WO2005123002 | 12/2005 |
| WO | WO2006003665 | 1/2006 |
| WO | WO2006009596 | 1/2006 |
| WO | WO2006015299 | 2/2006 |
| WO | 2006/029090 | 3/2006 |
| WO | WO2006022714 | 3/2006 |
| WO | WO2006023644 | 3/2006 |
| WO | WO2006035443 | 4/2006 |
| WO | WO2006044206 | 4/2006 |
| WO | WO2006045524 | 5/2006 |
| WO | 2006/069323 | 6/2006 |
| WO | WO2006058426 | 6/2006 |
| WO | WO2006060106 | 6/2006 |
| WO | WO2006079898 | 8/2006 |
| WO | WO2006096286 | 9/2006 |
| WO | WO2006098933 | 9/2006 |
| WO | WO2006098936 | 9/2006 |
| WO | WO2006113408 | 10/2006 |
| WO | 2006/116718 A2 | 11/2006 |
| WO | WO2006120253 | 11/2006 |
| WO | WO2006124759 | 11/2006 |
| WO | WO2006125577 | 11/2006 |
| WO | WO2006127257 | 11/2006 |
| WO | WO2006127905 | 11/2006 |
| WO | WO2006127953 | 11/2006 |
| WO | WO2006128794 | 12/2006 |
| WO | WO2006130098 | 12/2006 |
| WO | WO2006133101 | 12/2006 |
| WO | WO2007012854 | 2/2007 |
| WO | 2007/028035 A2 | 3/2007 |
| WO | WO2007031740 | 3/2007 |
| WO | WO2007034237 | 3/2007 |
| WO | WO2007041158 | 4/2007 |
| WO | WO2007041471 | 4/2007 |
| WO | WO2007051563 | 5/2007 |
| WO | WO2007070093 | 6/2007 |
| WO | WO2007070695 | 6/2007 |
| WO | 2007/120884 | 10/2007 |
| WO | WO2007125699 | 11/2007 |
| WO | WO2007127981 | 11/2007 |
| WO | WO2007131025 | 11/2007 |
| WO | WO2008008281 | 1/2008 |
| WO | WO2008016698 | 2/2008 |
| WO | WO2008021252 | 2/2008 |
| WO | WO2008022010 | 2/2008 |
| WO | WO2008029403 | 3/2008 |
| WO | WO2008030837 | 3/2008 |
| WO | WO2008037801 | 4/2008 |
| WO | WO2008038241 | 4/2008 |
| WO | WO2008039091 | 4/2008 |
| WO | WO2008043724 | 4/2008 |
| WO | WO2008052039 | 5/2008 |
| WO | WO2008073806 | 6/2008 |
| WO | WO2008077706 | 7/2008 |
| WO | WO2008078287 | 7/2008 |
| WO | 2008/095183 | 8/2008 |
| WO | WO2008103620 | 8/2008 |
| WO | WO2008115906 | 9/2008 |
| WO | WO2008117226 | 10/2008 |
| WO | WO2008127743 | 10/2008 |
| WO | WO2008130801 | 10/2008 |
| WO | WO2008134107 | 11/2008 |
| WO | WO2008134545 | 11/2008 |
| WO | WO2008152588 | 12/2008 |
| WO | WO2008154312 | 12/2008 |
| WO | WO2008154504 | 12/2008 |
| WO | WO2009003989 | 1/2009 |
| WO | WO2009008001 | 1/2009 |
| WO | WO2009013501 | 1/2009 |
| WO | WO2009013670 | 1/2009 |
| WO | WO2009023247 | 2/2009 |
| WO | WO2009035759 | 3/2009 |
| WO | WO2009042379 | 4/2009 |
| WO | WO2009049252 | 4/2009 |
| WO | WO2009063421 | 5/2009 |
| WO | WO2009072079 | 6/2009 |
| WO | WO2009076363 | 6/2009 |
| WO | WO2009079589 | 6/2009 |
| WO | WO2009081262 | 7/2009 |
| WO | WO2009091851 | 7/2009 |
| WO | WO2009098648 | 8/2009 |
| WO | WO2009105337 | 8/2009 |
| WO | WO2009110702 | 9/2009 |
| WO | WO2009126653 | 10/2009 |
| WO | WO2009137661 | 11/2009 |
| WO | WO2009140251 | 11/2009 |
| WO | WO2009140360 | 11/2009 |
| WO | WO2009145801 | 12/2009 |
| WO | WO2009155335 | 12/2009 |
| WO | WO2010007573 | 1/2010 |
| WO | WO2010007574 | 1/2010 |
| WO | WO2010008424 | 1/2010 |
| WO | WO2010010473 | 1/2010 |
| WO | WO2010021589 | 2/2010 |
| WO | WO2010023591 | 3/2010 |
| WO | WO2010025428 | 3/2010 |
| WO | WO2010025431 | 3/2010 |
| WO | WO2010029054 | 3/2010 |
| WO | WO2010037828 | 4/2010 |
| WO | WO2010042034 | 4/2010 |
| WO | WO2010043054 | 4/2010 |

(56) References Cited

FOREIGN PATENT DOCUMENTS

| WO | WO2010045460 | 4/2010 |
|---|---|---|
| WO | WO2010051551 | 5/2010 |
| WO | WO2010052275 | 5/2010 |
| WO | WO2010062675 | 6/2010 |

OTHER PUBLICATIONS

Juvenile Diabetes Research Foundation International (JDRF), "Artificial Pancreas Project" (2010); http://www.artificialpancreasproject.com/; 3 pp.

Lifescan, "OneTouch UltraLink™" http://www.lifescan.com/products/meters/ultralink (N.D.) 2 pp.

Medtronic, "CareLink Therapy Management Software for Diabetes" (2010); https://carelink.minimed.com/patient/entry.jsp?bhcp=1; 1 pp.

Medtronic, "Carelink™ USB" (n.d.) http://www.medtronicdiabetes.com/pdf/carelink_usb_factsheet.pdf 2pp.

Medtronic "The New MiniMed Paradigm® REAL-Time Revel™ System" http://www.medtronicdiabetes.com/products/index.html; 2 pp.

Medtronic, "MINI MED Paradigm ® Revel ™ Insulin Pump" (n.d.) http://www.medtronicdiabetes.com/products/insulinpumps/index.html; 2 pp.

Medtronic, Mini Med Paradigm™ Veo™ System: Factsheet (2010). http://www.medtronic-diabetes.com.au/downloads/Paradigm%20Veo%20Factsheet.pdf ; 4 pp.

Park, "Medtronic to Buy MiniMed for $3.7 Billion" (2001) HomeCare; http://homecaremag.com/mag/medical_medtronic_buy_minimed/; 2 pp.

Nikander et al., "The Adaptive Delivery System in a Telehealth Setting: Patient Acceptance, Performance and Feasibility" Journal of Aerosol Medicine and Pulmonary Drug Delivery; vol. 23, Supp. 1, (2010) pp. S21-S27.

Prutchi et al., "Design and Development of Medical Electronic Instrumentation: A Practical Perspective of the Design, Construction, and Test of Medical Devices" Wiley-Interscience (2005) pp. 12-14.

* cited by examiner

SMART PARENTERAL ADMINISTRATION SYSTEM

CROSS-REFERENCE TO RELATED APPLICATIONS

This application is a continuation application of PCT application serial no. PCT/US2007/15547 designating the United States and filed on Jul. 6, 2007; which application pursuant to 35 U.S.C. §119 (e), claims priority to the filing date of: U.S. Provisional Patent Application Ser. No. 60/819,750 filed Jul. 7, 2006; U.S. Provisional Patent Application Ser. No. 60/891,883 filed Feb. 27, 2007; U.S. Provisional Patent Application Ser. No. 60/940,631 filed May 29, 2007; and U.S. Provisional Patent Application Ser. No. 60/946,706 filed Jun. 27, 2007; the disclosures of which applications are herein incorporated by reference.

INTRODUCTION

The parenteral administration (by which is meant administration in a manner other than through the digestive tract, such as by intravenous or intramuscular injection or inhalation) of beneficial agents and fluids is an established clinical practice. Parenteral administration of beneficial agents is an effective remedy for many patients when administered properly and according to instructions. However, studies have shown that, on average, about 10% of patients receive an incorrect injectable medication. For example, a significant percentage of serious errors are associated with the administration of intravenous (IV) medication.

A patient's response to drugs delivered intravenously is rapid because the gastrointestinal system is bypassed. Thus, if an error is made, there is little time to compensate. Most critical drugs are delivered intravenously. Correct administration is a process that often involves several individuals for delivering an accurate dose of a drug to a particular patient at a prescribed time and through a particular administration route. It is not difficult to comprehend the potential for error, as well as the undesirable probability that the occurrence of an error can result in one or more detrimental effects to the patient.

An intravenous error may be induced at any time throughout the process of ordering, transcribing, dispensing, and administering a drug. For example, an ordering error may occur because an order is illegible, incomplete, or entered on the wrong patient's chart, because a decimal is misplaced or inappropriate, or unacceptable prescription abbreviations are used, or because an inappropriate drug is selected or a patient's allergies are not properly identified. Transcription errors may occur because an order was not transcribed, not completely signed off, or incorrectly transcribed onto the Medication Administration Record (MAR). Also, on occasion a patient's allergies are not transcribed or a transcription is illegible. Dispensing errors may occur with respect to the dose, or the identification of the medication or patient. An administration error may occur at any time during the course of a patient's care and may concern the patient or drug identification, or the time, dose, or route of drug administration. It is notable that research indicates that 60-80% of intravenous errors are attributed to humans.

It follows then that one way to reduce the potential for error is to automate as much as possible the process of drug ordering, transcribing, dispensing, and administering.

Information technology may be utilized for automating portions of the drug ordering, transcribing, dispensing, and administration process. For example, the potential for error may be reduced by cross referencing infusion data used to program a pump, by reviewing data programmed into a pump prior to enabling the pump to operate, and/or by detecting if programmed data is changed.

Several systems have been developed in an attempt to reduce the above described errors. Examples of such systems are disclosed in U.S. Pat. Nos. 5,781,442; 5,317,506 and 6,985,870.

Despite the presence of these and other systems, there continues to be a need for improved systems. For example, it would be an important advancement in the art if a parenteral administration system could be developed that provided for a prospective definitive confirmation of a patient being properly matched with a dosage without the need for any human intervention. Also of interest would be the development of a system which provides for a definitive record of whether the proper beneficial agent and amount has been administered, and whether the medication has been administered at the proper time, again without the need for any human intervention. These advantages are available through the present smart parenteral delivery invention.

SUMMARY

The inventive systems and methods of use described herein provide, for the first time, accurate evaluation of a fluid transfer event between a fluid delivery device and a patient. The evaluation can be prospective, such that the evaluation provides beforehand knowledge about a future or contemplated fluid transfer event, i.e., an event that has not yet occurred. For example, the evaluation made possible by embodiments of the systems and methods of the invention provides prospective knowledge that a patient is properly matched to a future fluid delivery event from a parenteral fluid deliver device. The evaluation can also be historic, such that the evaluation provides knowledge about a fluid transfer event that has already occurred. In addition, the inventive smart parenteral administration system provides definitive, automatic, and specific identification and detection of parenteral administration of fluids, e.g., fluids that include beneficial agents, to a patient from a parenteral fluid transfer device. In yet other embodiments, the evaluation is real-time, such that that the evaluation provides knowledge about the fluid transfer event as it is occurring.

Specific prospective, real-time and/or historical identification and detection of a parenteral fluid transfer event is achieved with an intelligent fluid delivery system. Embodiments of the invention include an intelligent fluid delivery system which includes a patient associated identifier and a parenteral fluid delivery device (such as a syringe, intravenous administration device, inhaler, or dialysis device, as reviewed in greater detail below). The delivery device and identifier are configured so that a fluid transfer signal can be transmitted between them using the patient's body as a communication medium. By using the patient's body as a communication medium for the fluid transfer signal, prospective, real-time and/or historical definitive knowledge about a prospective and/or actual fluid transfer event of fluid between the delivery device and the patient is automatically obtained. Since the knowledge is automatically obtained, no human intervention is required to obtain the knowledge. Instead, without any human intervention, the system obtains the knowledge and provides it to a user for use, e.g., by outputting data comprising the knowledge to a user and/or recording the data to a suitable recording medium, such as a computer readable medium. Furthermore, the knowledge about the fluid delivery event is definitive, such that one can know for sure that the knowledge is about the specific patient and the specific fluid delivery device of interest, again without the requirements of any human intervention or verification.

The content of the fluid transfer signal may vary widely depending on a number of factors, including but not limited to: the direction of the fluid transfer signal (for example whether it travels from the patient associated identifier to the fluid delivery device and/or from the fluid delivery device to the patient associated identifier); the configuration of the system, e.g., whether the patient associated identifier broadcasts simple patient identification information or more complex patient information, such as health history information, one or more physiological parameters, etc.; whether additional components are present in the system, e.g., a hospital information system, signal relay devices, etc.; whether the purpose of the system is to provide for prospective and/or historical administration data, etc.; and the like.

As indicated above, in certain embodiments the fluid transfer signal is one that is employed in prospective applications. Prospective applications of the invention are those applications where the system is employed to automatically confirm that an intended fluid transfer event is correct for a given patient. For example, a prospective application is one where the fluid transfer signal provides information that a fluid connection has been established between the fluid delivery device and the patient and that the device is ready to transfer fluid to the patient. In yet other embodiments, the fluid transfer signal is one that is employed in historical applications. Historical applications as described herein include retrospective applications, e.g., where the knowledge is employed after the fluid transfer event has occurred, for example in determining an accurate medication history for the patient, etc. For example, the fluid transfer signal in embodiments of such applications is one that provides for actual knowledge that fluid has been parenterally transferred from the device to the patient. In yet other embodiments, the fluid transfer signal is one that is employed in real-time applications, e.g., where the knowledge is employed as the fluid is being transferred between the delivery device and the patient.

Embodiments of the invention include delivery devices that are configured to transmit the fluid transfer signal only when fluid is delivered from the device to the patient and in a manner such that transmission can only occur when the device actually contacts the patient and fluid is transferred to the patient.

As reviewed above, the content of the fluid transfer signal may vary greatly. With respect to prospective applications, the fluid transfer signal may provide for simple identification data, or more complex data such as patient history, prescription information, etc. For historical applications, the fluid transfer signal may be qualitative, e.g., provide a simple yes or no indication of whether transfer has occurred, or quantitative, e.g., provide more detailed information about the fluid transfer, such as the amount of fluid transferred, etc.

The above and additional embodiments of the inventive system are now described in greater detail below.

DETAILED DESCRIPTION

Figure 1:
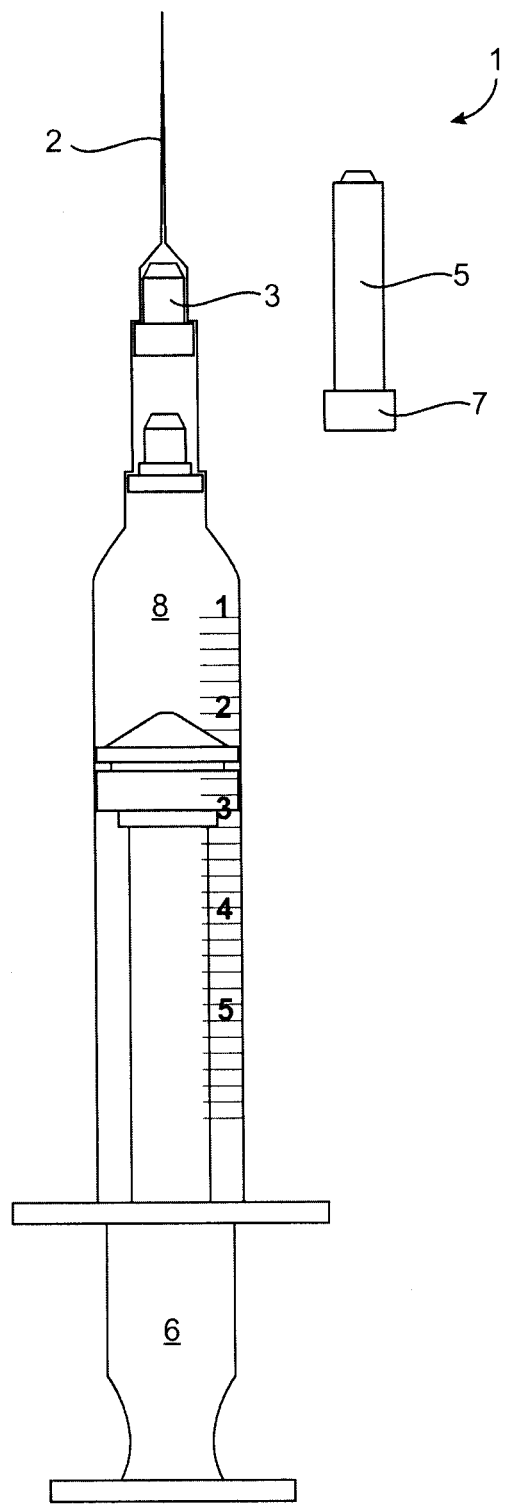
FIG. 1 illustrates a smart therapeutics intramuscular injection system that signals the type of beneficial agent extracted from a vial.

As summarized above, the invention provides methods and systems for evaluating a fluid transfer event between a parenteral fluid delivery device and a patient. The evaluation of the fluid transfer event can be prospective, real-time and/or historic, as desired, and take a variety of different formats. For example, prospective evaluation of a fluid transfer event includes situations where a determination is made of whether a given transfer event is properly matched to a given patient, and may further include subsequent action based on the determination, e.g., initiation of fluid transfer from the device to the patient if a proper match is determined, sounding of an alarm and/or inhibition of fluid transfer if a proper match is not determined, etc. Real-time evaluation of a fluid transfer event includes situations where a determination is made as to whether a given fluid transfer event should be continued once initiated, e.g., based on received physiological parameters from the patient, a determination of what fluids were actually administered to a patient, including when, etc. Historic evaluation includes situations where knowledge regarding actual fluid transfer events that have occurred is employed, e.g., in developing a true patient medication history, etc.

In further describing various aspects of the invention, general aspects of the inventive systems and methods are reviewed first in greater detail, and then in view of specific embodiments.

General Description of Systems and Methods

Aspects of the invention include smart parenteral fluid delivery systems that provide, for the first time, a truly accurate and automated evaluation of a fluid transfer event, whether the evaluation may be prospective, real-time or retrospective. The system is smart in that no human intervention is required for the evaluation. Furthermore, the system as a whole includes processing capability that is configured to receive one or more inputs (for example in the form of fluid transfer signals) and process the input(s) to make an evaluation about a given fluid transfer event.

Embodiments of systems of the invention include a parenteral fluid delivery device and a patient associated identifier. The parenteral fluid delivery device and the patient associated identifier are configured so that a fluid transfer signal can be transmitted between the two components using the body of the patient as a communication medium. To employ the body as a communication medium for the fluid transfer signal, a fluid communication between the fluid delivery device and the patient is first established. As the body of the patient is used as a communication medium, the signal that is transferred between the parenteral fluid delivery device and the patient travels through the body, (for example in a direction from the patient associated identifier to the delivery device and/or from the delivery device to the patient associated identifier), and requires the body as the conduction medium. In certain embodiments, the fluid transfer signal is conductively transmitted between the fluid delivery device and the patient associated identifier using the patient as a conductive medium.

As the body is required as a conduction medium and requires the establishment of fluid transfer connection between the fluid delivery device and the patient, receipt of the signal (either at the patient associated identifier, the parenteral fluid delivery device or another component of the system, such as reviewed in greater detail below) provides accurate knowledge upon which an evaluation of a fluid transfer event may be made. This accurate knowledge can then be further employed in a variety of different ways, depending on the application, where such applications include prospective, real-time and historic applications. Examples of prospective applications are those in which the fluid transfer signal is employed to determine beforehand one or more aspects about a contemplated or future fluid delivery event between the fluid delivery device and the patient, such as whether the type and/or dosage of a fluid is appropriate for the patient. Examples of historic or retrospective applications of the methods and systems of the invention include applications where the fluid transfer signal is employed to obtain an accurate history of a fluid(s) that has been delivered to a patient via a parenteral fluid delivery device.

Patient Associated Identifier

As summarized above, a component of the systems of the invention is a patient associated identifier. The patient associated identifier is a device that is configured to be associated with the patient, for example either topically or implanted, and includes a communications element that performs at least one of broadcasting and receiving functions. The patient associated identifier is one that at least provides identifying information about the patient. The identifier can be configured in a variety of different ways, including formats that are configured to simply broadcast identifying information about the patient (where the patient associated identifier may only include a broadcasting element) to more complex formats where the identifier receives information about a fluid transfer event (such as where the patient associated identifier includes a receiver element) and internally processes that information to evaluate the fluid transfer event in some manner. As such, in certain embodiments the identifiers are configured to simply broadcast identifying information about the patient to the fluid delivery device. In such embodiments, the identifiers are signal receivers that are configured to receive a signal from a parenteral fluid delivery device enabled to transmit a fluid transfer signal. Patient associated identifiers of interest include, but are not limited to, those described in: PCT/US2006/16370 titled "Pharma-Informatics System" and filed on Apr. 28, 2006; as well as U.S. Provisional Application Ser. No. 60/887,780 titled "Signal Receivers for Pharma-Informatics Systems" filed on Feb. 1, 2007; the disclosures of which are herein incorporated by reference.

In certain embodiments, the patient associated identifier is one that is sized to be stably associated with a living subject in a manner that does not substantially impact movement of the living subject. As such, the patient associated identifier has dimensions that, when employed with a subject, such as a human subject, will not cause the subject to experience any difference in its ability to move. As such, the patient associated identifier is dimensioned such that its size does not hinder the ability of the subject to physical move. In certain embodiments, the patient associated identifier has a small size; where in certain embodiments the patient associated identifier occupies a volume of space of about 5 cm$^3$ or less, such as about 3 cm$^3$ or less, including about 1 cm$^3$ or less.

The patient associated identifiers of interest include both external and implantable devices. In external embodiments, the patient associated identifier is ex vivo, by which is meant that the patient associated identifier is present outside of the body during use. Where the identifiers (for example signal broadcasters and/or receivers) are external, they may be configured in any convenient manner, where in certain embodiments they are configured to be associated with a desirable skin location. As such, in certain embodiments the external patient associated identifiers are configured to be contacted with a topical skin location of a subject. Configurations of interest include, but are not limited to: patches, wrist bands, belts, etc. For instance, a watch or belt worn externally and equipped with suitable receiving electrodes can be used as signal receivers in accordance with one embodiment of the present invention. The patient associated identifiers may provide a further communication path via which collected data can be extracted by a patient or health care practitioner. For instance, an implanted collector may include conventional RF circuitry (operating for example in the 405-MHz medical device band) with which a practitioner can communicate, e.g., using a data retrieval device, such as a wand as is known in the art. Where the patient associated identifier includes an external component, that component may have output devices for providing feedback, e.g., audio and/or visual feedback; examples of which include audible alarms, LEDs, display screens, or the like. The external component may also include an interface port via which the component can be connected to a computer for reading out data stored therein. By further example, the patient associated identifier could be positioned by a harness that is worn outside the body and has one or more electrodes that attach to the skin at different locations. The inventive construct can be linked to a portable device, for example a watch that has one or two electrodes dispersed on the wrist. There are many places where such a receiving electrode system could be placed and created such as on hearing aids that beep, a necklace, a belt, shoes (PZT-powered), eyeglasses, or earrings. In these external embodiments, a portion of the patient associated identifier, e.g., electrode, contacts the skin in a manner such that a communication line (such as a conductive communication line) that includes the patient's body may be established between the identifier and a fluid delivery device during use of the system.

In certain embodiments, the external patient associated identifier includes miniaturized electronics which are integrated with the electrodes to form an adhesive bandage style patch (e.g. a BANDAID™ style patch) with electrodes that, when applied, contact the skin. This configuration may further include a battery. The adhesive bandage style patch may be configured to be positioned on a desirable target skin site of the subject, e.g., on the chest, back, side of the torso, etc. In these embodiments, the circuitry of the patch may be configured to receive signals from devices inside of the subject, e.g., from an identifier of a pharma-informatics enabled pharmaceutical composition, and then relay this information to an external processing device, e.g., a PDA, smartphone, etc. Adhesive bandage style devices that may be readily adapted for use in the present systems include, but are not limited to: those described in U.S. Pat. No. 6,315,719 and the like.

In certain embodiments, the patient associated identifier (e.g., signal broadcaster and/or receiver) is an implantable component. By implantable is meant that the signal receiver is designed, i.e., configured, for implantation into a patient, e.g., on a semi-permanent or permanent basis. In these embodiments, the signal receiver is in vivo during use. By implantable is meant that the patient associated identifiers are configured to maintain functionality when present in a physiological environment, including a high salt, high humidity environment found inside of a body, for two or more days, such as about one week or longer, about four weeks or longer, about six months or longer, about one year or longer, e.g., about five years or longer. In certain embodiments, the implantable circuits are configured to maintain functionality when implanted at a physiological site for a period ranging from about one to about eighty years or longer, such as from about five to about seventy years or longer, and including for a period ranging from about ten to about fifty years or longer.

For implantable embodiments, the identifiers may have any convenient shape, including but not limited to: capsule-shaped, disc-shaped, etc. One way to achieve the small size is by including a rechargeable battery. Because this is not a life-support device, but rather a sensing and/or information transmission device, embodiments of the device have a natural life of two weeks, and recharge automatically off of coils in the patient's bed so that the device may be constantly recharging. The patient associated identifier may be configured to be placed in a number of different locations, e.g., the abdomen, small of the back, shoulder (e.g., where implantable pulse generators are placed) etc.

In addition to being configured to participate in transmission of a signal between the patient associated identifier and a fluid delivery device using the patient's body as a conduction medium, the patient associated identifier may further include one or more distinct physiological parameter sensing abilities. By physiological parameter sensing ability is meant a capability of sensing a physiological parameter or biomarker, such as, but not limited to: heart rate, respiration rate, temperature, pressure, chemical composition of fluid, e.g., analyte detection in blood, fluid state, blood flow rate, accelerometer motion data, IEGM (intra cardiac electrogram) data, etc. Where the patient associated identifier has physiological parameter or biomarker sensing capability, the number of distinct parameters or biomarkers that the signal receiver may sense may vary, e.g., one or more, two or more, three or more, four or more, five or more, ten or more, etc. The term "biomarker" refers to an anatomic, physiologic, biochemical, or molecular parameter associated with the presence and severity of specific disease states. Biomarkers are detectable and measurable by a variety of methods including physical examination, laboratory assays and medical imaging. Depending on the particular embodiment, the signal receiver may accomplish one or more of these sensing functions using the signal receiving element, e.g., using electrodes of the receiver for signal receiving and sensing applications, or the signal receiver may include one or more distinct sensing elements that are different from the signal receiving element. The number of distinct sensing elements that may be present on (or at least coupled to) the signal receiver may vary, and may be one or more, two or more, three or more, four or more, five or more, ten or more, etc.

The patient associated identifier may have any convenient power source, which could either be a primary cell or rechargeable battery, or one that is powered by broadcasting inductively to a coil, or even a photoelectric or other power source, as may be appropriate for the identifier given its site of association with the patient (such as topical or internal) and expected operating conditions.

Parenteral Fluid Delivery Device

The parenteral fluid delivery device is a device that delivers a quantity of a fluid (such as a gas or liquid) to a patient by a route other than the digestive tract, e.g., via a pulmonary route, via intramuscular injection, via intravenous delivery, etc. For purposes of describing the present invention, pulmonary administration is considered to be parenteral administration because delivery is via the lungs, even though entry to the lungs is via the mouth and/or nasal passages. As such, parenteral fluid delivery devices include syringes, intravenous systems, infusion pumps, dialysis systems, ventilators, anesthesia machines, nebulizers/inhalers, etc. The delivery device will include a fluid transfer signal generator, e.g., in the form of an integrated circuit or other suitable structure, that transmits a signal to a receiver upon transfer of fluid to the patient. In certain situations, the parenteral fluid delivery device is one that provides for one way transfer of fluid from the device to the patient. Examples of such devices are syringes, intravenous delivery devices and inhalers. In certain situations, the parenteral fluid delivery device provides for removal of fluid from a patient and the delivery of fluid to the patient. An example of such a device is a dialysis device.

One type of fluid that may be transferred to the patient is a liquid. The liquid may vary greatly in composition, and may include one or more distinct beneficial agents in a liquid pharmaceutically acceptable vehicle, e.g., one or more pharmaceutical agents, or may be a beneficial agent in its own right, e.g., such as where the liquid is a plasma volume expander.

For parenteral delivery of a liquid, the delivery device may vary. One type of device of interest is a syringe or analogous structure, e.g., that is configured for intramuscular injection of the liquid. Also of interest are intravenous administration devices, which may include a liquid storage element, e.g., a fluid containment or IV bag, a fluid metering unit or pump, a drip bag, etc. Another type of fluid transfer event that may be monitored by the systems of the invention is where fluid, e.g., blood, dialysate, etc., is transferred from a patient to an external device and then transferred back from the device to the patient, typically after some type of processing in the device. An example of a parenteral fluid delivery device that finds use in these situations is a dialysis machine, where such devices may be parenteral dialysis devices or hemodialysis devices, etc. Another type of fluid of interest is a gas. A variety of different beneficial agents are delivered in aerosolized format (which is a type of gas) to patients, where devices configured for such delivery are generally referred to as inhalers. As such, embodiments of parenteral delivery devices of the invention are inhalers.

A given fluid delivery device may include a single component or two or more disparate components (such as syringes and vials, fluid containment bags and IV pumps, etc.) which are operatively connected to one another during use and collectively comprise the ability to transfer a fluid transfer signal between the device and a patient associated identifier, as reviewed above. As such, the various components of the systems may further include communication elements, e.g., broadcasters and/or receivers, as may be required or desired for a given embodiment of the system. Such components may further include power sources, as may be desired, where any convenient power source may be present, including those mentioned above in connection with the patient associated identifier.

Embodiments of the fluid delivery devices may include what is viewed as pharma-informatics enabled components, such as pharma-informatics enabled fluid containers. By pharma-informatics enabled fluid container is meant a fluid container, e.g., bag, vial, etc., that includes a volume of fluid that is to be transferred to a patient, e.g., via the fluid delivery device, where the container also has associated with it some identifier that provides identifying information about the contents of the container. The nature of the identifying information may vary greatly, from the simple, e.g., the name of the fluid, the name of the pharmaceutical agent present therein, to the more complex, e.g., the dosage present in the container, the history of the fluid in the container, the quality of the fluid in the container (e.g., whether it is compromised or spoiled), etc. The nature of the identifier may also vary, e.g., from being a passive interrogatable element, such as a barcode or other machine readable identifier, to a more active component, such as a component that can broadcast information and includes a power source. Sensors, as described below, may also be associated with the medical containers.

Where a given system includes two or more different fluid containers, the system may be configured as a multiplex system. Embodiments of the multiplex system are configured to sufficiently reduce or eliminate cross-talk and confusion between various broadcast signals of multiple components of the multiplex system such that a given fluid transfer signal about a given fluid and a patient may be properly matched up or associated with each other. For example, a signal generated about a first IV bag may be distinguishable from a signal generated about a second bag, where distinguishable signals may be provided in a number of different ways, e.g., by using an appropriate time-based communication protocol, by having signals of different frequencies, etc. Of interest are the signal protocols described in PCT/US2006/016370 filed on Apr. 28, 2006, the disclosure of which is herein incorporated by reference. In certain embodiments where multiple different fluid containers are present in a given fluid delivery system, the different fluids may be color coded to provide an additional distinguishing feature, where this color coding may be detected and transmitted to the patient associated identifier (for example as part of a fluid transfer signal) for further confirmation that the right medicine is being delivered to the right patient.

In certain embodiments, a given fluid delivery system may include both a pharmacological agent and an amount of an "antidote" for that agent should the system identify, e.g., through physiological sensing during delivery, such as may occur during real-time applications, that the patient is adversely reacting to the pharmacological agent. In such embodiments, delivery of the agent may be automatically stopped, and delivery of the antidote may be automatically commenced, as automatically directed by the system without any human intervention.

Additional System Components

As detailed below, certain embodiments are characterized in that the patient associated identifier and/or the fluid delivery device further transmits a signal to and/or receives a signal from an additional external component. The external component is, in certain embodiments, an external processing component, such that it is designed to accept data, perform prescribed mathematical and/or logical operations, and output the results of these operations. Examples of external components of interest include, but are not limited to: a healthcare provider network (such as a hospital information system (HIS); a home healthcare information system, etc). Accordingly, systems of the invention may further include an external processor component, such as a HIS or analogous system that includes various aspects of a patient specific data, such as prescriptions, treatment regimens, health history, dosage guidelines, etc. This data may include information obtained from an electronic medication storage unit, e.g., a PYXIS™ storage unit, etc.

The systems may further include various sensors. Physiological sensors may be associated with the patient, and may or may not be part of the patient associated identifier. Physiological sensors of interest include, but are not limited to: heart rate sensors, breathing sensors, temperature sensors, etc., as described more fully above in connection with the patient associated identifier.

Sensors may also be associated with various components of the fluid delivery system. Sensors may be associated with fluid containers, e.g., to detect a color-coded liquid therein, to detect clarity of a fluid, to detect the presence of one or more analytes in the fluid, etc. Sensors may also be present in tubing components of the system, e.g., to detect proxies of bacterial infection, such as turbidity, etc.

Fluid Transfer Signal

As reviewed above, the system is configured to transfer a fluid transfer signal between the patient associated identifier and the fluid delivery device, where the signal is transferred between these two components using the patient's body as a signal conduction medium. The physical nature of the signal may vary, e.g., where physical types of signals of interest include electric, magnetic, optical, thermal, acoustic, etc. Because the fluid transfer signal is transferred between the two components using the patient's body as a conduction medium, fluid communication is established between the parenteral fluid delivery device and the patient prior to transmission of the fluid transfer signal.

The content of the fluid transfer signal may vary depending on the particular application in which the methods and systems are employed, where the content may range from simple to complex, depending on the particular type of application, e.g., prospective, real-time or historical, the direction, e.g., to and/or from the patient associated identifier, etc. A given fluid transfer signal provides prospective information about a fluid transfer event if the fluid transfer event is a future fluid transfer event, i.e., the fluid transfer event has not yet occurred. A given fluid transfer signal provides real-time information about a fluid transfer event if the fluid transfer event is a currently occurring fluid transfer event, i.e., the fluid transfer is currently happening. A given fluid transfer signal provides retrospective information about a fluid transfer event if the fluid transfer event is a past fluid transfer event, i.e., the fluid transfer event has already occurred.

In certain embodiments, the content of the fluid transfer signal is that a fluid connection has been established between the fluid delivery device (including disparate components thereof) and the patient. In certain embodiments, the content of the fluid transfer signal is that a previously established fluid connection between the fluid delivery device (including disparate components thereof) and the patient has been interrupted. In addition to an indication that a fluid connection has been established, the fluid transfer signal may include additional content, e.g., where additional content of interest includes, but is not limited to: patient specific content, fluid specific content, delivery device specific content, etc.

Patient specific content of interest includes, but is not limited to: identity of patient (such as name, unique identifier), general information about the patient, e.g., gender, age, race, etc., health history of patient, health status of patient, including one or more sensed physiological parameters, which may or may not be combined into a health indicative marker, e.g., a wellness marker or index, and the like.

Fluid specific content of interest includes, but is not limited to: identity of the fluid, the contents of the fluid, the identity of one or more pharmacological agents in the fluid, the concentrations of such agents in the fluid, the history of the fluid, e.g., where manufactured, how stored, the quality of the fluid, e.g., whether compromised or not, etc. Also of interest is fluid container specific content, which content includes, but is not limited to: the source/history of the container, the identity of the container, e.g., general (e.g., type, such as bag) or specific (e.g., serial no.), etc.

Device specific content of interest includes, but is not limited to: the state of the device (for example whether the device on or off), the settings of the device, e.g., flow rates, the source/history of the device, etc.

In certain embodiments, the fluid transfer signal includes information that an actual fluid transfer event has occurred between a parenteral fluid delivery device and a patient. In such embodiments, the fluid transfer signal provides information about whether fluid has been transferred between the parenteral delivery device and the patient. The fluid transfer signal is one that provides for actual knowledge that fluid has been parenterally transferred from the device to the patient.

Embodiments of the invention include delivery devices that are configured to transmit the fluid transfer signal only when fluid is delivered from the device to the patient and in a manner such that transmission of the signal can only occur when the device actually contacts the patient and fluid is transferred to the patient. As such, the system is distinguished from other systems which provide for generation of a signal when a package is opened, or other proxy-type signals for actual administration of the fluid. Instead, the system of the invention provides a signal that provides knowledge that delivery of the fluid to the patient actually occurred, e.g., by only transmitting the signal when the device touches the patient and fluid enters the patient from the device. While the fluid transfer signal may be transmitted between the parenteral fluid delivery device and the patient associated identifier using any convenient protocol, in certain embodiments protocols that ensure transmission only occurs upon contact of the device with the patient are employed. One such protocol of interest is conductive transmission, e.g., where the body is employed as a conductive medium between the fluid delivery device and the patient associated identifier to provide for transmission of the signal. Accordingly, a given fluid transfer signal may include qualitative or quantitative information. Qualitative information is information that is not tied to specific numerical values or units, and includes but is not limited to: identifying information, quality control information about a fluid (for example age, storage conditions, etc.), information about a patient, e.g., how patient is responding, etc., whether something is or is not present, etc. Quantitative information is information that includes numerical values or units, and includes but is not limited to dosage information, etc.

Communication Between System Components

As reviewed above, communication of the fluid transfer signal between the patient associated identifier and the fluid delivery device employs the patient's body as a conductive medium. One or more additional and separate communication lines may be established between various components of the system, such as between the patient associated identifier and an external component, such as a hospital information system, between components of a fluid delivery device, such as an infusion pump and a fluid container, between the fluid delivery device and the hospital information system, etc. These additional communication lines may be wired or wireless communication lines, as desired, employing traditional physical connections, such as wires, optical fibers, etc., or wireless communication protocols, e.g., RFID, etc. These additional communication lines may be employed to transfer information and/or power between the different device components. For example, disparate components of a fluid delivery system may include communications components that are powered via wireless transmission of power from one element to another. These additional communication lines are, in certain embodiments, non-conductive communication lines.

Prospective Applications

As indicated above, certain applications of the systems are prospective applications, in that the system is employed prospectively to evaluate a fluid transfer event (such as delivery of a fluid dosage to a patient), where the fluid transfer event has yet to actually occur. Such applications include situations where the system is employed as a check to ensure that a given dosage of a fluid is properly matched with a patient. In addition to this simple check, the system can also ensure that the dosage to be delivered is appropriate. If a proper match is detected between the patient and the fluid transfer event of interest, the system can be configured to automatically enable the fluid transfer event to occur, e.g., by activating the fluid delivery device, such as the pump. Alternatively, where a proper match between a patient and a given fluid transfer event is not detected, the system can be configured to disable the fluid transfer event, e.g., by inactivating the fluid delivery device, etc. Where desired, the systems of the invention are configured to provide an error signal upon detection of an error in a parenteral administration event. The detected error may vary greatly, and examples include situations where the patient associated identifier has knowledge of medicines that should not be administered to the patient and the identity of a medicine is transmitted to the receiver. In addition, the system may be configured to provide tight control over administration of what are known in the art as "high-alert medications," such that the system is configured to only enable administration of such medications in predetermined dosage ranges and provides error signal upon deviation from such ranges. Accordingly, the system finds use with what are known in the art as "high-alert" medications." Classes/Categories of such medications are: adrenergic agonists, IV (such as epinephrine); adrenergic antagonists, IV (such as propranolol); anesthetic agents, general, inhaled and IV (such as propofol); cardioplegic solutions; chemotherapeutic agents, parenteral and oral; dextrose, hypertonic, 20% or greater; dialysis solutions, peritoneal and hemodialysis; epidural or intrathecal medications; glycoprotein IIb/IIIa inhibitors (such as eptifibatide); hypoglycemics, oral; inotropic medications, IV (such as digoxin, milrinone); liposomal forms of drugs (such as liposomal amphotericin B); moderate sedation agents, IV (such as midazolam); moderate sedation agents, oral, for children (such as chloral hydrate); narcotics/opiates, IV and oral (including liquid concentrates; immediate- and sustained-release formulations); neuromuscular blocking agents (such as succinylcholine); radiocontrast agents, IV; thrombolytics/fibrinolytics, IV (such as tenecteplase); and total parenteral nutrition solutions. Specific "high-alert medications" include: amiodarone, IV; colchicine injection; heparin, low molecular weight, injection; heparin, unfractionated, IV; insulin, subcutaneous and IV; lidocaine, IV; magnesium sulfate, injection; methotrexate; nesiritide; nitroprusside sodium, injection; potassium chloride concentrate, injection; potassium phosphates, injection; sodium chloride injection, hypertonic (more than 0.9% concentration); and warfarin. The signal may also vary greatly, including an audible alarm, an alarm signal sent to a physician, etc. Such embodiments include methods where the system is monitored for the occurrence of the error signal.

In such applications, a processor is conveniently employed to match patient specific information and fluid transfer event specific information, e.g., to determine whether or not to allow the fluid transfer event to occur, to produce an error signal, etc. The location of this processor may vary within the components of the system, as desired. As such, in certain embodiments, the processor may be located in the patient associated identifier. In certain other embodiments, the processor may be located in the fluid delivery device. In yet other embodiments, the processor may be located in the hospital information system.

Real-Time Applications

As indicated above, certain applications of the systems are real-time applications, in that the system is employed to evaluate a fluid transfer event (such as delivery of a fluid dosage to a patient) while the fluid transfer event is actually occurring, i.e., is in progress. For example, the system can be used to monitor the patient for an adverse reaction during delivery of the fluid, e.g., by monitoring physiological parameters of the patient. If monitored physiological parameters vary from acceptable predetermined ranges, the system can be configured to produce an error signal, e.g., as described above, and or take action, e.g., stop delivery of the medication, administer an antidote, etc.

Historical Applications

Also of interest are uses of the systems and methods for historical applications, such that the systems are employed to obtain a true and correct record of fluid transfer events that have actually occurred between a patient and a fluid delivery device. Historical applications are any applications that use information which includes knowledge that a fluid transfer event has actually occurred. Where desired, the systems of the invention are configured to provide an error signal upon detection of an error in a parenteral administration event. One example of such an application is where, during a given fluid transfer event, the transfer of fluid is interrupted. The system may be configured to generate a signal indicative of such an interruption, which could be manifested as an alarm, etc. The detected error may vary greatly, and examples include situations where the receiver has knowledge of medicines that should not be administered to the patient and the identity of a medicine is transmitted to the receiver. Another example of an administration error that may be detected includes situations where the receiver can detect the occurrence of an adverse reaction, e.g., by monitoring physiological parameters of the patient. The signal may also vary greatly, including an audible alarm, an alarm signal sent to a physician, etc. Such embodiments include methods where the system is monitored for the occurrence of the error signal.

True and accurate records of fluid transfer events also find use in providing health care practitioners or other individuals with accurate treatment records for a given patient. As such, historical applications include employing the fluid transfer event data in further treatment of an individual, e.g., developing future treatment regimens and/or modifying existing treatment regiments.

Additional historical applications of interest include employing the fluid transfer event data for invoicing purposes, e.g., so that patients are accurately, billed for medications and/or services that they actually receive, etc.

Specific Illustrative Embodiments of the Methods and Systems

Aspects of the invention having been described in general terms above, additional details in the context of specific embodiments are now provided.

Embodiments of the smart therapeutics system can include a beneficial agent with a chip. The chip can contain information about the type of beneficial agent to be administered to the patient. Upon extracting the beneficial agent from the holding container, e.g., a vial, a signal can be sent from the vial to a chip within the syringe. The broadcasted signal can indicate the type of beneficial agent extracted from the vial. Upon injection into the patient, the information can be sent from the syringe to an information management database located in, on, or near the patient, e.g., the patient associated identifier. The system can also notify the receiver about any therapies the patient is undergoing, such as dialysis. In this case, the dialysis machine, or an add-on module added to current dialysis machines, can be used to collect and transmit data about the dialysis being performed and parameters of the blood going out of and in to the patient during dialysis. Upon successful detection and decoding of the transmitted signal, the receiver can activate an alert to let the nurse or other attending person and/or the patient that the receiver has successfully received information about the medication or therapy which was administered.

In one embodiment of the present invention, FIG. 1 represents a smart therapeutics system with syringe 1 (a parenteral delivery device). Syringe 1 includes needle 2, fluid containment component 8 and plunger 6. As is common in the relevant art, syringes are usually used once then thrown away, e.g., because of blood borne contaminants, etc. Shown in syringe 1 is chip 3, which chip has transmission ability in that it can transmit or broadcast a signal. The medicine, which is usually in vial 5, is often used just once also. Frequently, vials of medicine are shipped separately from the syringe. During treatment, syringe 1 can be filled with medicine from vial 5 and injected into the patient.

In certain embodiments, when syringe 1 enters vial 5, chip 7 within vial 5 begins to broadcast the name of the medicine or a number that encodes the medicine. Chip 3 within syringe 1 begins to "listen" for the signal broadcasted by chip 7 when fluid enters into syringe 1. Chip 3 located in syringe 1 can record the broadcasted signal.

In one embodiment of the present invention, when the medicine is injected into the patient (such that fluid is transferred to the patient from the device), chip 3 in syringe 1 broadcasts the encoded number through syringe 1. For example, the broadcasting embodiment may be a coaxial transmitter with two conductors transmitting the encoded number into the patient. The encoded number may be picked up by a receiver located in, on, or around the patient. The encoded number is an example of a qualitative fluid transfer signal.

In an additional embodiment of the present invention, the broadcasting embodiment can also be a coil embedded in syringe 1 with one or more wires attached to chip 3. The power source can also have a coil on it. The fluid going into syringe 1 can activate the power source in syringe 1. The activated power source can energize the coil on the power source. The coil on the power source can electrically conduct with the coil attached to chip 3, essentially acting as an RFID interface. Activating the power source is not limited to electrical conduction but could be accomplished through other techniques, for example, proximity conduction. In this manner, a fluid transfer signal that is dependent on actual injection of fluid is transmitted.

In an additional embodiment of the present invention, multiple modes of communication between the broadcasting unit in syringe 1 and the receiving unit located on the patient are possible. For example, communication between the broadcasting unit in syringe 1 and the receiving unit located on the patient can be accomplished through conduction patterns, a RF type of coil system or an antenna system.

There are several methods available to identify the type of beneficial agent in vial 5. In one embodiment of the present invention, the beneficial agent can be identified by detecting change in impedance, inductance, or capacitance of the beneficial agent as it is drawn into syringe 1. This change can be encoded in chip 7 and transferred to chip 3. When chip 3 receives the encoded signal, the broadcasting embodiment in syringe 1 begins broadcasting to the receiving unit located in, on or around the patient.

In one embodiment of the present invention, syringe 1 can contain chip 3 and each chip 3 may be identical. For example, chip 3 within syringe 1 may only contain a writable receiving unit. Chip 3 in syringe 1 receives and stores the encoded signal from chip 7 in vial 5. Chip 3 in syringe 1 relays the encoded signal to the broadcasting unit in syringe 1. The broadcasted signal is picked up by a receiver in, on, or around the body. As used herein the term "chip" means processing element, e.g., and may be an integrate circuit (IC).

On the other hand, chip 7 in vial 5 may be unique. For example, each chip may broadcast a different encoded signal depending on the contents of the vial.

In another embodiment of the smart parenteral delivery system, the encoded data is stored in, on, or around the patient. By having the receive unit in, on, or around the patient, the receive computer can be the hub for the information management system.

Consequently, no other receive units are required. For example, a smart parenteral receive system may consist of any syringe and vial containing send and receive chips and a receive unit (such as a patient associated identifier) associated with the patient, e.g., located in, on, or around the patient. Prior inventions include procedures that require manual input of data such as the scanning of bar codes and manual recording of the amount and time when the medicine was administered. Such steps are not required in these embodiments of the present invention.

Figure 2:
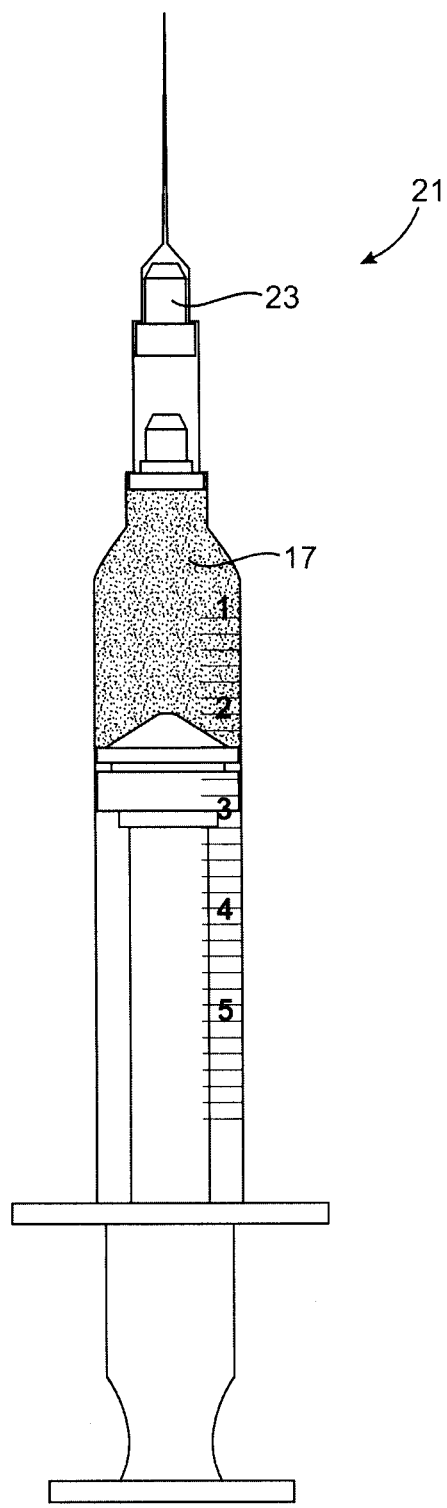
FIG. 2 illustrates a smart therapeutics system that signals the type of beneficial agent released from a pre-loaded syringe.

FIG. 2 illustrates the implementation of another embodiment of a smart parenteral delivery system. Syringe 21 already contains beneficial agent 17. Chip 23 is embedded in pre-loaded syringe 21. The broadcasting unit broadcasts the encoded signal when the beneficial agent is injected into the patient to a receiving unit located in, on, or around the patient. The broadcasting unit can be similar to that described in FIG. 1.

In an additional embodiment of the present invention, the smart therapeutics system can record how much fluid is withdrawn from the vial and ultimately delivered to the patient. In certain embodiments this includes having a coil that is fixed at one end of the syringe and then another coil that rests on the plunger. As the plunger is pushed, the mutual inductance between the two coils changes and the position over time of the plunger can be determined. In another embodiment of the invention, two conductive strips are embedded into the vial wall and a conductor on the plunger. As the plunger is pressed, the impedance between the two strips on the vial wall change as the conductive strips capacitively couple between the conductors on the plunger. The impedance can be measured and the amount of fluid withdrawn can be determined. In another embodiment of the invention, a direct impedance measurement of the fluid is performed to determine the amount of fluid withdrawn. Similarly, a capacitive measurement of the plunger versus the plate at the bottom of the system is used in certain embodiments to determine the amount of fluid withdrawn. The above discussion provides examples of quantitative fluid transfer signals.

In an additional embodiment of the system, a light or some other type of indicator, e.g. a green light, flashes when the encoded signal is delivered to the patient's receive system (patient associated identifier) from the broadcasting chip. This alerts the administrator to withdraw the syringe from the patient. The indicator would alert the administrator that the encoded signal has been sent and the medicine has successfully been delivered.

Figure 3:
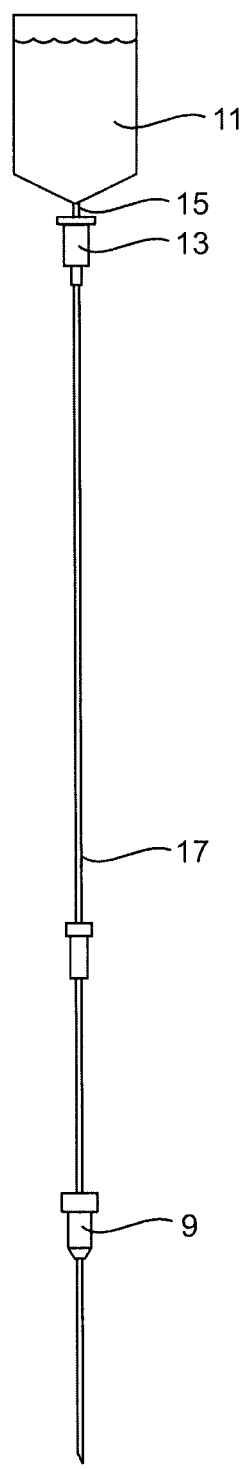
FIGS. 3 to 7D illustrate various embodiments of an intravenous administration system that signals the type of beneficial agent released from an IV.

FIG. 3 illustrates another embodiment of the invention, which is the implementation of a smart therapeutics system to detect medicine administered through IV bags. Chip 15 located in bag 11 is pre-coded with the type and amount of the beneficial agent. As fluid flows by outlet 13, chip 15 in bag 11 begins transmitting the encoded signal. Chip 9 embedded in IV 17 can detect the encoded signal and broadcast the information to a receiving unit located in, on, or around the patient. The broadcasting unit, located in IV 17, can be similar to that described in FIG. 1.

Figure 4:
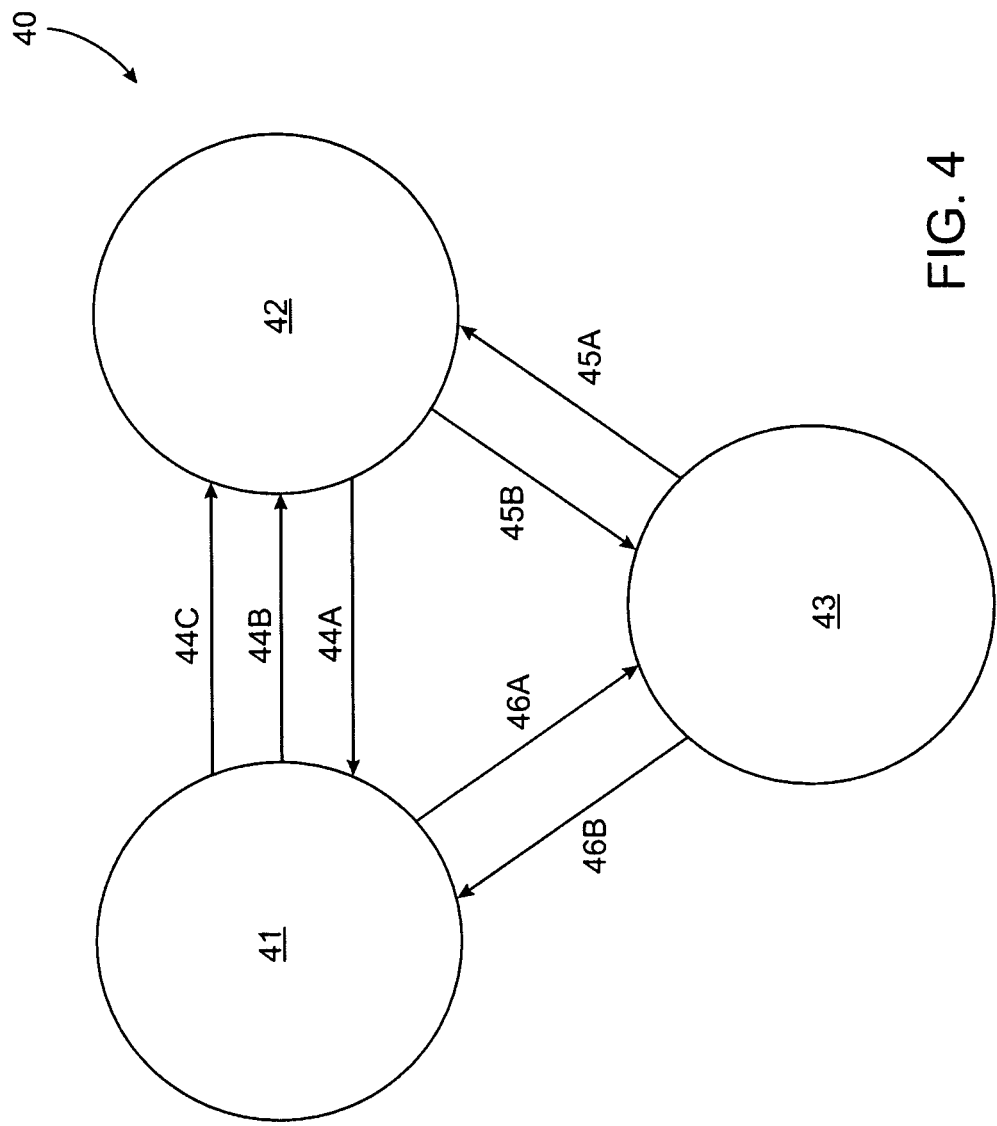

A schematic diagram of a smart fluid delivery system according to an embodiment of the invention is depicted in FIG. 4. In FIG. 4, system 40 includes patient associated identifier 41, parenteral fluid delivery device 42 (such as IV delivery system, syringe, inhaler, dialysis machine), and health care provider network (such as an HIS) 43. Each of elements 41 and 42 includes an identifier element that can receive and broadcast a signal. In the embodiment shown in FIG. 4, arrow 44A shows the transmission of a fluid transfer signal from fluid delivery device 42 to patient associated identifier 41, where the content of the fluid transfer signal is the notification to the patient associated identifier that the device is about to transfer fluid to the patient. Arrow 44B shows the transfer of information from patient associated identifier 41 to fluid delivery device 42 in response to the notification, where the content of this signal is approval to the device to begin administration, e.g., because the fluid delivery event and patient identifying information match, e.g., as described above. Also shown is arrow 44C which depicts the transfer of information from patient associated identifier 41 to drug delivery device 42 after a fluid transfer event has commenced, where the content of the information is that a sensed parameter(s) of the patient indicates that the patient is not responding well and that the device should stop administering the fluid. Alternatively, the information could be that the patient is responding well and that administration may continue. This signal can be limited to an error signal provided to a health care practitioner, or be a signal that actively stops the fluid delivery device from delivering fluid.

Also shown in FIG. 4 is arrow 46A which represents the transfer of information from patient associated identifier 41 to HIS 43. The content of the information transferred in arrow 46A is medication and response history, such that information about the nature of the medication(s) that have been delivered to the patient and the response history of the patient, e.g., in the context of measured physiological parameters over time, such as heart rate over time, etc., is transferred from the identifier to the HIS. Also shown is arrow 46B which represents the transfer of information from HIS 43 to identifier 41, where the content of this information is the patient prescription information, such that the identifier knows which prescriptions are to be implemented by fluid delivery device 43.

Also shown in FIG. 4 is the transfer of information between fluid delivery device 42 and HIS 43, represented by arrows 45A and 45B. Arrow 45A represents the transfer of information from device 42 to HIS 43, where the content of this information may be usage and performance data of the fluid delivery device, e.g., whether the device stopped working for a given period of time, how long the device administered fluid to the patient, etc. Arrow 45B represents the transfer of information from HIS 43 to device 42, where the content of the information may be fluid delivery parameters, such as permitted drugs or drug combinations for a given patient, permitted dosage ranges for a given drug or combination of drugs, as well as other operating parameters or guidelines that constrain the operation of the delivery device.

At least one of the communication lines between identifier 41 and device 42 is one in which the patient's body is employed as a fluid conduction medium. Other of the communication lines shown in FIG. 4 may be wireless, include a relay station, etc., as desired.

Of note in the embodiment shown in FIG. 4 is the absence of a human intervention component. As such, human intervention is not required for the disparate components to communicate with each other and provide for the prospective safeguards as well as historical dosage information provided by the system.

Figure 5A:
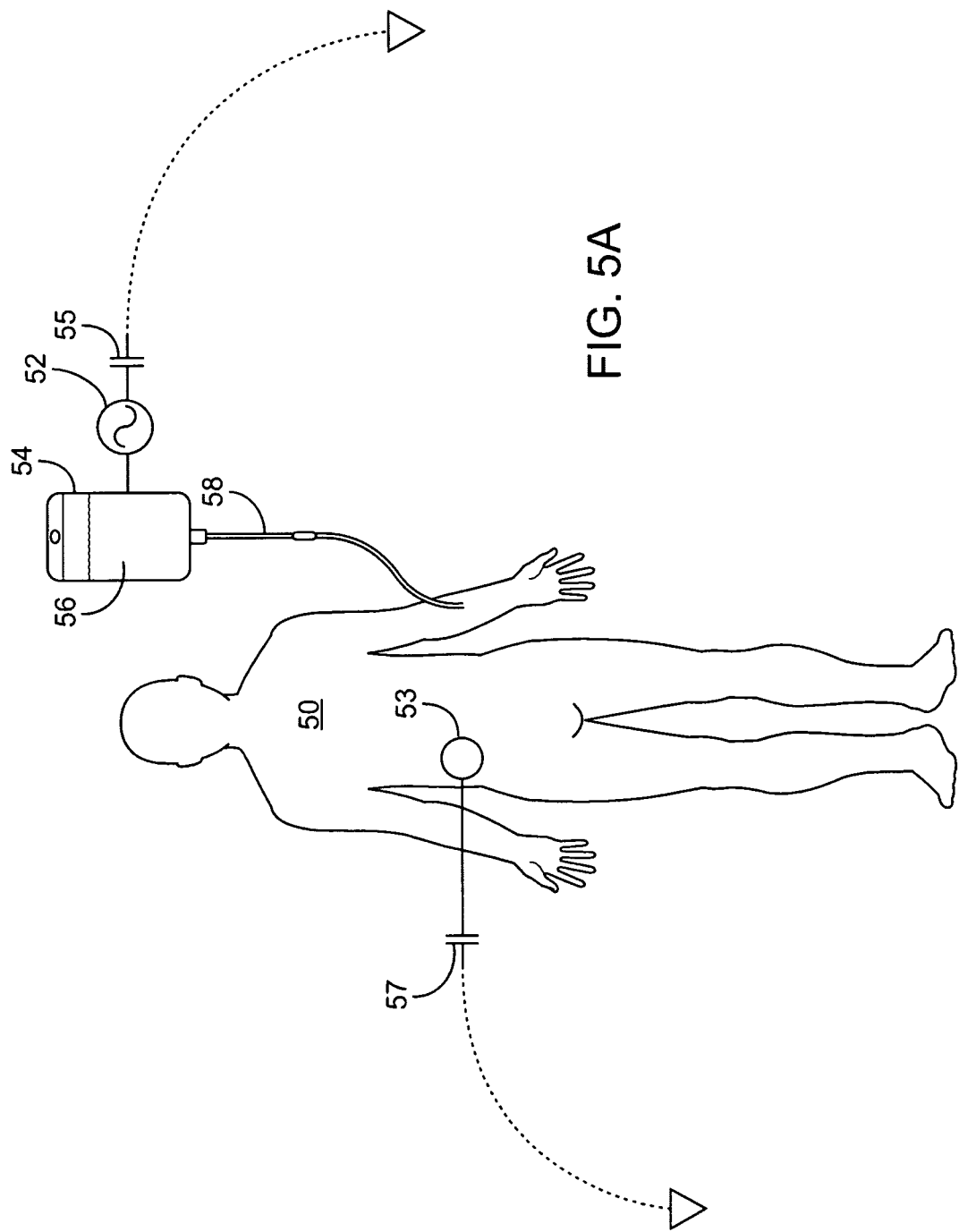

Another embodiment of the invention that finds use for keeping track of when IV bags are attached to and delivered to a patient is described below in connection with FIGS. 5A to 7D. As shown in FIG. 5A, a transmitter 52 is attached to the IV bag 54 or the IV set, which is anything connected to the IV bag, and a receiver 53 is implanted in the patient. When the IV bag is not connected to the patient, the receiver 53 cannot detect the transmitter 52 transmitting from the IV bag 54. But when the IV bag 54 is infusing fluid, or there is a fluid connection between the IV bag 54 and the receiver 53 via the patient 50 acting as a conducting bridge, or at least attached to the arm in anticipation of delivery of fluid from the IV bag 54 to the patient, then a signal is transmitted by the IV bag 54 and received by the receiver 53.

In this system, the transmitter capacitively couples a signal to the fluid. That signal transmits through the fluid and to the patient, through the patient's body, and to the receiver, specifically one electrode of the receiver (thereby making up one side of the conductive loop). The other side of the conductive loop includes the other side of the transmitter, which capacitively couples a signal to ground, i.e. everything surrounding a patient which is not attached to the patient. The ground may be chairs, tables, the floor, etc. The signal goes through the ground and then is capacitively coupled to the other side of the patch receiver, thereby completing the loop. This capacitive coupling on either side to ground is illustrated in the FIG. 5A by capacitors and dashed arrows 55 and 57, respectively.

Referring to FIG. 5A, starting at transmitter 52, the signal goes through the bag 54, which is the container or IV bag, and is capacitively coupled through the IV bag. Then the signal progresses to the fluid in the IV bag 56 through the IV tube 58, through the patient's arm, or a vein somewhere in the body, e.g., arm, leg or elsewhere in the body. The signal continues to go through the body and goes to the receiver 53. On the other side of the receiver, to give a differential signal, is a capacitive coupling 57 between the receiver housing and the ground. The conductive loop continues back through the ground and then back up through the capacitive coupling 55 from the ground to the broadcaster which is attached to the IV bag.

The fluid transfer signal may be a high frequency signal, e.g., between 1 and 10 MHz, and may be higher, e.g., 100 MHz or more, e.g., 1 GHz or more. The frequency is in a range such that the receiver only picks up the signal when the IV bag is connected to the body, and not just by the electromagnetic waves that are emitted by the broadcaster. In certain embodiments, the frequency is chosen based on the considerations that the higher the frequency, the easier it is to couple it directly to the IV bag, but the more likely it is that the signal will be picked up by the receiver regardless of whether the IV bag is connected to the body.

In certain embodiments, the fluid transfer signal also encodes a number, either through phase shift keying, or through frequency shift keying, or one of any other convenient telecommunications technique.

In a variation of the above embodiment, one may have multiple IV bags attached to the patient. Each of these IV bags has its own broadcaster, and each of them is encoded with a different encoded number. The IV bags may all be broadcasting on the same frequency, or they might be broadcasting on different frequencies, or in different frequency bands. Where desired, the systems can be time multiplexed or they can be frequency multiplexed. For example, the signals broadcast by the disparate components of a system may all be in the same frequency, and time multiplexing is employed (for example randomly associated), so that the disparate components are all broadcasting at least occasionally at a different point in time so that their signals can be distinguished from another.

By doing this, the receiver detects the signal from each of the IV bags, and knows when they are attached and when fluid is flowing from the bags into the patient. The system is configured, in certain embodiments, to determine when fluid is not flowing, or when it is interrupted. The system is configured, in certain embodiments, to measure the time and duration of infusion. As reviewed above, systems of the invention may be configured such that alarms are produced, whenever for example, the wrong bag is connected to the patient, or when the delivery is interrupted for any reason and fluid is no longer dripping through, or when a patient takes some other type of medication which would not be compatible with the medications delivered by the IV bag. The above discussion provides an example of a system configured to detect an error event and provide a reporting signal of the same. As such, the receiver may not only be measuring the medications delivered by the IV bag, but it may also be detecting when a person takes a pill, or breathes fluid from an inhaler, or is being dialyzed through a dialysis machine for kidney function, or for any of the other purposes where medical therapeutic elements are being administered to the patient.

Figure 5B:
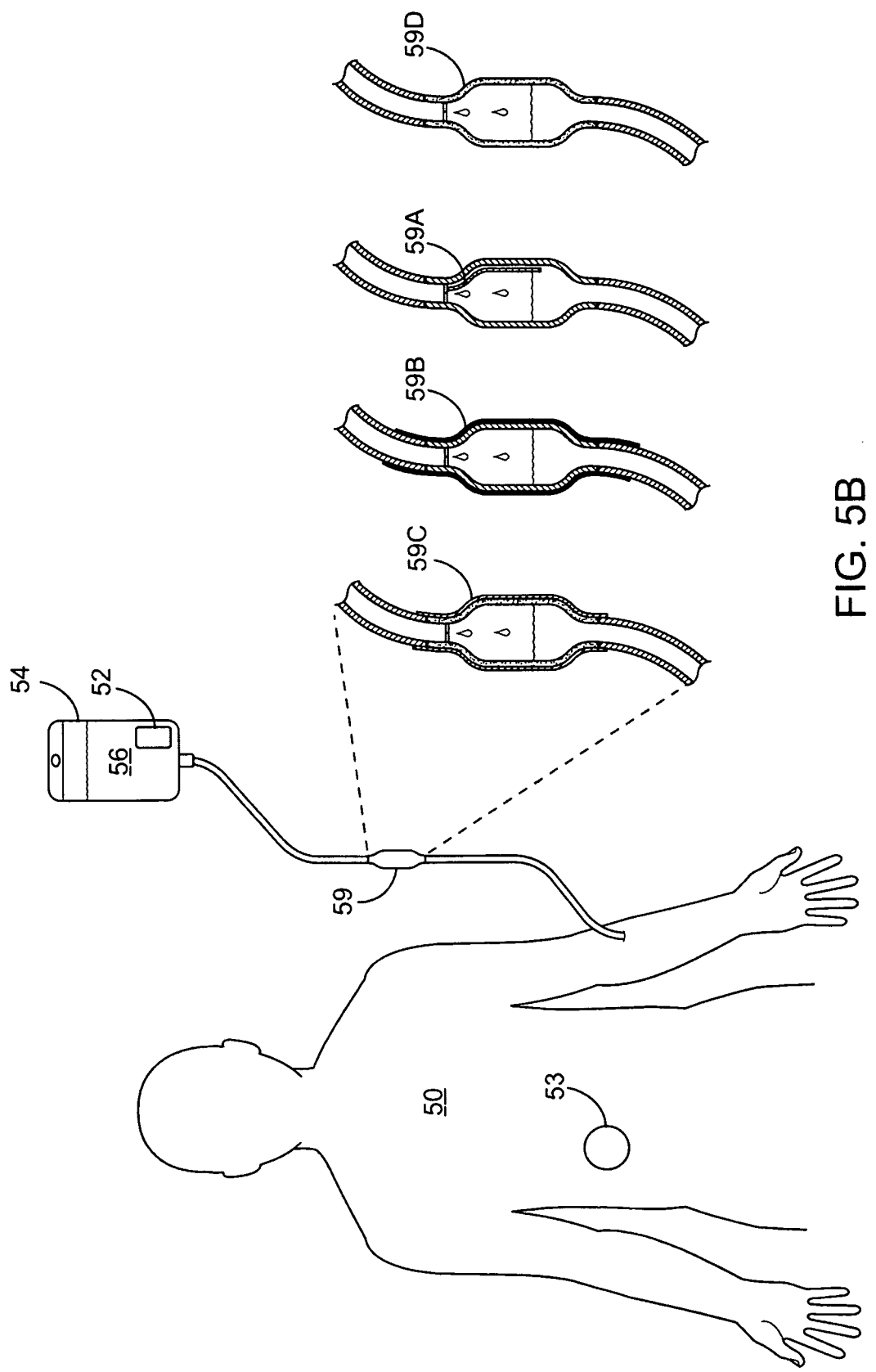

In certain embodiments, the IV bag sets will have a drip carrier where the fluid drips from one point to another, e.g., as illustrated in FIG. 5B. Where desired, a conductor, or a capacitive conductor, from one side of the drip to the other may be provided in order to provide a fluid communication between the fluid delivery device and a patient associated identifier. In these embodiments, a broadcaster can be placed down stream, i.e., closer to the patient than the drip carrier, so that the signal is not interrupted by the drip device.

Alternatively, as shown in FIG. 5B, a conductive element may be placed between the bag 54 with the broadcaster 52 and the patient 50 side of the drip carrier. As shown in FIG. 5B, IV bag 54 includes broadcaster 52. IV bag 54 is connected to patient 50 via drip bag 59. Because of drip bag 59, the direct fluid communication between the bag and the patient associated identifier 53 of patient 50 is broken. To provide for the communication between IV bag 54 and patient associated identifier 53, a conductive element may be provided between the inlet and outlet of drip bag 59. The communication element may vary greatly, from a fluid wetted line 59A, such as a nylon line, to a metallic coating 59B or strip 59C on the drip bag, etc.

Alternatively, one or more of the components of the IV system may be fabricated from conductive materials, e.g., drip bag component 59D, such as conductive plastics, that provide for the conductive link between the patient associated identifier 53 and the disparate components of the IV or other delivery system. In these embodiments, establishment of a fluid connection between the body and the fluid delivery device can work with or without liquids in the lines. As such, the system could be employed for $O_2$ lines. In such embodiments, the entire system can be electronically checked for all connections made to a patient, not just those for medications, but also feeding, urinary and gaseous tubes, as well.

In certain embodiments, the IV bag is filled with a first fluid, such as saline. A nurse or other health practitioner injects a medicine into the IV bag, and then that combination is administered to the patient. In this situation, the vial containing the injected medicine is configured to transfer a signal to the syringe, and the syringe is configured to receive and record the signal, such that the syringe is receiver enabled itself. The syringe then broadcasts the signal to the IV bag, the IV bag receives the signal, and modifies the code it will broadcast to the patient associated identifier based on what was delivered and injected into the bag by the syringe. The signal broadcast to the patient associated identifier would thus be a different number that would reflect this additional medication.

Figure 6:
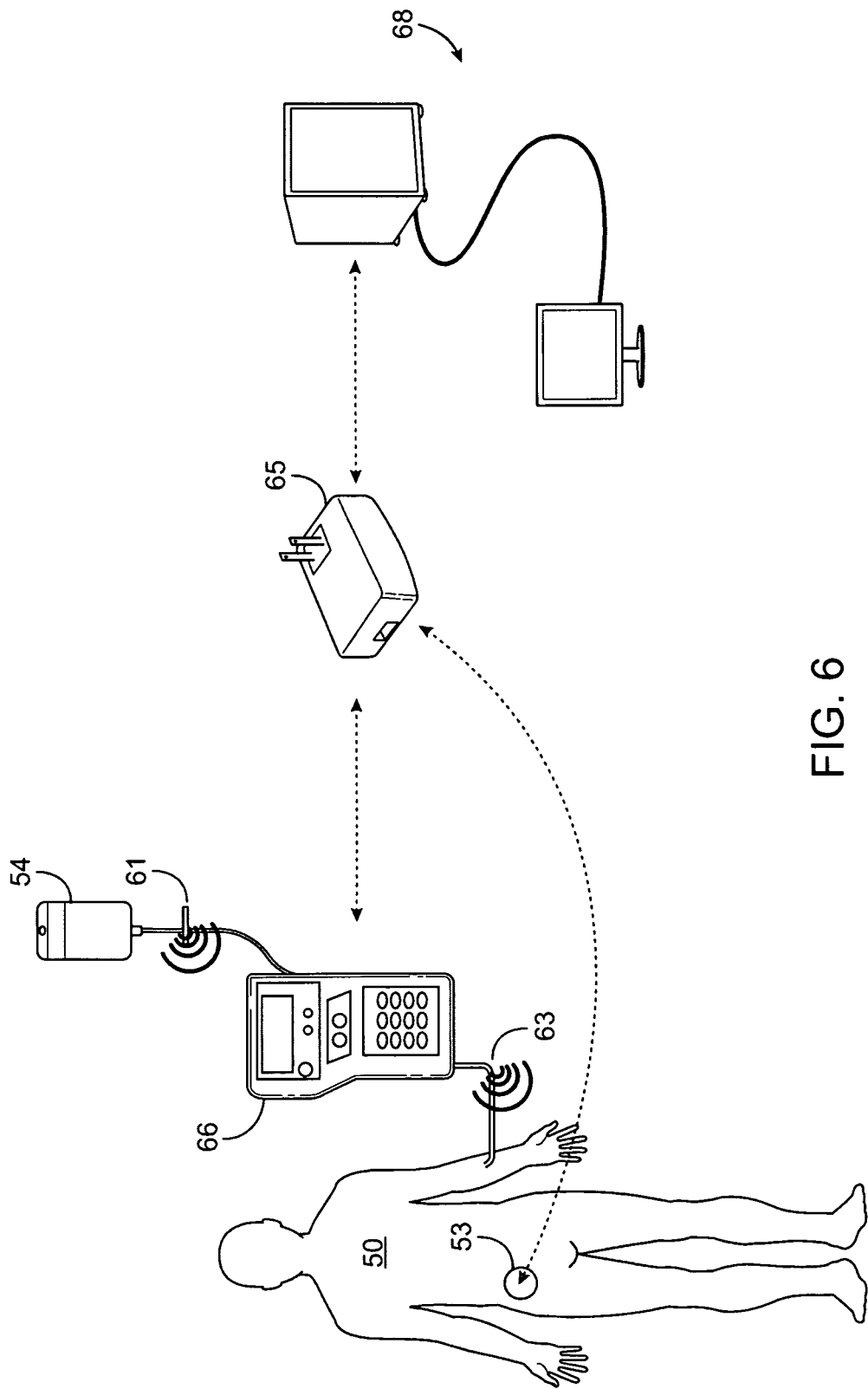

Another variation of this system is where there are two separate links. One of multiple IV bags going into a fluid processing unit, e.g., pump, which may be a combining pump, and then a separate link between the processing unit and the patient. Referring to FIG. 6, there can be two different transconduction links. A first transconduction link 61 goes from the IV bag 54 into the IV pump 66, and then a second transconduction link 63 between the IV pump 66 and the patient 50. If, for example, there are any processing or filtering, or additional chemicals at the IV pump, a different signal may be transmitted to the body which is distinct from the signal transmitted from the IV bags. For example, if there are two different IV bags that are being mixed by the pump, and delivered immediately after being mixed, each of them would be broadcasting identifying information about one of the solutions to the IV pump, and a different signal reflecting that combination being administered to the patient would be broadcast from the pump 66 to the patient associated identifier 53.

Still referring to FIG. 6, the entire system is depicted, where the patient associated identifier 53 broadcasts via an RF link to one or more external devices, e.g., a network of relay stations 65, handheld devices, etc. This can be the data that has been gathered over time, or immediately following reception of delivery data. The data may be further communicated, e.g., via an RF link to a relay station, which then may be further communicated, e.g., through either an RF link or a conductive path link such as a cable or any other type of telecommunication link to an external processing component 68, such as a HIS within the hospital or care facility. Then this information is processed and output, e.g., recorded to a physical recordable medium, displayed to a user, etc., such as displayed to a nurse or other medical practitioner.

Where desired, the external processor 68 can provide various alerts. For example, an IV bag may have bar codes on it for shipping and receiving purposes, and also for providing information to be transferred before the contents of the bag are administered to the patient. For example, a given medical fluid container with fluid may be bar coded and entered into the HIS. The prescription for a given patient with respect to that medical fluid container may also be entered into the HIS, and that prescription may be downloaded into the patient's patient associated identifier, e.g., through an RF link. In addition, the same information may be downloaded, for example to the IV pump that is being used to deliver the fluid inside the container to the patient.

The IV pump only permits delivery after two confirmations occur. First, the pump confirms with the patient associated identifier that the correct medication is going to be administered to the patient, as determined by the bar code and the patient associate identifier. After transmitting through the conductive link to the patient that this is the correct fluid, the system continues to allow a full delivery of fluid. For example, in the initial setup the IV pump fluid is primed and is introduced to the patient long enough for the conductive signal to be transmitted from the IV bag to the patient associated identifier. The patient associated identifier then responds by confirming that the fluid is being delivered, and confirming that the fluid being delivered is the right fluid. The system then continues to deliver the fluid to the patient. If, however, the system detects during this step that the fluid is not the right fluid, the pump is alerted to stop pumping. This is an example of a double confirmation system embodiment of the invention. The advantage of this type of embodiment is if there is an RFID tag or a bar code system on the bag and the bag is brought to the patient's room, one can know the bag is in the room, but will not know that the bag is being attached to the patient or delivered to the correct patient, instead of the fluid being delivered to the patient next door or simply sitting in the room and not attached to anybody. The RFID and the barcodes are a way to keep track of this product between the factory and the patient, and the transconduction link of the present invention confirms the delivery of the medication to this patient and not to some generic patient or the drain. Another use of the system is to prevent fraud, where the systems of the invention may be employed to make sure that medications are actually being delivered to patients and not discarded.

In certain embodiments the receiver includes physiologic sensors that are also making measurements of a patient's health status, e.g., heart rate, breathing rate, temperature, activity level. If the sensors detect something that is not expected, or dangerous, the system is configured, in certain embodiments, to send an alert (such as an error signal) through a convenient communications link, such as an RF link, to the network or relay station and through the information server system through the nurse's station. In some embodiments, it may also shut down the pump. For example, if the pump is delivering a pain medication, and the breathing rate starts to go lower than it should, the pump might be automatically shut down. In certain embodiments, the system could further include a type of medication that reverses the action of a pain medication, such as enabling the restarting of the person's heart if it stopped. Alternatively, there may be a defibrillator patch that is always applied to a patient, so just in case too much medicine is delivered, the system can automatically deliver a defibrillation signal that would restart a patient's heart if necessary. Other measures could also be provided. For example, the medication that is causing the trouble could be stopped. Other medications that could theoretically counteract the adverse reaction, e.g., restart the heart such as adrenaline may be administered, for example a small drip of adrenaline could be automatically started. This might be useful in places where there are a lot of patients, but not a lot of nurses or other medical practitioners to keep track of them.

In other embodiments, the receiver can activate an alert when the signal is successfully detected and decoded. This configuration provides the healthcare provider and/or patient with an indication that the medication and therapy monitoring system is working properly.

Other possible methods for indicating that the signal has been received include an audible sound, such as a beep, or a vibration. The receiver can optionally send an RF signal to a personal data assistant or other external device alerting the nurse that the drug delivery signal was successfully received by the receiver.

In some embodiments, an indicator which would only be detectable by the patient may be used. For example, in the case of a receiver in the form of an implantable unit or external skin patch, a piezoelectric vibration may occur when the signal is successfully received. Alternatively, an electrical stimulation can be administered, causing a tingling feeling in the patient.

Figure 8:
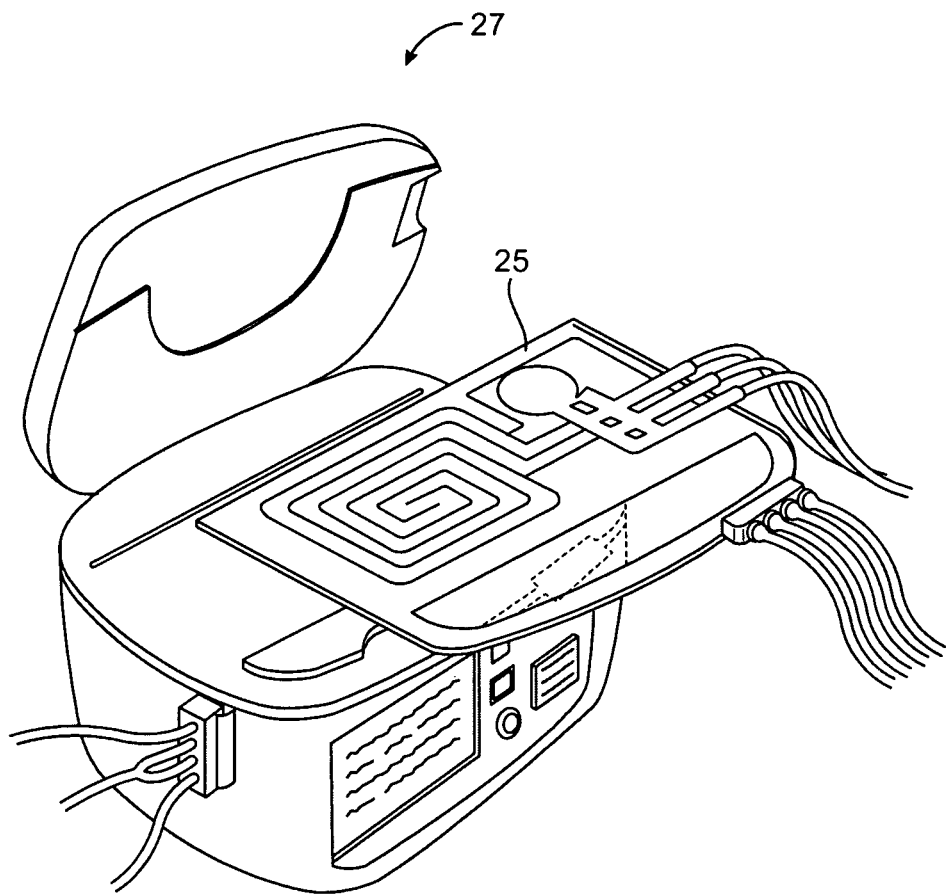
FIG. 8 illustrates a dialysis machine which can be equipped with an embodiment of the smart therapeutics system.

The above description of error monitoring is not limited to IV parenteral delivery devices, but is also applicable to inhalers, pills, pumps, dialysis machines, and other parenteral delivery devices. The same system could also be used for a dialysis system, where instead of an infusion pump, the external device is a dialysis machine, e.g., as depicted in FIG. 8. In this application, a number of things could be monitored. With additional electrodes placed on the person's arm, one could keep track of the hydraulic impedance of the vein while the dialysis is occurring. With this embodiment, one can know whether the veins are collapsing, for example. This is a very important parameter when performing a dialysis for a patient. One can also keep track of other things flowing into and out of the body, such as the composition of the fluid, the chemistries of the fluid, etc. This information can be combined with a lot of other features that are typical of a dialysis machine. In certain embodiments, one measures the impedance of the arm, and the impedance of the vein through the arm, as the fluid is being delivered to the arm, in addition to other measurements that the dialysis machine typically makes.

Figure 7A:
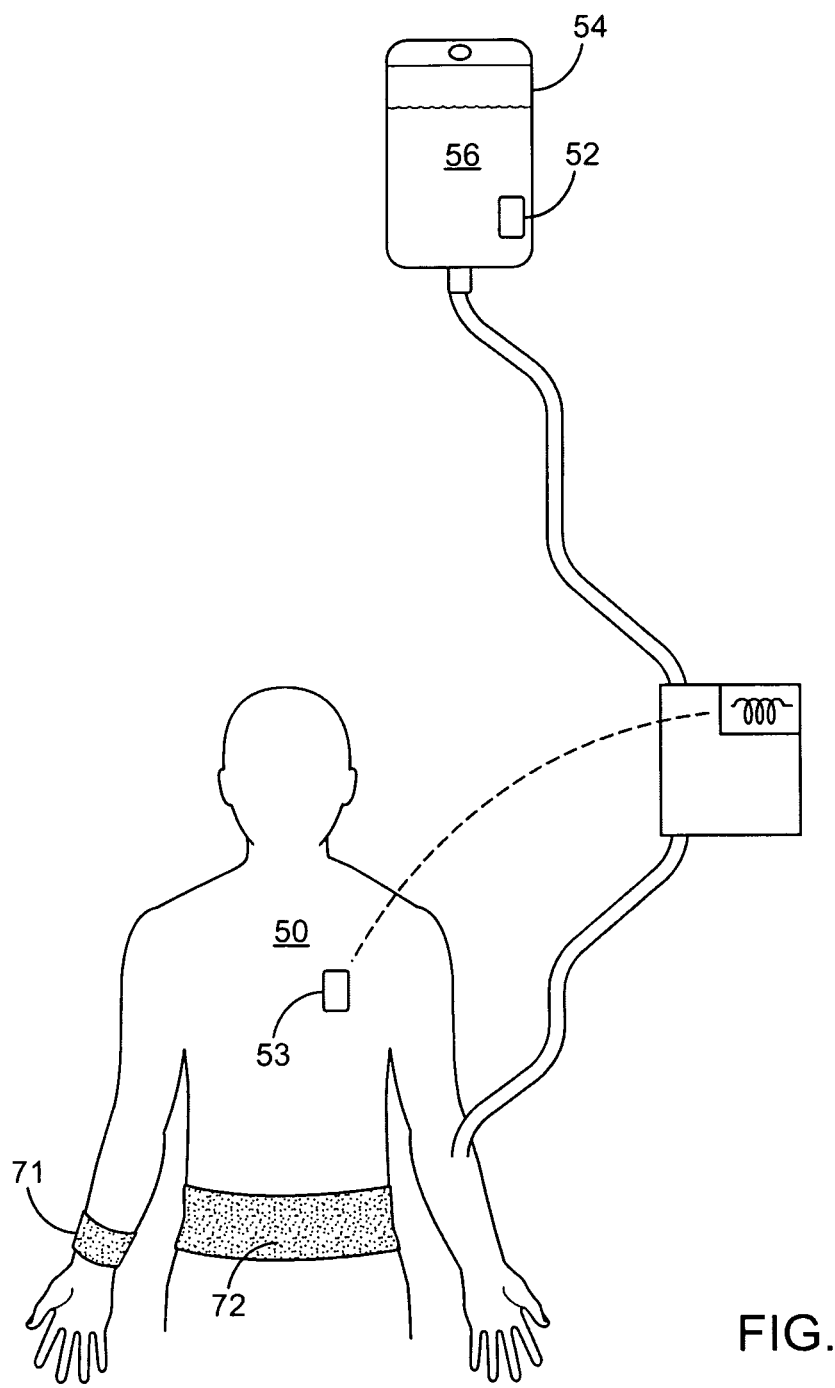

Referring to FIG. 7A, there is another version of the embodiments described above. The embodiment shown in FIG. 7A does not require the use of the ground plane, and works with implants as well as patches. But, it does require another conductor between the IV pump or the IV bag and the patient, such as an ankle strap, wrist strap 71, or some other conductor. While the patient is being infused, they are given a wrist strap 71, e.g., on the opposite hand of the patient. Alternatively, the conductor could be an article of clothing, or part of the patient's gown. The gown could be electrified, so that the patient is wearing threads that are somewhat conductive. The second conductor may be another article of clothing, such as a belt 72 or a bracelet. The second conductor does not have to be in direct contact with the patient, it just has to be in loose contact.

In that configuration, the current flow is between the IV bag 54 (or pump if included) and the fluid, and the fluid goes into the person's body. On the opposite side of the pump is a wire which would go to the article of clothing, or a bracelet or some other embodiment of the second conductor. That becomes the current loop path which is then picked up by the body and patient associated identifier associated therewith. The article of clothing could be something like a garment that the patient is always wearing in the hospital that has some sort of electric threads in it, and that is essentially a ground loop that goes around the person's body. That configuration provides the capacitive coupling to the skin, and provides sufficient differential current that the patient associated identifier picks up the signal. Alternatively, it could be part of the bed, where one could have a conductor in the bed, and every bed has some electrified element, so whenever one has the IV pump, one would clamp to the bed frame, and the bed frame becomes the conductor.

Figure 7B:
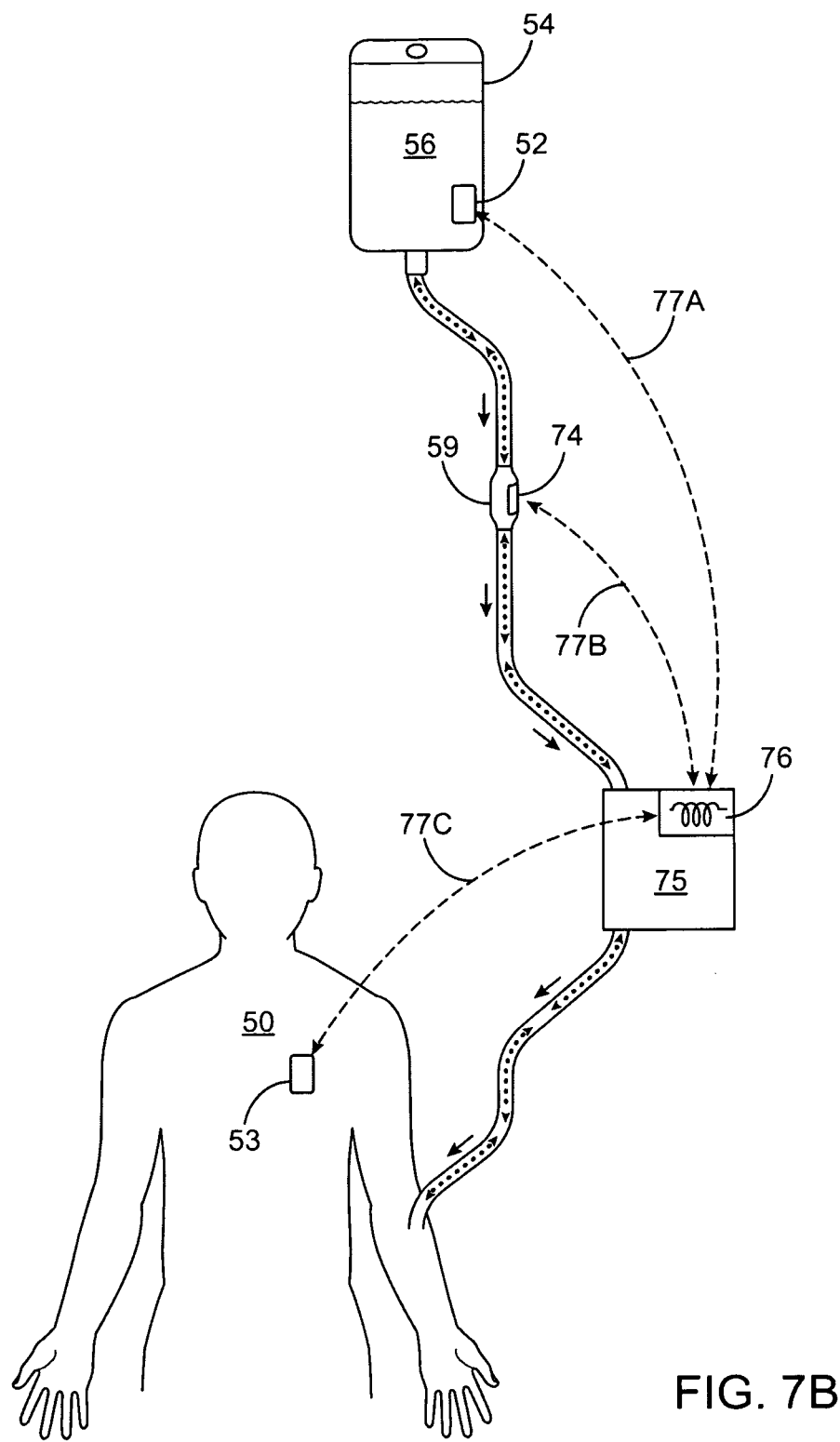

In certain embodiments, such as that shown in FIG. 7B, a hybrid communication protocol, such as a hybrid RFID protocol, is employed. In the embodiment shown in FIG. 7B, each component of the delivery system, e.g., the IV bag 54, the drip bag 59, and the pump 75 have a broadcaster (52, 74 and 76 respectively) that communicates in the system to provide knowledge that the component is present, hooked up correctly, etc. A fluid based connection (i.e., "fluvius link") between the components of the delivery system and the patient associated identifier 53 is established and shown in the figures as dots running through the fluid line between bag 56 and the patient 50. Also shown are wireless communication lines 77A, 77B and 77C, between the different broadcasters of the delivery system components. The disparate broadcasters of the components may be powered using any convenient approach, such as batteries, coils, photovoltaic cells, etc.

In certain embodiments, the broadcasters are powered by coils arranged in various formats. In certain embodiments one may have two coils-one on the transmitter on the bag and one on the infusion pump, and energy is wirelessly sent from the pump to the transmitter on the bag to power the bag transmitter. In a variation of this embodiment, the coil for the bag transmitter is a detachable part that is attached to the infusion pump via a cord and placed adjacent to the IV bag. For convenience, there may be a pouch on the IV bag to hold the coil, the coil may be adhered to the bag, e.g., with fabric hook-and-loop attachment elements (e.g. VELCRO™), or the IV bag may be placed into a pouch that incorporates the coil into it. This embodiment is shown in FIG. 7C. In the embodiment shown in FIG. 7C, the coil is a detachable part tethered to the pump 75. When a bag is used, the nurse places the coil into a pouch 73, placing the coil adjacent to the transmitter 52. Alternatively, the fabric hook-and-loop attachment elements could be used to place the coil on the bag or the bag is placed into a sleeve with the coil embedded. These variations improve the efficiency of the power transfer.

Figure 7D:
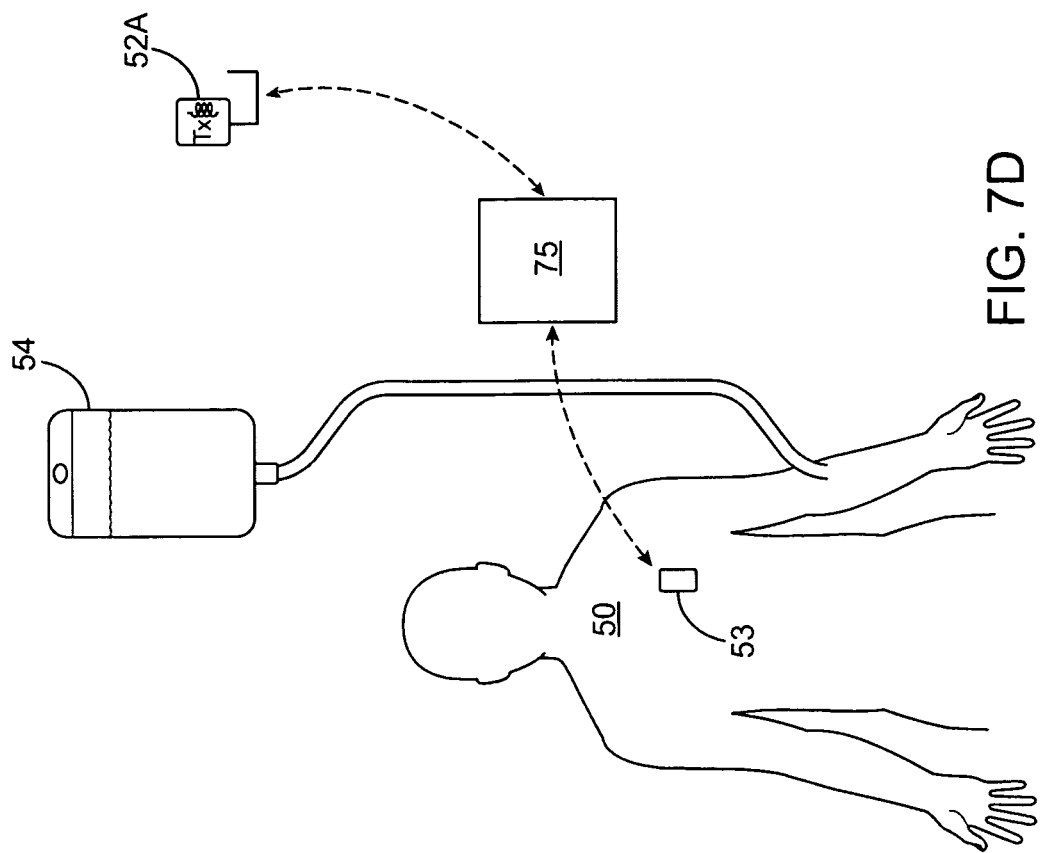
Figure 7C:
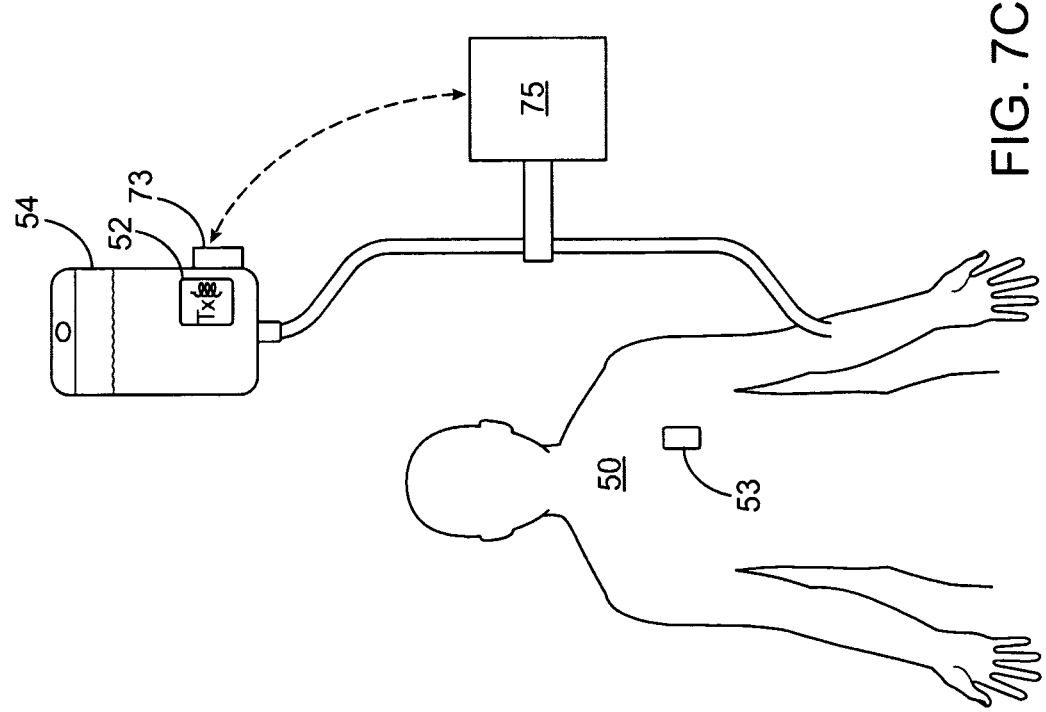

In yet another variation, shown in FIG. 7D, the transmitter 52A is off of the IV bag and the transmitter becomes an external module and it can either be wired and attached to the pump, or wireless (as shown by dashed line). In this embodiment, identification of the contents of the bag may be by a number of different ways, such as by bar code, text, RFID, etc. A reader reads either the bar code, the text or the RFID, where the reader may be a camera, a bar code reader, an RFID reader etc. Another alternative employs a capacitor plate incorporated into the construction of the bag and a simple connector that attaches the transmitter to the capacitor plate. The ID signal is transmitted through the drip line to the patient and the reader reads the signal and then transmits the ID wirelessly to the pump. As such, in the embodiment shown in FIG. 7D, the transmitter is a reusable part that communicates to the pump via wired or wireless communications. The transmitter identifies the IV bag based upon a machine readable tag embedded into the bag. The machine readable tag may be a bar code, printed text, RFID, etc. The transmitter includes appropriate hardware to read the tag, e.g., RFID reader, laser bar code reader, CMOS or CCD camera with appropriate software to read a bar code or perform an OCR function, etc. The transmitter and IV bag have features to position the transmitter adjacent to the machine readable tag and to place the transmitter's capacitor plate in intimate contact with the outside of the bag.

These features may include the fabric hook-and-loop attachment elements, a pouch on the side of the bag, or a sleeve incorporating the transmitter into which the bag is placed. The transmitter continues to transmit an ID through the IV drip to the body mounted receiver using capacitively coupled signals. Alternatively, the capacitive plate might be incorporated into the IV bag construction and a connector provided to attach the reusable transmitter.

In another embodiment of the smart parenteral delivery system, the encoded information can also be linked to an internet system. For example, not only does the patient's receive system pick up the information, but by using, for example a wireless technology standard for exchanging data over short distances (e.g. BLUETOOTH™ wireless communication protocol), the encoded information can be broadcasted in a hospital bedside monitor.

The bedside monitor relays the information to the internet and subsequently to the data base management system. As such, the patient's medical record is immediately updated and could be verified against the patient's health record so that if the administered medicine was incorrect, e.g., not prescribed, then an alert is notified and either a nursing staff member or if necessary some other staff member is notified to take action. In some instances it could be a life threatening issue and this could act as an alert process before any serious injuries occur.

In an additional embodiment of the present invention, the type of medication, amount, and time of use can be detected in an inhaler. Located on the inhaler are two electrodes that are placed above and below the mouth.

In one embodiment of the present invention, medicine can be delivered only when the patient is inhaling. Typically, the injected medicine is to be inhaled in a stream of air to insure that delivered gas ends up in the patient's lungs. The present invention can detect the patient's air stream. When the air stream is detected, the inhaler delivers the medicine.

In one embodiment of the present invention, there is a differential pressure sensor to detect whether the patient is inhaling when the medicine is injected. The delivery of the medicine can be timed to when the patient is inhaling, so that when the patient is inhaling properly the medicine is delivered. After delivery of the medicine, a signal that encodes the type of medicine and date of use is broadcasted through the contacts on the inhaler. The signal is picked up by the receiver located in, on, or around the patient.

In another embodiment of the present invention, other types of cues can be used to indicate whether the patient successfully administered the medicine. For example, an impedance measurement between the mouth and inhaler indicates whether there is proper contact between the mouth and the inhaler. If the patient does not have a proper seal in the mouth, then the medicine is not delivered.

If the medicine is not successfully administered, the receiver either does not transmit any code, or a code is transmitted that indicates no medicine was delivered, e.g., the patient tried but failed to inject the medicine. In this way, the doctor or appropriate staff member could determine whether the medicine was administered properly and take action to illustrate proper procedure in taking the medicine.

In an additional embodiment of the present invention, the amount of medicine injected by the inhaler can be quantified. For example, one of the bits of transferred information can represent how much medicine is delivered. The amount of medicine delivered can be measured in a number of ways. For example, pressure sensors can measure the volume of medicine remaining. In another example, an electronic valve can deliver a set amount of medicine while a counter keeps track of the number of times the valve is opened.

In another embodiment of the present invention, the inhaler can provide feedback to the patient to alert whether or not the medicine has been administered. For example, the inhaler can produce a visual or audio alert when the medicine has been properly administered.

In an additional embodiment, the smart parenteral delivery system can be extended to detect when dialysis is being performed and how the dialysis is being performed, e.g., in a kidney patient. Hemodialysis systems typically use two tubes with needles in the body of the patient. One tube removes blood from the patient and carries it to the dialyzer to be filtered, after which it is injected back into the patient through the other tube. FIG. 8 shows a hemodialysis machine, with disposable unit 25, which contains the filter, and hardware unit 27.

One or both of the needles in contact with the patient can be used as transmit electrodes to send a signal when dialysis is being performed. Using both needles to transmit, one will be the relative anode, while the other is the relative cathode. Each needle would cycle between anode and cathode, since it is an AC system. When dialysis is being performed, a signal can be transmitted which has a code specific to dialysis systems. This code can be detected and decoded by a receiver located in, on, or around the patient. The receiver can keep track of when dialysis is performed, how long it was performed for, and what settings were selected on the dialysis machine, such as flow rate.

A wealth of additional information can also be transmitted to the receiver during dialysis. For example, the flow rate of the blood coming out of the patient, and the flow rate of the filtered blood going back in to the patient can be measured and transmitted. The receiver can then monitor if there is a misbalance of fluid going in and out of the patient, and set off an alarm if that is detected.

The pressure at each location can be measured, thus giving an indication of the pressure drop. The pressures can be used to determine whether a vein is collapsing, which can be a serious problem for dialysis. The pressure at the receiver location can also be measured, and compared to the pressures at each needle to give a pressure drop. In some embodiments, if the measured pressure drop indicates that a vein is collapsing, the system can signal the dialysis machine to slow the flow rate or shut down completely to wait for the veins to open up. In some embodiments, the system may activate an alert that would notify the nurse or other healthcare provider of the problem.

Other parameters that may be measured in the blood going into and out of the patient include, but are not limited to, temperature, oxygenation levels, hematocrit, and conductivity. The conductivity can be an indication of how effective the dialysis treatment is. A broad array of chemical analyses can also be performed on the blood going into and out of the patient. Examples of measurements that can be taken include the levels of calcium, potassium, and creatinine present in the blood. All of this information can be sent to the receiver.

Information about the dialyzer used to perform the treatment, such as the make, model, and serial number of the dialyzer can also be transmitted. Some patients may not always receive dialysis treatments at the same location or with the same machine. If a problem comes up, it may be helpful to know the specific machine that has been used for each dialysis treatment, to see if there is a correlation.

In some embodiments, the parameter measurement and data transmission can be integrated into the dialysis machine itself.

In other embodiments, an add-on module can be utilized to provide the added functionality. In some such embodiments, the add-on module can open up, and the two dialysis tubes can be placed across it. Upon closing the module, a needle will puncture one or both tubes, allowing the blood to be sampled for analysis. The module can then perform a variety of analyses on the blood going into and out of the patient, as well as the difference between the two, as discussed above. The same needles can be used to transmit the data. The differential signal can be transmitted through the tubes and then through the body. The two tubes go to different locations in the body, providing a signal which can be easily picked up by the receiver.

In other embodiments, the smart therapeutics system can be incorporated into a peritoneal dialysis system, in which dialysis solution (dialysate) is placed into the body for a period of time to absorb waste products, then drained and discarded.

In some embodiments, the data measured by the smart dialysis system can be continuously transmitted to the receiver. In other embodiments, the data can be transmitted at select intervals, or at the beginning and/or end of the dialysis treatment.

For patients with kidney failure, in which dialysis is performed several times per week, the record that the dialysis was performed, and the data obtained during the procedure, can be very valuable to the physician.

Once the transmitted information is detected by the receiver, it becomes part of the patient's record along with the other information, such as medications the patient has received through swallowing a pill, an IV, a syringe, an inhaler, or other means. All of the data can be provided to the physician when uploaded from the receiver. This allows for any healthcare provider to have access to the patient's detailed medical records and a log of recorded treatments.

Circuitry

Figure 9A:
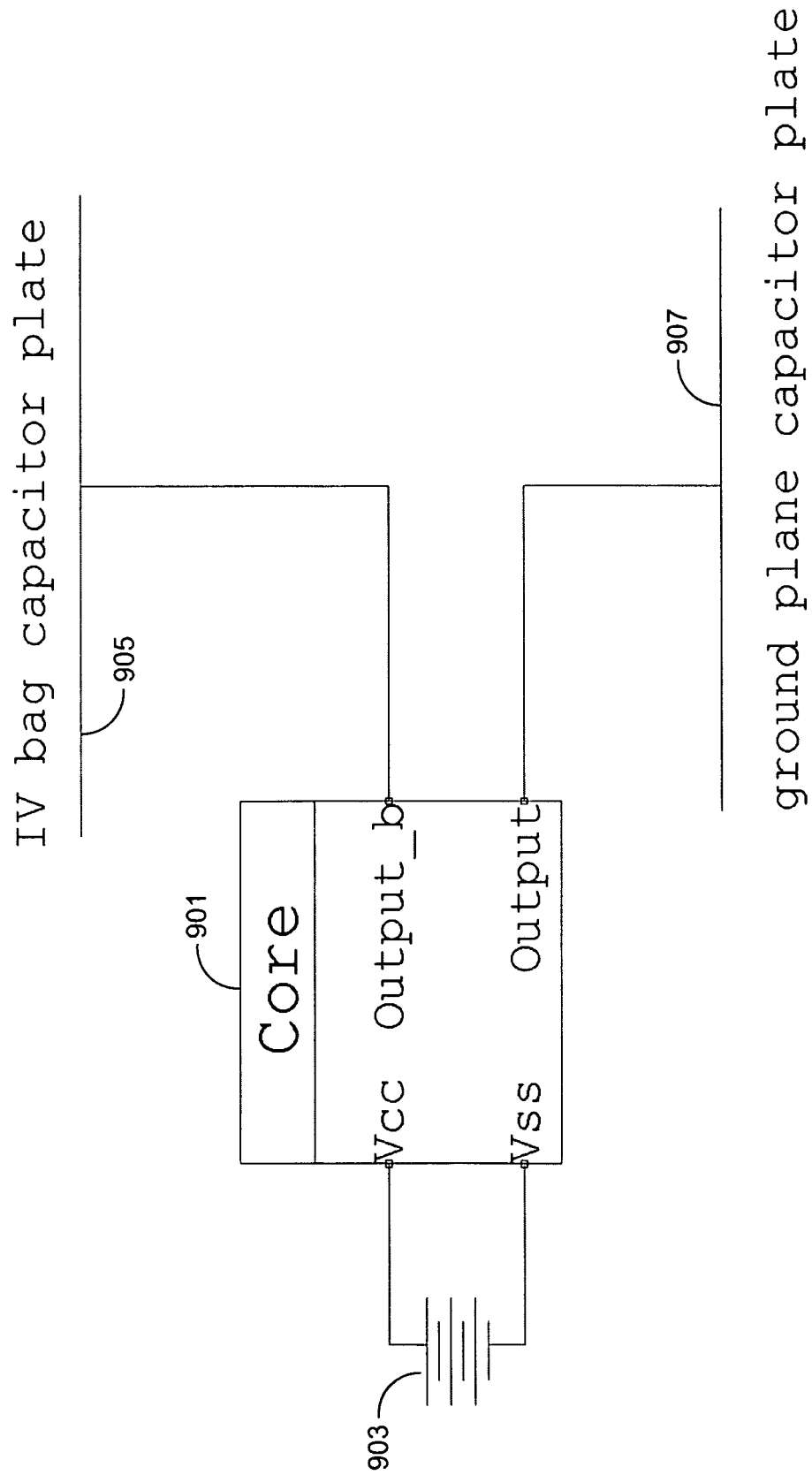
FIGS. 9A-9K depict an IV bag broadcast circuit in accordance with one embodiment of the invention.

FIG. 9A shows a top-level overview of one embodiment of the broadcaster circuit which can be used in association with an IV bag in accordance with embodiments of the invention. Chip 901 is powered by battery 903. Chip 901 controls the output signals going between IV bag capacitor plate 905 and ground plane capacitor plate 907. IV bag capacitor plate 905 can be made of a conductive material, such as a copper strip or printed ink, and attached to the IV bag, e.g., during manufacture or at the hospital. Methods of attaching the capacitive plate to the IV bag include an adhesive glue or direct printing of the conductor, among others. The ground plate can be placed anywhere that it can be electrically tied to earth ground.

Figure 9B:
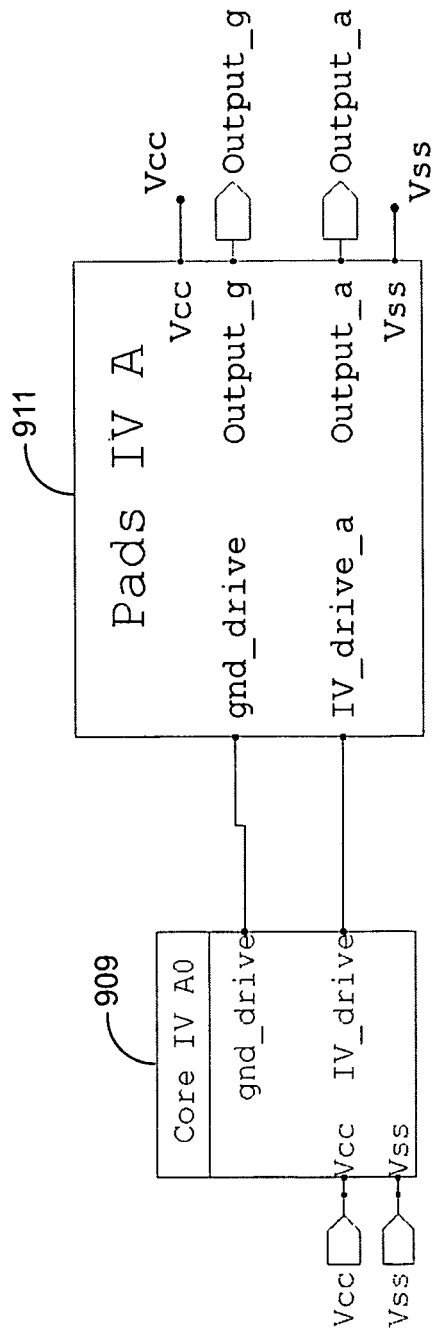
Figure 9C:
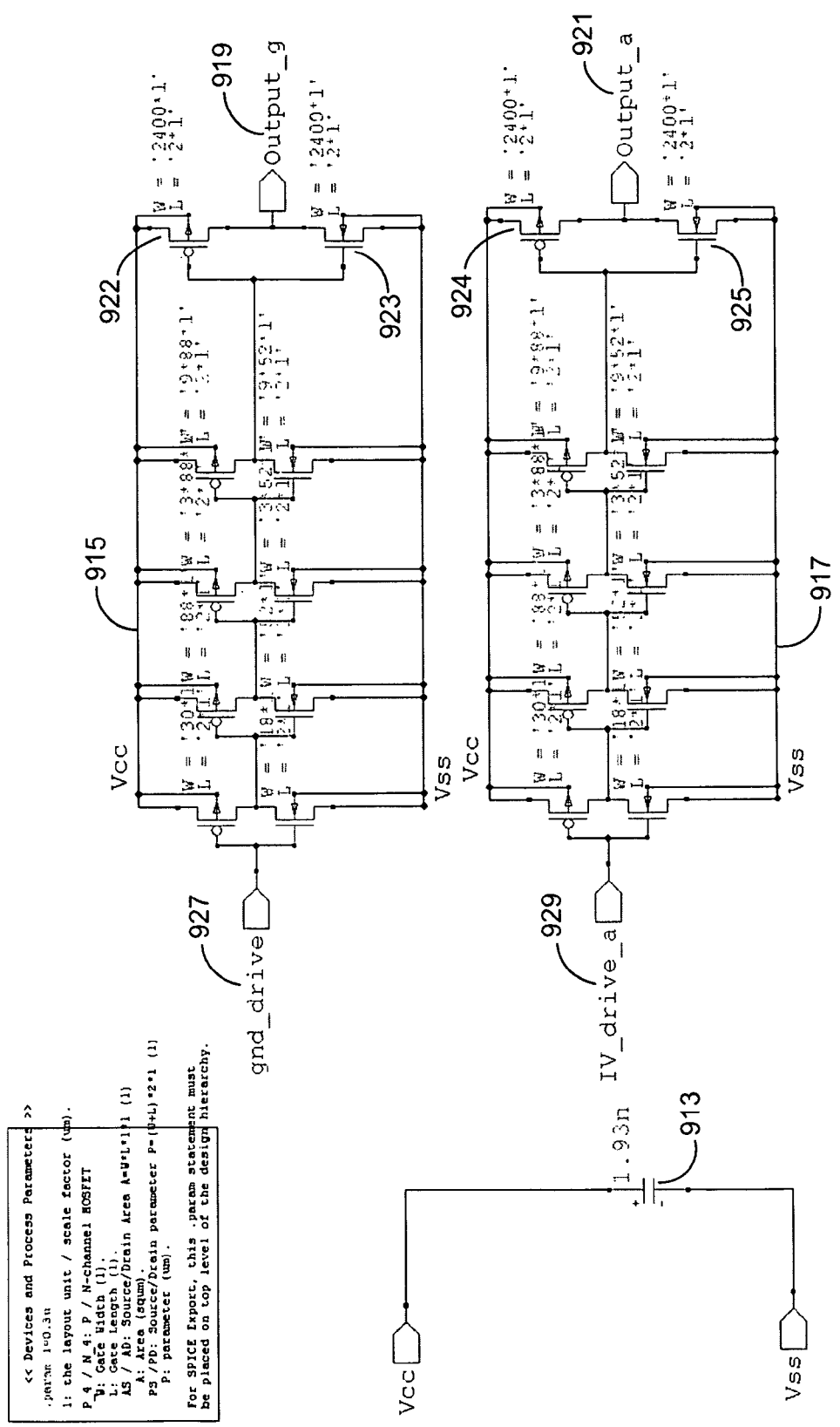

FIG. 9B is a more detailed view of chip 901 from FIG. 9A. There are two branches of the circuit. Core 909 contains the logic, while pads 911 drive the two capacitor plates. Pads 911 are shown in more detail in FIG. 9C. Capacitor 913 provides a quiet power supply. There are fan-outs 915 and 917 to drive the capacitor plates at outputs 919 and 921, going through some large transistors 922-925. Ground output 919 and IV output 921 are controlled by ground drive input 927 and 929, respectively.

Figure 9D:
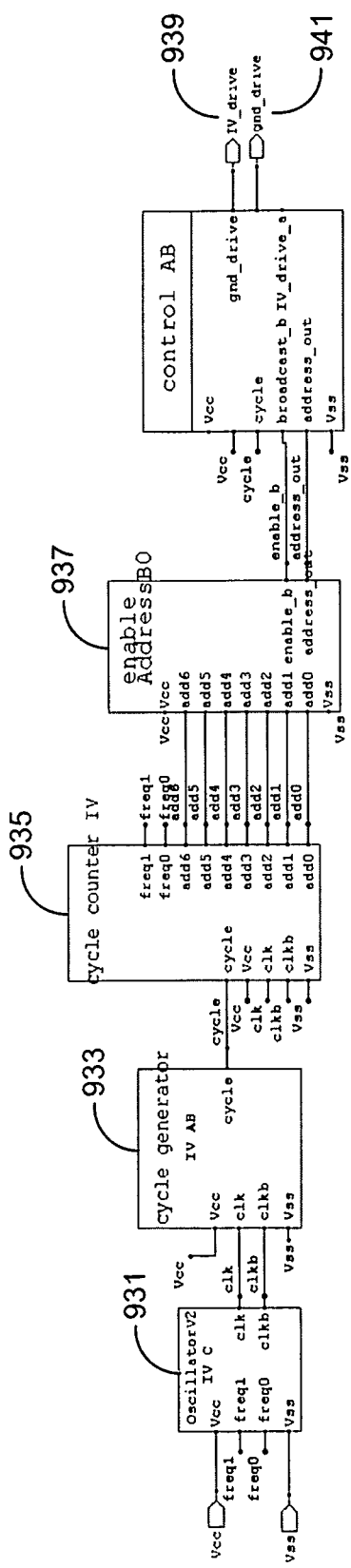

Core 909 from FIG. 9B is shown in more detail in FIG. 9D. Oscillator 931 takes the DC voltage from the battery and generates a clock. Block 933 generates a cycle from the clock. Block 935 counts the cycles, and then based on which cycle it is, generates an address which is descriptive of this particular broadcaster, and associated with a particular IV bag and its contents. Block 937 either enables broadcasting, and attaches a duty cycle, or disables broadcasting. When broadcasting is enabled, the address is broadcast through capacitive plates attached to outputs 939 and 941. Broadcasting is carried out by creating a high frequency signal between the ground plate at output 941 and the IV bag plate at output 939. The receiver used to pick up the signal has a plate which is attached to the body of the patient, and a plate which is referencing earth ground.

Since both the transmitter and receiver reference earth ground, there is a signal transmission loop present when the IV is attached to the patient and IV fluid is flowing. When the IV tube is attached to the patient, the signal is transmitted from the IV bag, down the tube, and picked up by the receiver located in or attached to the surface of the patient.

Figure 9E:
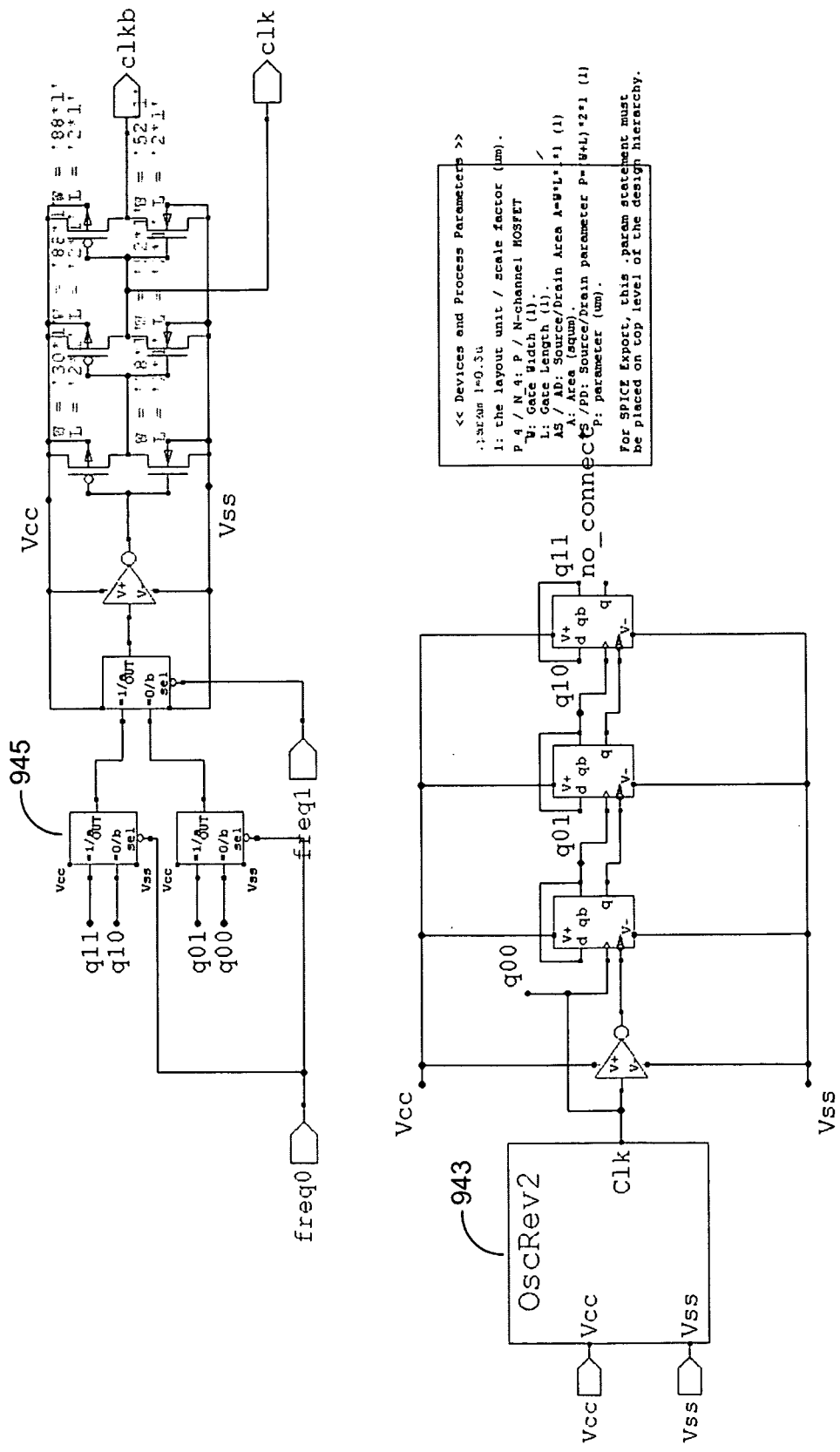

Oscillator 931 is shown in more detail in FIG. 9E. Oscillator 943 is followed by frequency divides to divide down the frequency. In this particular embodiment, there are four frequencies produced, allowing the transmitter to broadcast at any or all of them. Circuit 945 cycles through the four frequencies sequentially in order to find the one that works best. Also, if multiple IV bags or other systems are connected and broadcasting at the same time, they can be set to broadcast on different frequencies. In other embodiments, only one frequency is used. In yet other embodiments, a different number of frequencies can be used.

There are many other techniques, which would be obvious to one skilled in the art, that can be used to handle multiple transmitters broadcasting simultaneously, as well as to clean up the signal and improve signal integrity. For example, a spread spectrum design can be used which utilizes many frequencies and adds some noise cancellation.

Figure 9F:
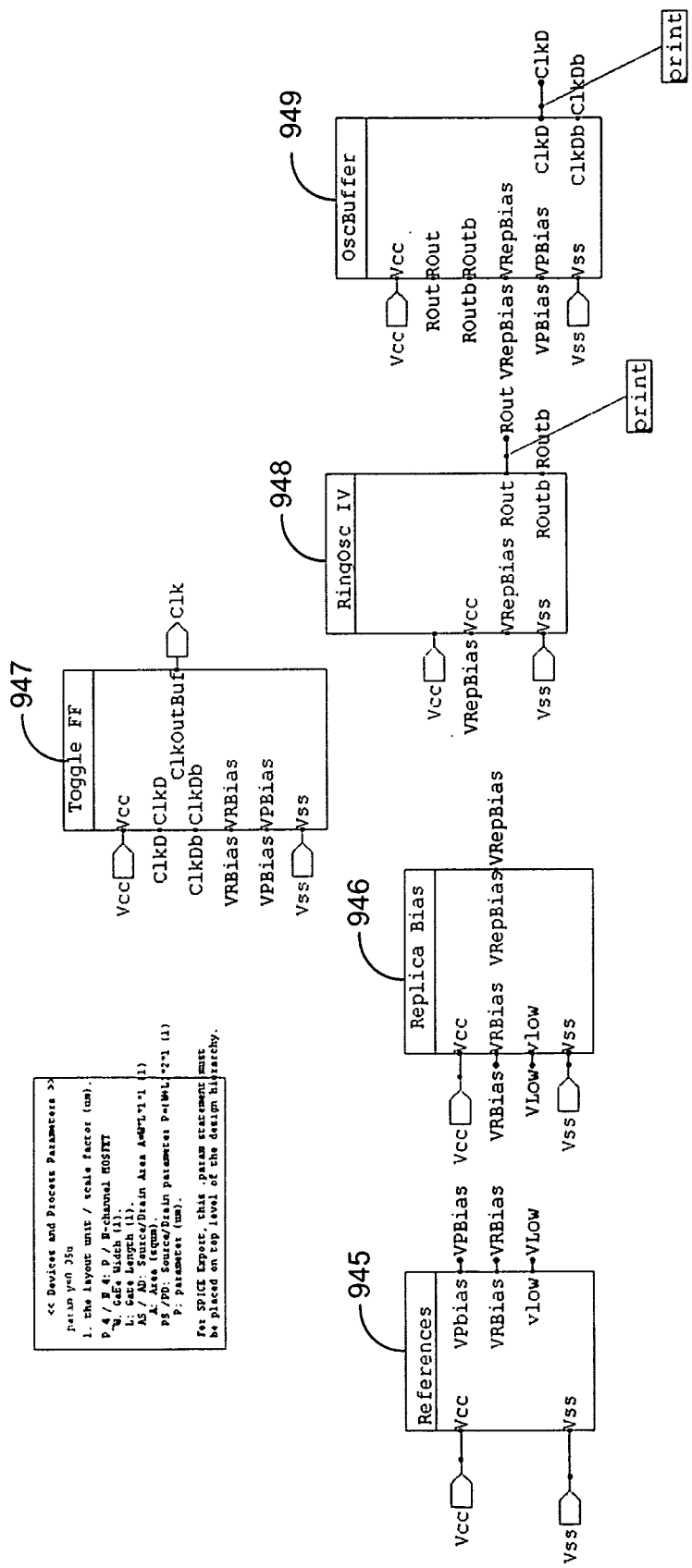
Figure 9G:
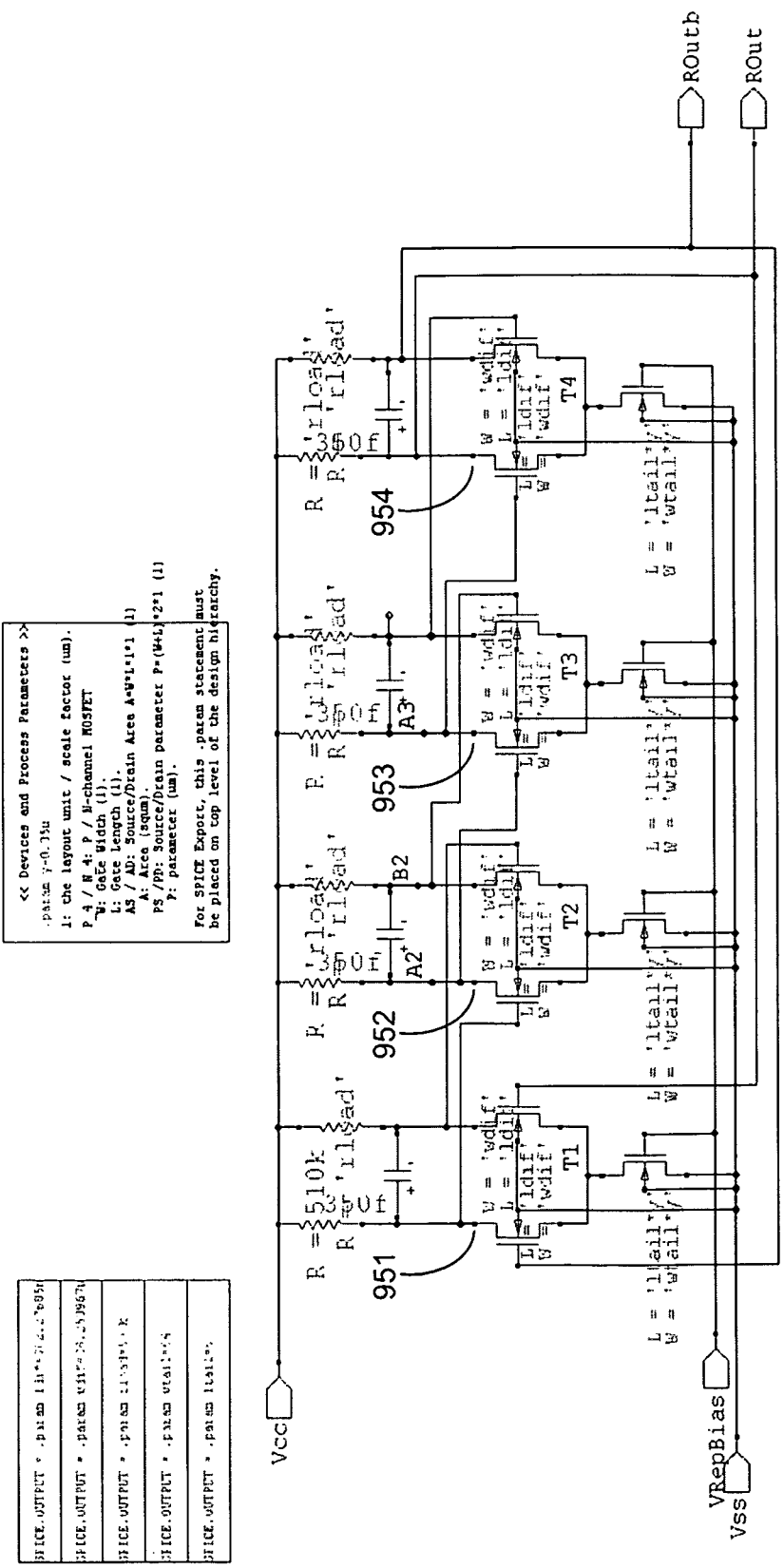

Oscillator 943 can be the same oscillator as discussed in U.S. Provisional Patent Application 60/829,832, entitled "In-Vivo Low Voltage Oscillator," hereby incorporated by reference in its entirety. The basic functional blocks of the oscillator are shown in FIG. 9F. There are five sub blocks 945-949. Ring oscillator block 948 is shown in FIG. 9G. It is a ring oscillator with differential pairs 951-954, which set up an oscillation. This oscillator has a stable output frequency regardless of the input voltage. It is a stable oscillator even at low voltages, such as about 1V to about 2V. This is important, so that even when the battery declines in power, the frequency will not shift too much.

Figure 9H:
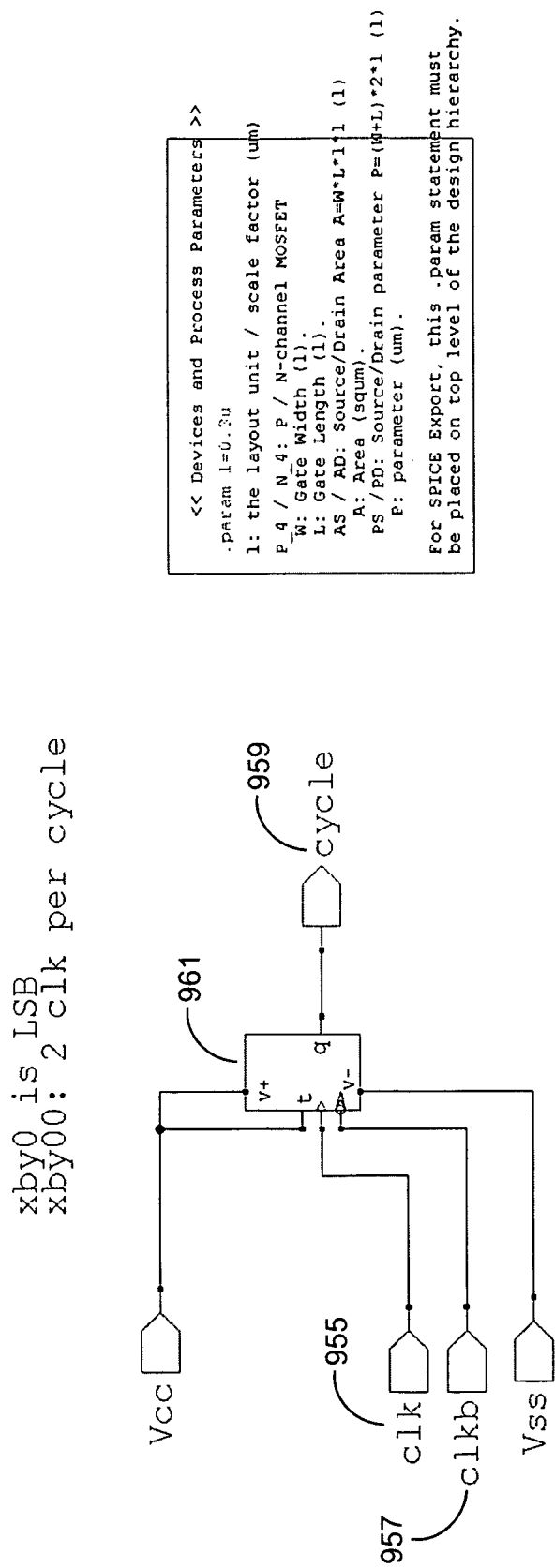

FIG. 9H shows cycle generator block 933 from FIG. 9D in more detail. The oscillator produces the input clock 955 and clock bar 957. The cycle generator then generates a cycle 959 by using a divide by two flip flop 961.

Figure 9I:
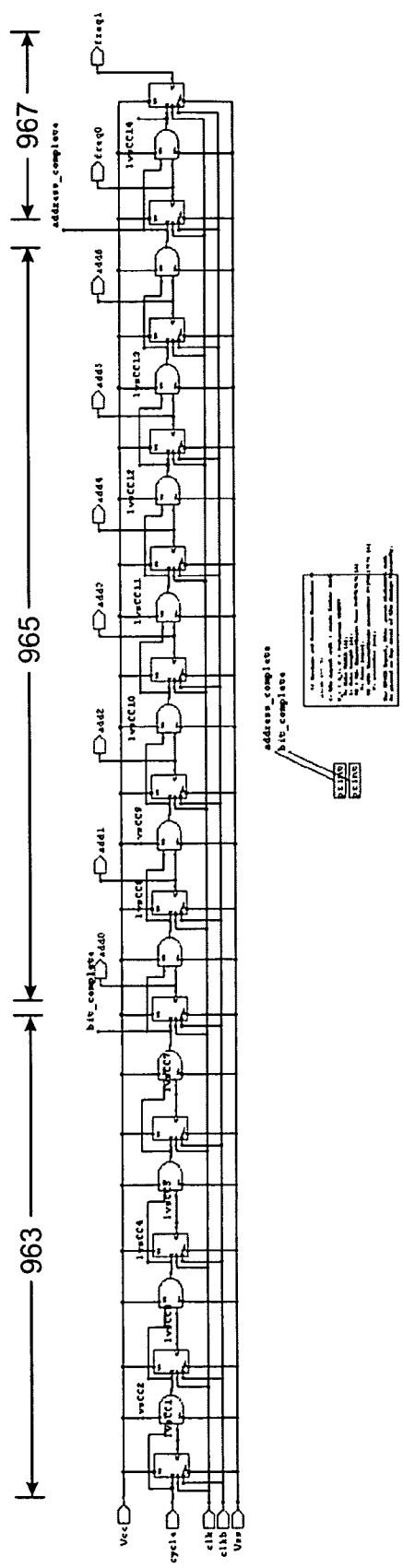

Cycle counter block 935 from FIG. 9D is shown in more detail in FIG. 9I. This block counts the cycles. There are five phases 963 per bit, so each bit will represent five bits worth of cycles. The address is contained in bits 965, and the frequency used contained in bits 967. In other embodiments, greater or fewer bits can be used in any portion of this circuit. For example, more bits can be added to the phase portion to get more bits of cycles. In some embodiments, where the frequency does not need to be changed, the frequency bits can be omitted.

Figure 9J:
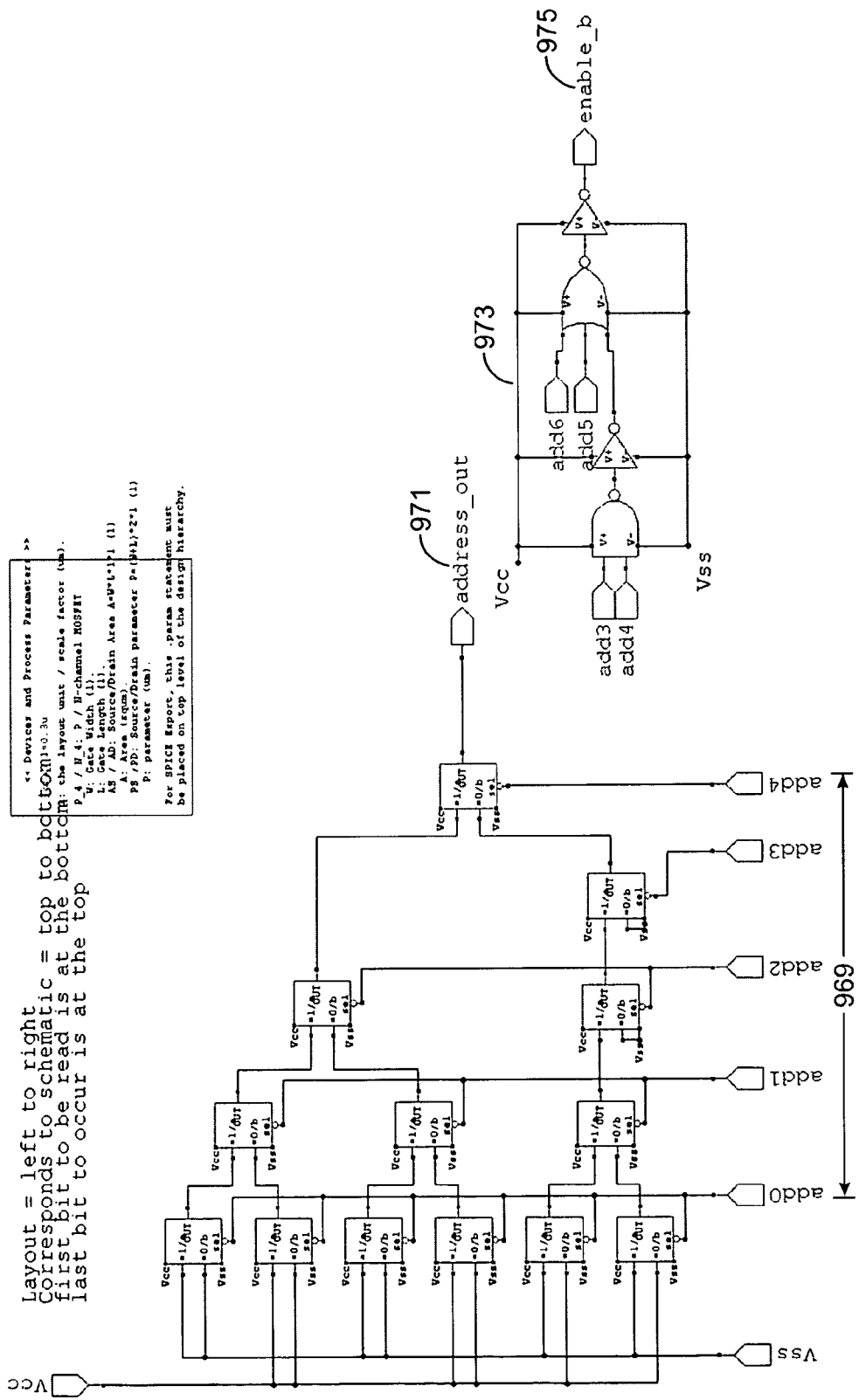

FIG. 9J shows a multiplex circuit which takes the address in 969 and produces the address out 971. Block 973 determines when the circuit will broadcast and when it will not, using enable output 975.

Figure 9K:
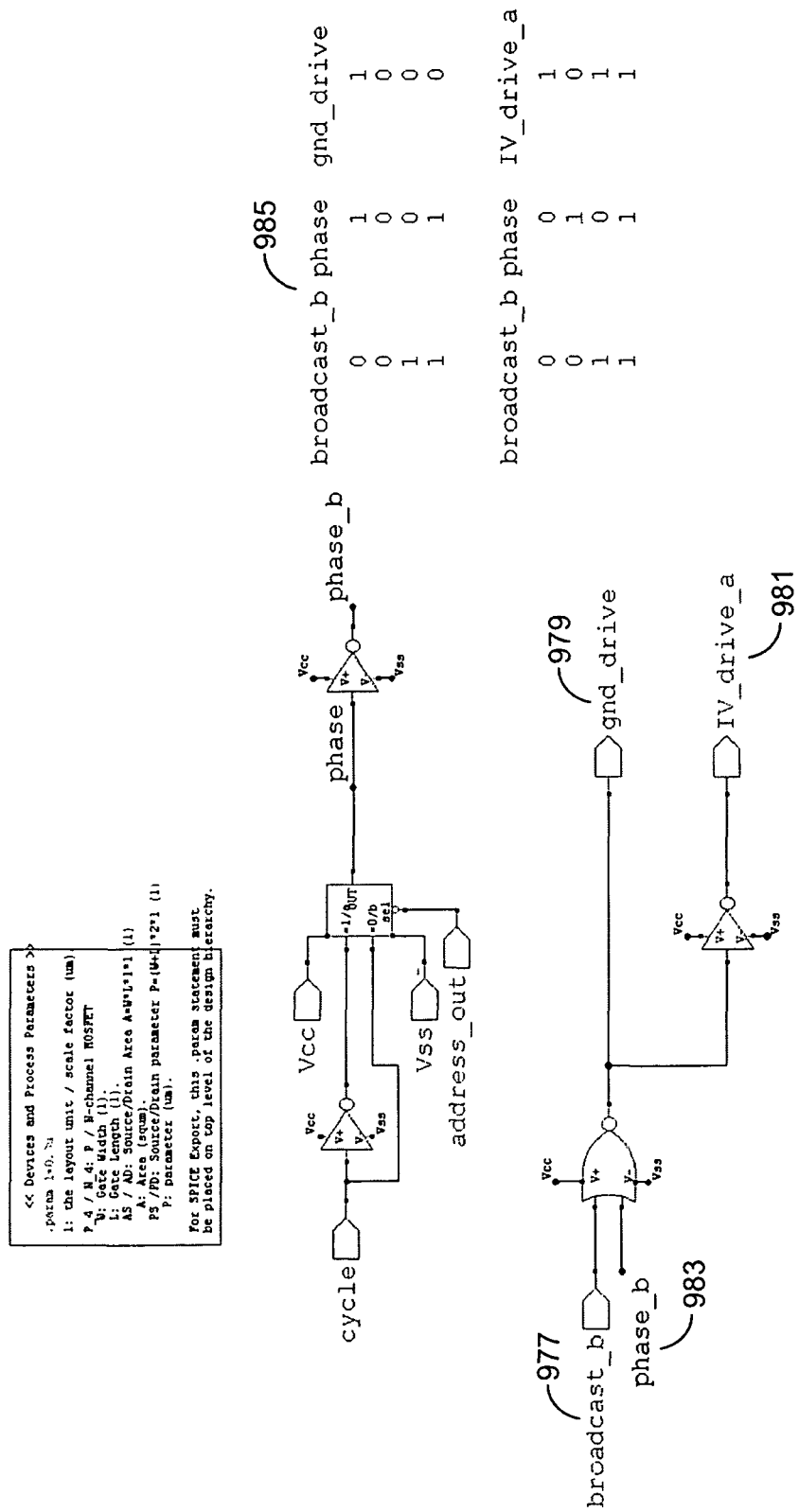

The control circuit which controls the broadcast signal at the capacitors is shown in FIG. 9K. The scheme used here is H-drive, so either the IV bag capacitor will be high and the ground capacitor low, or the ground capacitor will be high and the IV bag capacitor will be low. This circuit switches back and forth to give maximum output. Broadcast input 977 is the same as the enable output 975 from FIG. 9J. Broadcast input 977 determines whether or not broadcasting should be performed. When broadcasting is turned off, output drives 979 and 981 are frozen in a static state. It is capacitive drive, so they should not be stuck in a static state and leaking current.

When broadcasting is enabled, at every clock or every cycle the drives 979 and 981 are switching polarity and broadcasting the signal. This embodiment uses phase shift keying, so the polarity is switched using phase input 983 to encode different bits in the signal. Logic diagram 985 shows how the circuit operates for each broadcast input 977 and phase input 983. Other communication techniques, such as frequency shift keying, can be used in other embodiments.

This circuit can operate at about 20 kHz to about 1 GHz, such as about 100 kHz to about 20 MHz, and including about 200 kHz to about 1 MHz. The system can utilize multiple frequencies, a spread spectrum design, or a myriad of other techniques which are well known in the art in order to successfully transmit and receive the signal in a noisy environment. The circuit shown here is merely a simple example, and other layers of complexity to make the system more robust can be added.

Figure 10A:
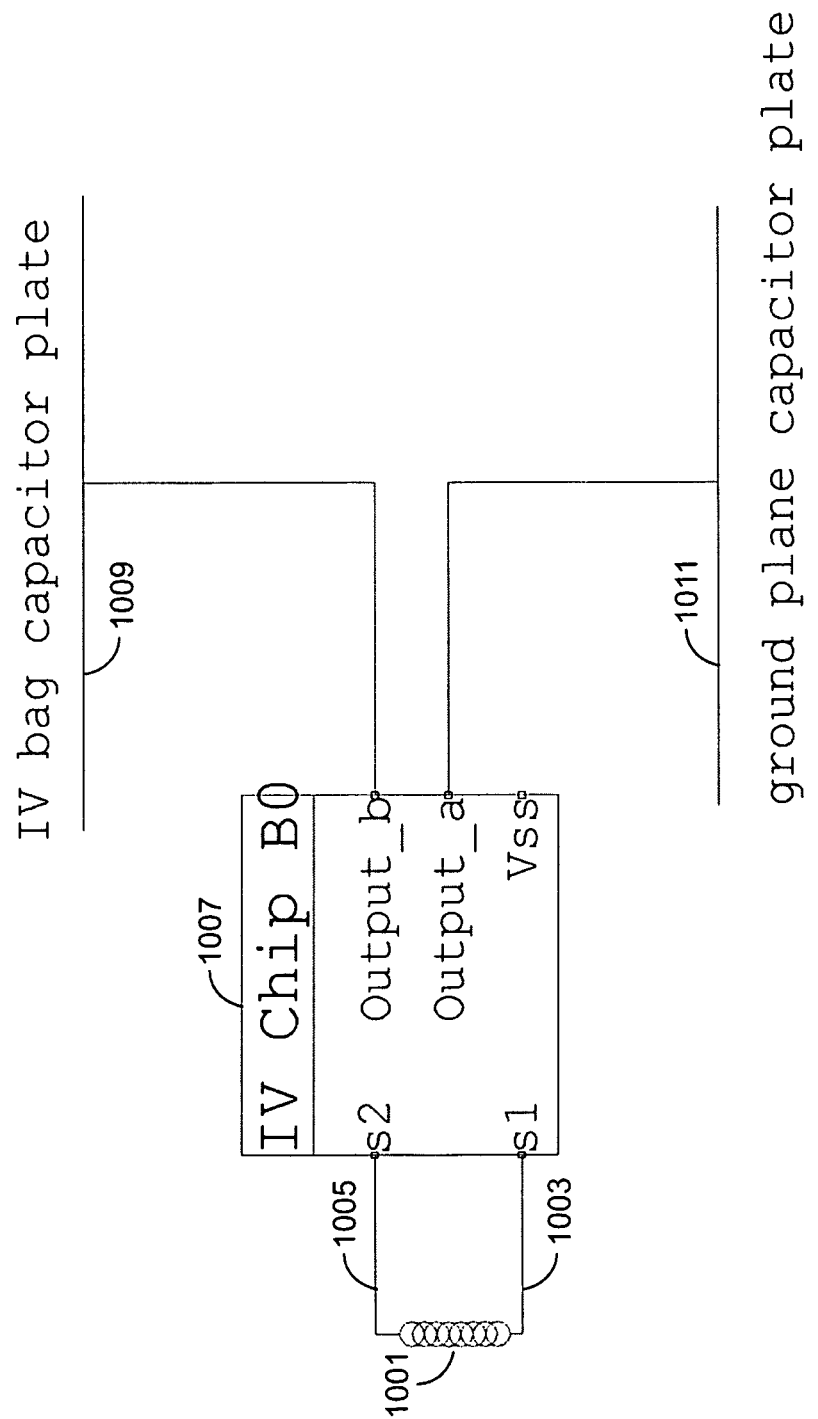
FIGS. 10A-10I depict an IV bag broadcast circuit in accordance with another embodiment of the invention.

FIG. 10A shows a top level view of another embodiment of the broadcast circuitry. This embodiment is similar to the embodiment of FIGS. 9A-K, except that there is no battery. Instead there is a coil 1001 or an antenna which will receive an AC field across inputs S1 1003 and S2 1005. Chip 1007 then takes the AC voltage and converts it to a DC voltage to power the rest of the circuitry. The chip controls the output at IV bag capacitor plate 1009 and ground plane capacitor plate 1011. The AC field can be generated from a coil located elsewhere in the proximity of the IV bag chip. For example, it can be integrated into the IV pump system, and draw power from the wall plug.

Figure 10B:
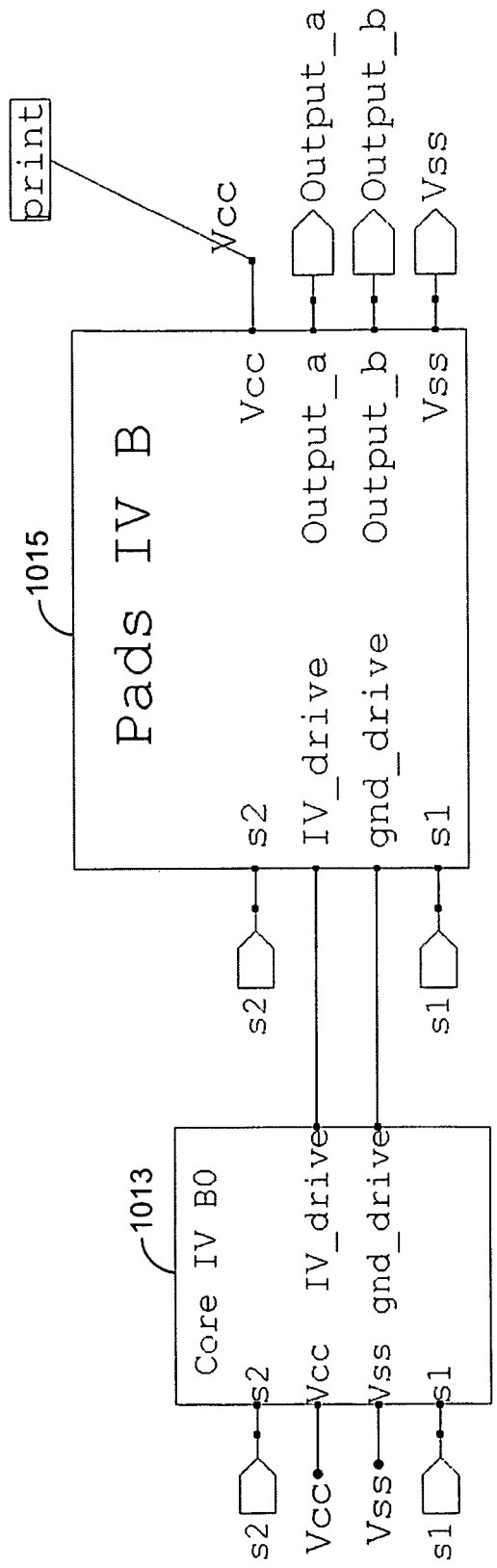

FIG. 10B shows a more detailed view of chip 1007 from FIG. 10A. Core 1013 contains the logic, while pads circuit 1015 controls the output at the capacitor plates.

Figure 10C:
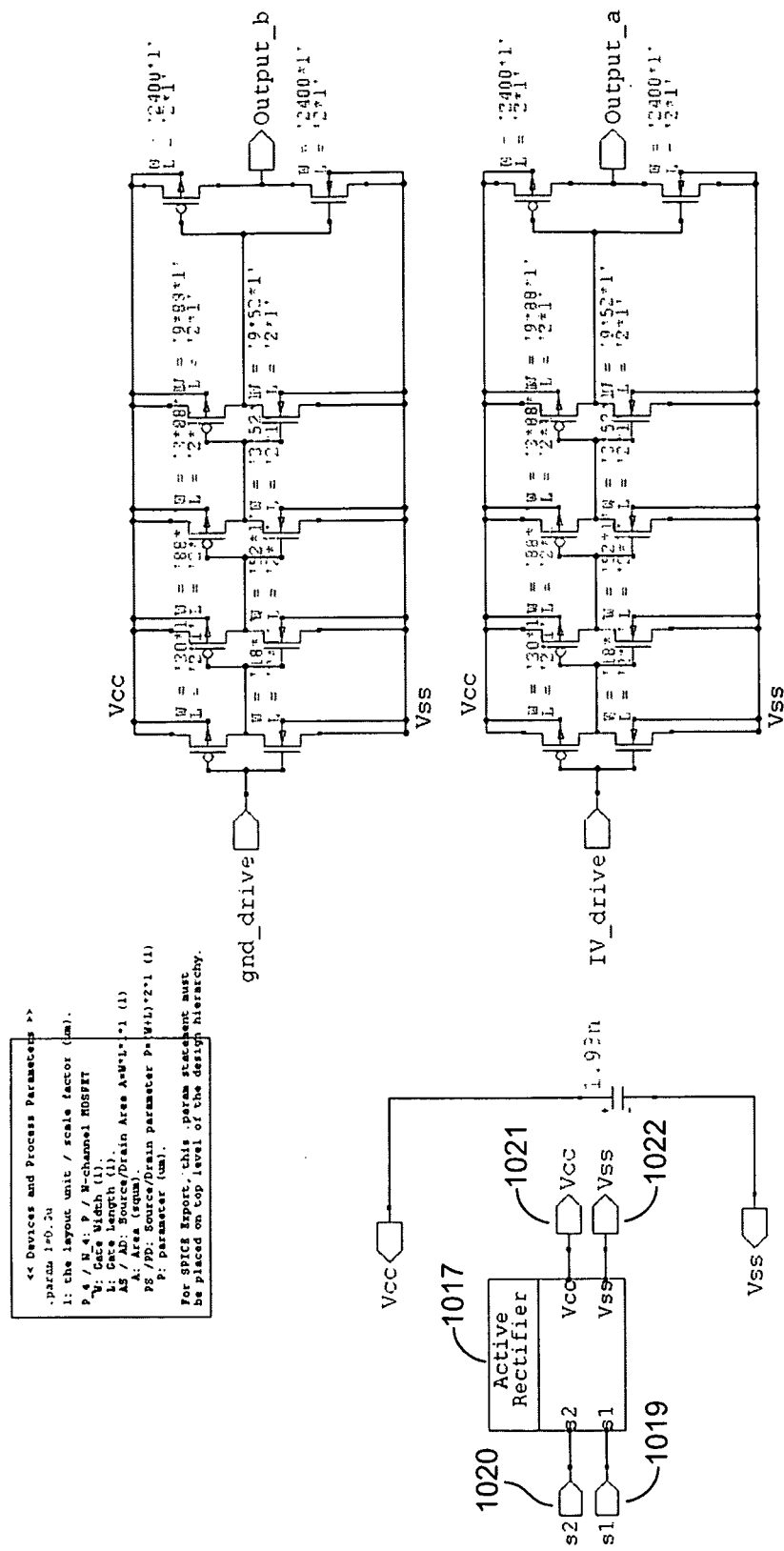

A more detailed view of pads circuit 1015 is shown in FIG. 10C. The drive portion of the pads circuit is similar to that shown in FIG. 9C. The difference is that circuit block 1017 converts the AC signal at S1 1019 and S2 1020 and converts it into a DC signal at Vcc 1021 and Vss 1022 through an active rectifier.

Figure 10D:
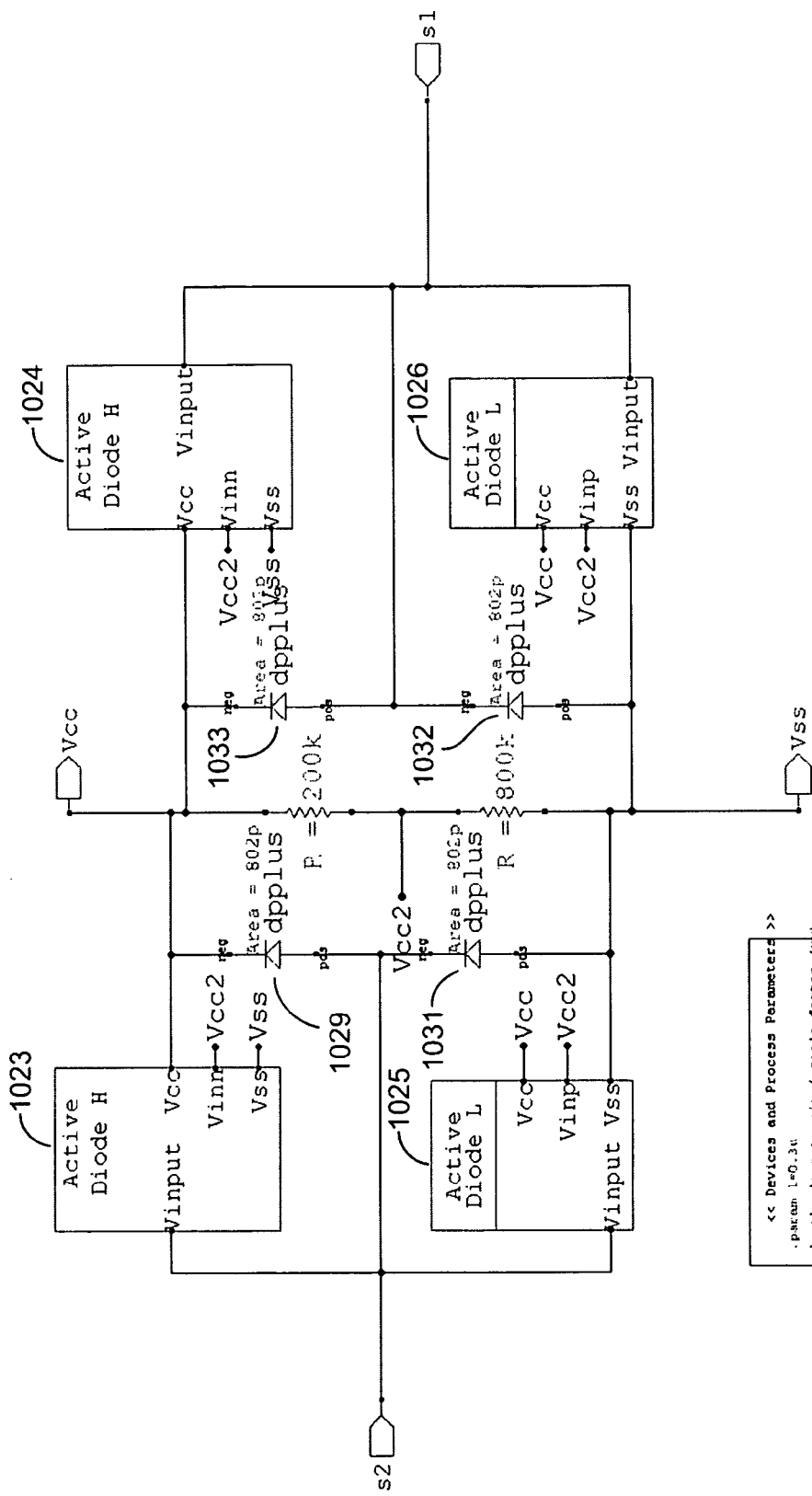

The active rectifier is shown in FIG. 10D. Active diodes 1023-1026 form a diode bridge. Diodes 1029-1033 are primarily for electrostatic discharge protection, but could function as diodes in other embodiments. Diodes 1023-1026 are customized active diodes. When the voltage drop across the active diode gets to be greater than the threshold, a switch is flipped to short the input to the output. This allows the active diode to act as a diode, but without the voltage drop, allowing the circuit to operate at a lower voltage. There is a minimal voltage drop, but much less than with a passive diode. When the voltage goes back below the threshold, the active diode senses this and quickly opens the switch. The circuit can operate at voltages as low as about 0.8V, such as about 0.9V. Other embodiments can use passive diodes, such as Schottky diodes instead of active diodes.

Figure 10E:
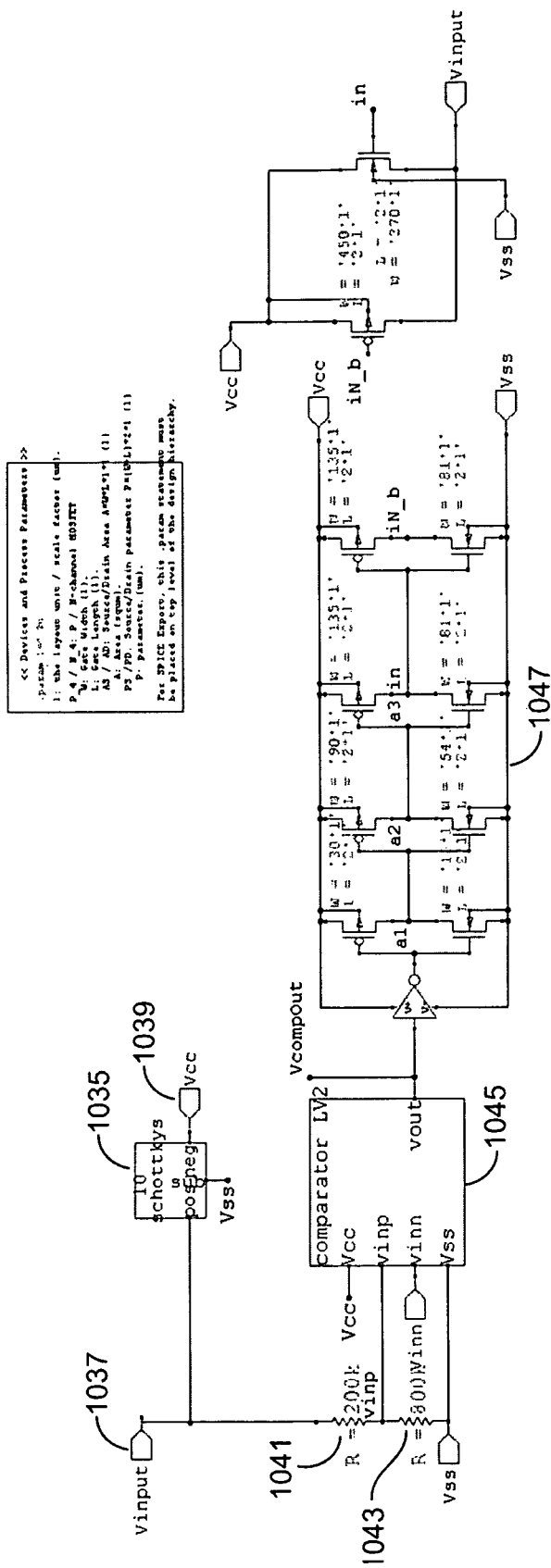

A more detailed view of active diode highs 1023 and 1024 is shown in FIG. 10E. There are ten Schottky diodes 1035 in parallel between input 1037 and Vcc 1039. The input 1037 in this case can be either S1 or S2, since they are parallel structures. Resistors 1041 and 1043 form a voltage divider to get the signal within a relatively easy operating range for the comparator 1045. The signal is fanned out in circuit block 1047.

Figure 10F:
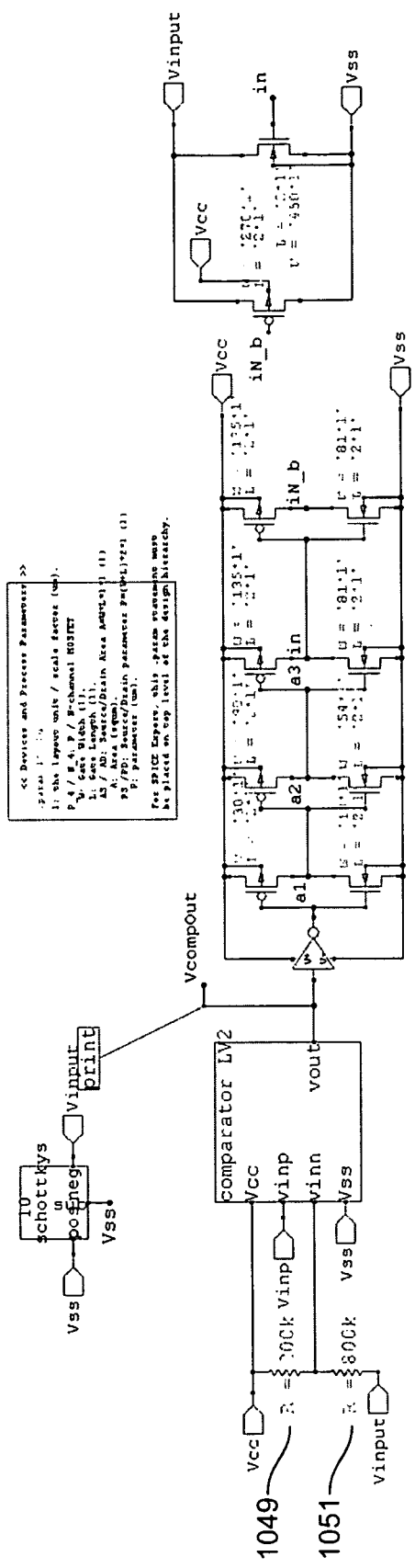

FIG. 10F shows the active diode lows 1025 and 1026 from FIG. 10D. They are essentially the same as the active diode highs shown in FIG. 10E, except that the resistors 1049 and 1051 that form the voltage divider are flipped around.

Figure 10G:
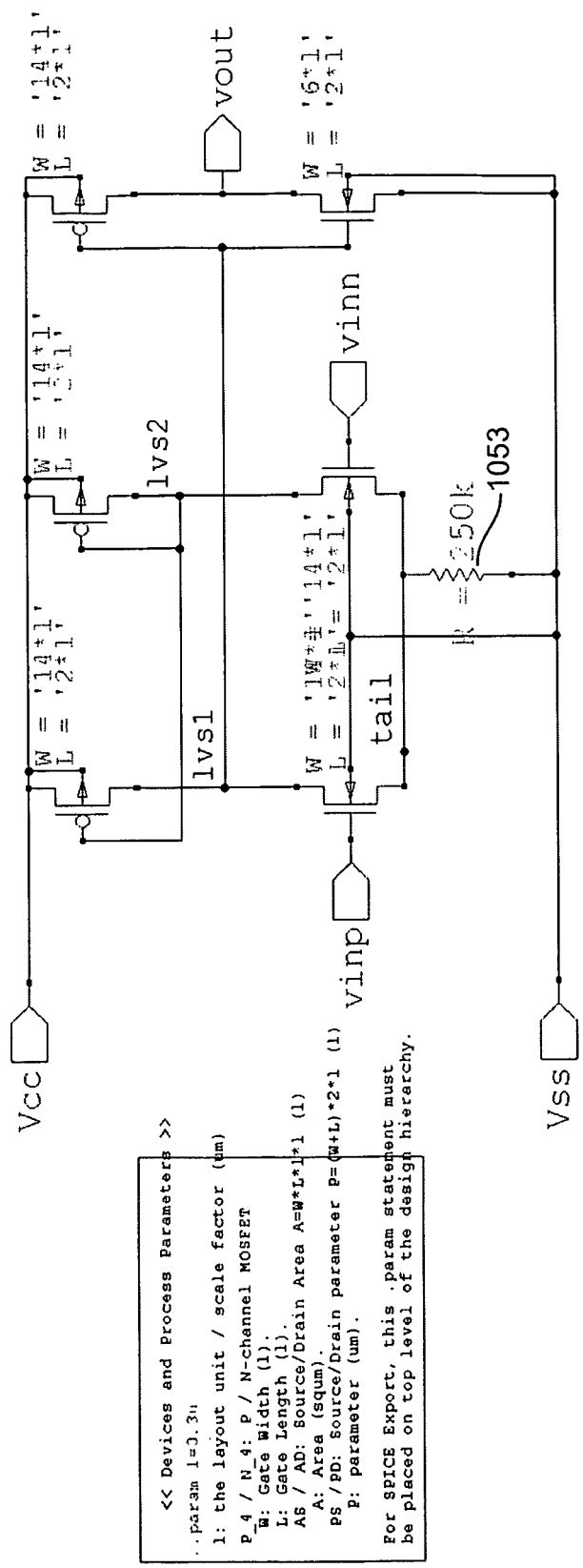

The comparator 1045 from FIG. 10E is shown in more detail in FIG. 10G. A passive tail resistor 1053 is used instead of an active component with bias current. This is done to reduce the number of transistors used in order for the circuit to work at lower voltages.

Figure 10H:
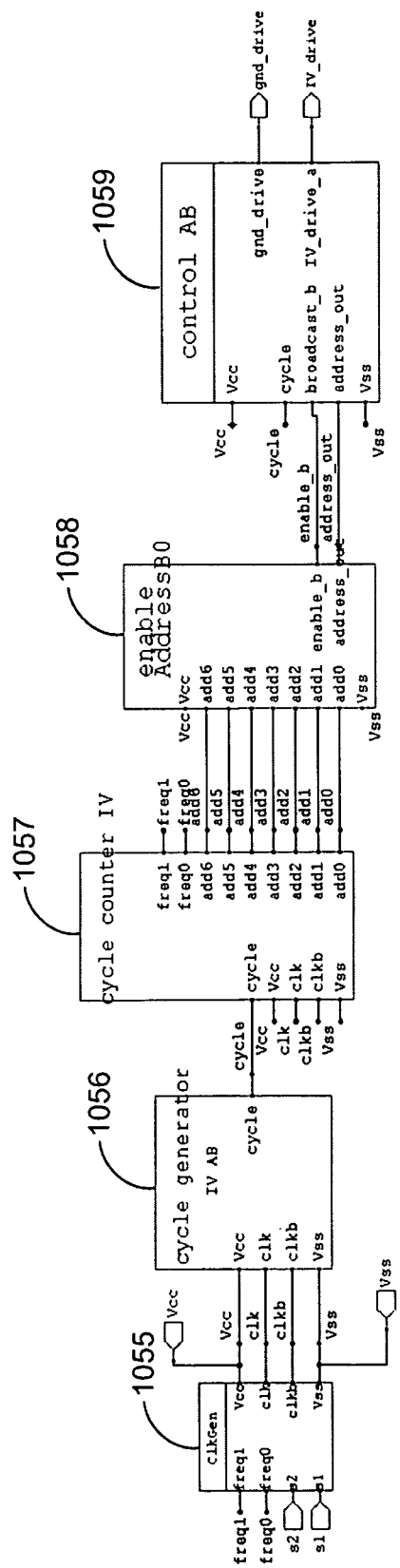

FIG. 10H depicts the core circuitry 1013 from FIG. 10B. The core circuitry includes clock generator block 1055, cycle generator 1056, cycle counter 1057, broadcast enable block 1058, and control block 1059. Blocks 1056-1059 are essentially the same as in the embodiment of FIG. 9D. Clock generator block 1055 is used in this embodiment instead of the oscillator.

Figure 10I:
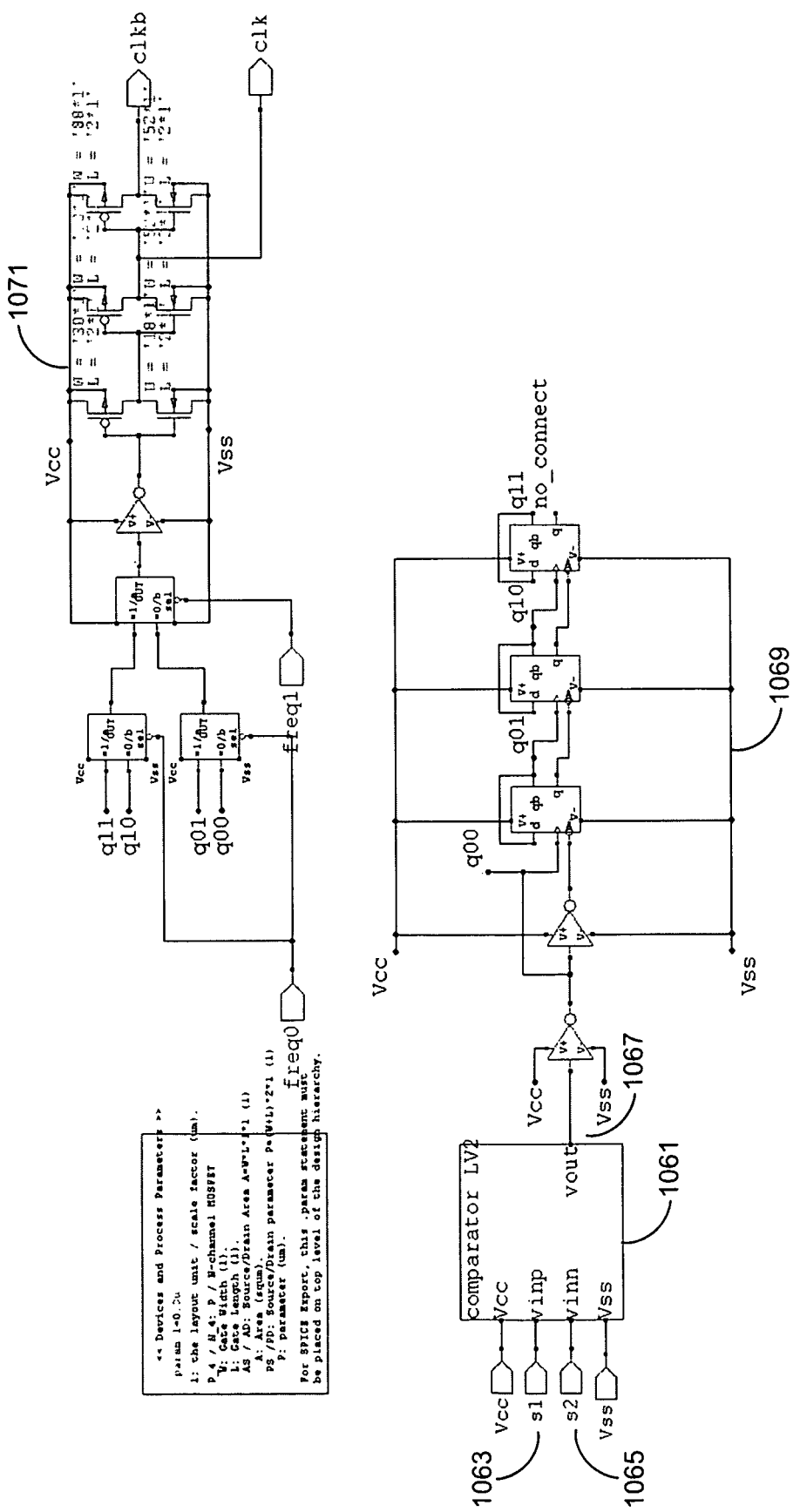

Clock generator block 1055 is shown in more detail in FIG. 10I. Comparator 1061 is the same as the comparator shown in FIG. 10E. It compares the inputs S1 1063 and S2 1065, which are the AC input signal, and uses the zero crossings to generate a clock signal 1067. The clock signal is divided by either 2, 4, 8, or 16 in block 1069, and then fed to block 1071 where it is fanned out to drive the rest of the circuitry.

In other embodiments, the IV circuitry can be configured to measure and transmit the volume of fluid in the IV bag, which can give an indication of flow rate when multiple data points are gathered over a given time. In this embodiment, two capacitor plates are stuck or otherwise attached to the IV bag, with a third ground plate electrically attached to earth ground. The two capacitor plates attached to the IV bag do not need to be parallel and can be in a variety of shapes and orientations. The capacitance measured between the two plates attached to the IV bag will vary depending on the amount of fluid in the bag. When there is a lot of fluid in the IV bag between the two capacitor plates, the capacitance will be higher than when the fluid drains out of the IV bag, and there is more air between the plates. By looking at the change in capacitance over time, one can get an indication of the flow rate of medication from the IV bag.

With flexible IV bags, the capacitance measured may not vary linearly with the amount of fluid in the IV bag. For some applications, it may not be important to have a high level of accuracy, so this is acceptable. In other embodiments, the signal can be post linearized with look-up tables. If the typical capacitance versus fluid volume curve for a particular IV bag is known, this information can be used to make the calculated flow rates more accurate. In some embodiments, a certain number of points from the capacitance versus fluid volume curve that is characteristic of the type of bag being used can be transmitted along with the address. In other embodiments, modifications can be made to the IV bag or the shape of the capacitor plates in order to make the capacitance versus fluid volume curve more linear. For example, if the walls of the IV bag are made more rigid such that it does not change shape while the IV fluid is flowing, that will make the curve more linear.

In some embodiments, the chip can be programmed to broadcast the identifier address through the capacitor plates which are attached to the IV bag. After broadcasting the address for some predetermined number of pulses, the broadcaster goes quiet. During this time, the voltage between the two IV bag capacitor plates is ramped up and then discharged when it reaches a threshold. The voltage is ramped up a predetermined number of times, and these cycles are counted.

After the voltage has been ramped up and discharged a certain number of times, another broadcast period follows. The time which passes between signal broadcasts will vary with capacitance. When the IV bag contains more fluid, the capacitance will be higher, and the time between signal broadcasts will be longer. As the IV bag drains, the capacitance will go down, and the time between signal broadcasts will get shorter. By counting the oscillator cycles during the ramp up period, the time between broadcasts can be measured, and the change can be monitored to give an indication of flow rate.

In other embodiments, other schemes to measure the change in capacitance can be used.

Figure 11A:
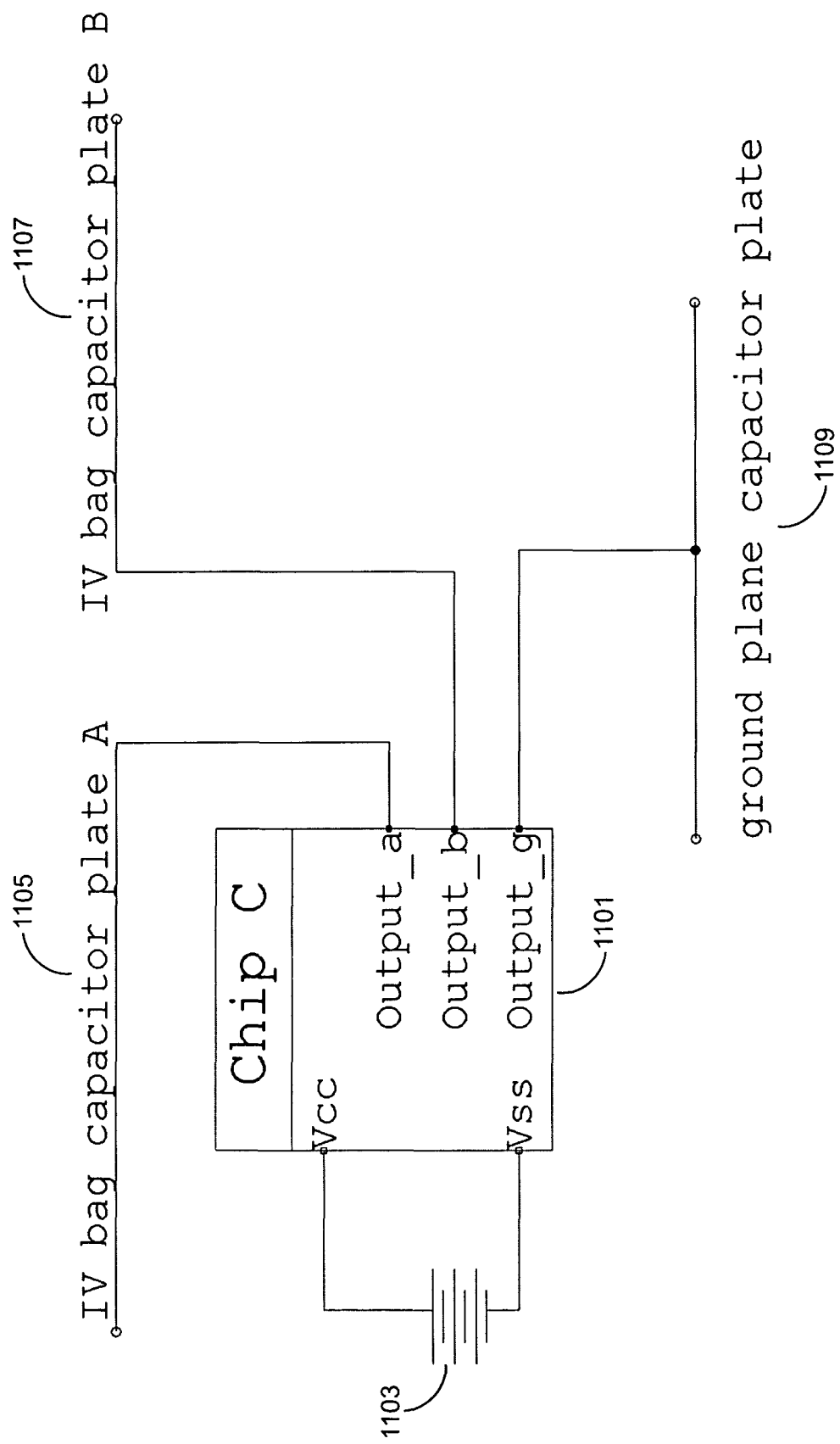
FIGS. 11A-11F depict an IV bag broadcast circuit in accordance with yet another embodiment of the invention.

FIG. 11A shows a top level view of a broadcaster circuit configured to measure capacitance between two plates attached to the IV bag, which can be used to determine fluid volume and flow rate information. Chip 1101 is powered by battery 1103, and controls the voltage at IV bag capacitor plates 1105 and 1107, as well as ground plane capacitor plate 1109. In other embodiments, a coil may be implemented to receive power.

Figure 11B:
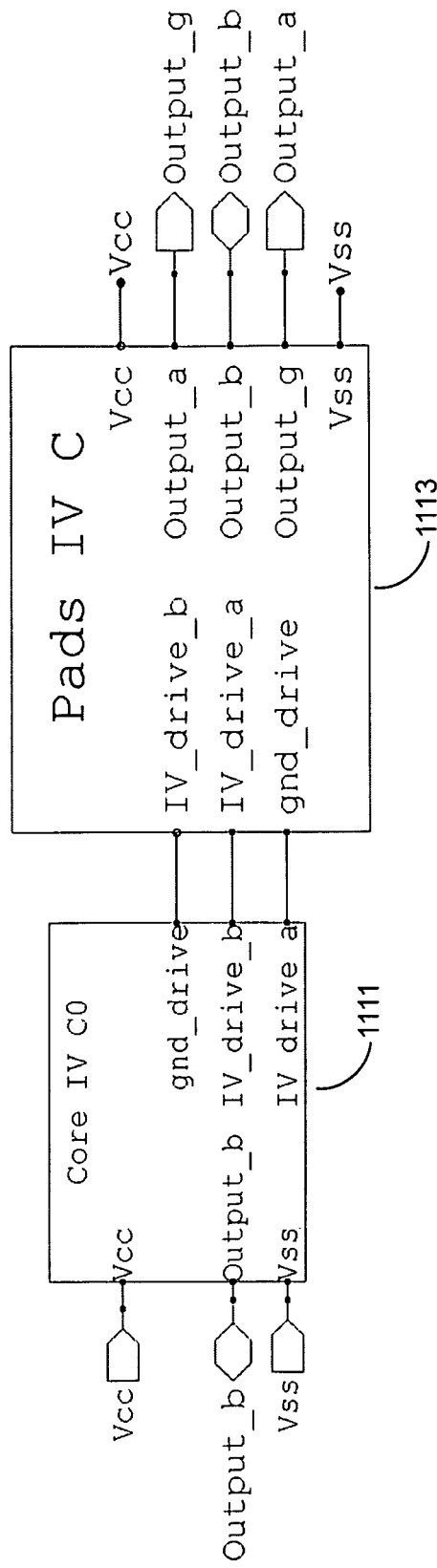

A more detailed view of chip 1101 is shown in FIG. 11B. The chip includes core 1111 and pads circuit 1113.

Figure 11C:
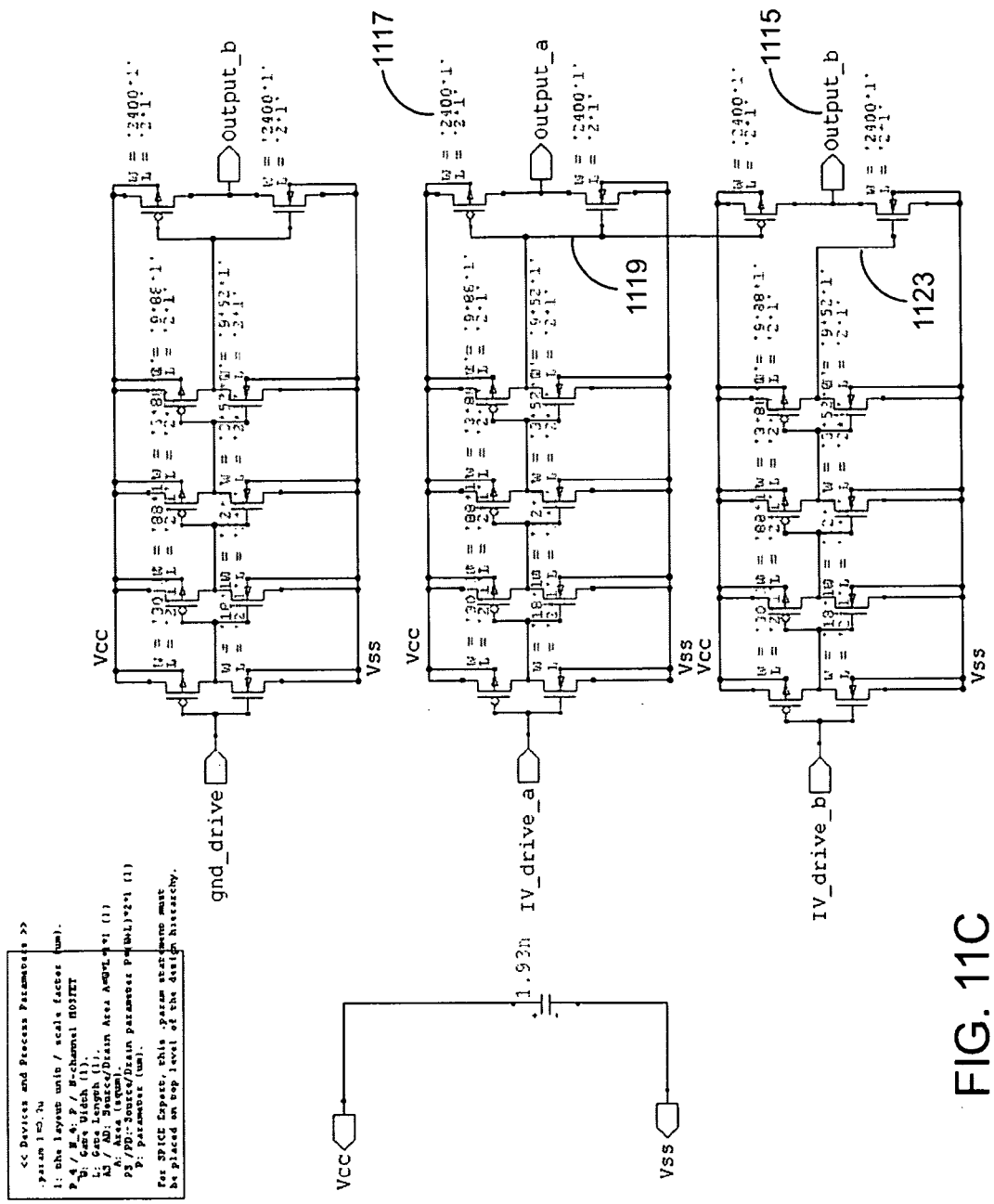

Pads circuit 1113 is shown in more detail in FIG. 11C. It is similar to the pads circuit previously discussed in FIG. 9C. There is another output B 1115 that corresponds to the second IV bag capacitor plate in addition to output A 1117. Also, drive gate 1119 is tied to the high voltage side of the output driver for output B 1115. During broadcasting, both output A 1117 and output B 1115 are broadcasting the same signal. During the ramp up period, output A 1117 is tied to ground, and output B 1115 is floating during ramp up, and then tied to ground to discharge the capacitor.

There is an independent drive 1123 to short output B 1115 to ground. The transistor is relatively large, which provides a quick discharge. There is a small delay once the voltage passes the threshold during ramp up before the capacitor is discharged. There is also a slight delay at the lower voltage before the next ramp up. This creates a discontinuity when calculating the change in capacitance over time, but can be compensated for in the calculation.

Figure 11D:
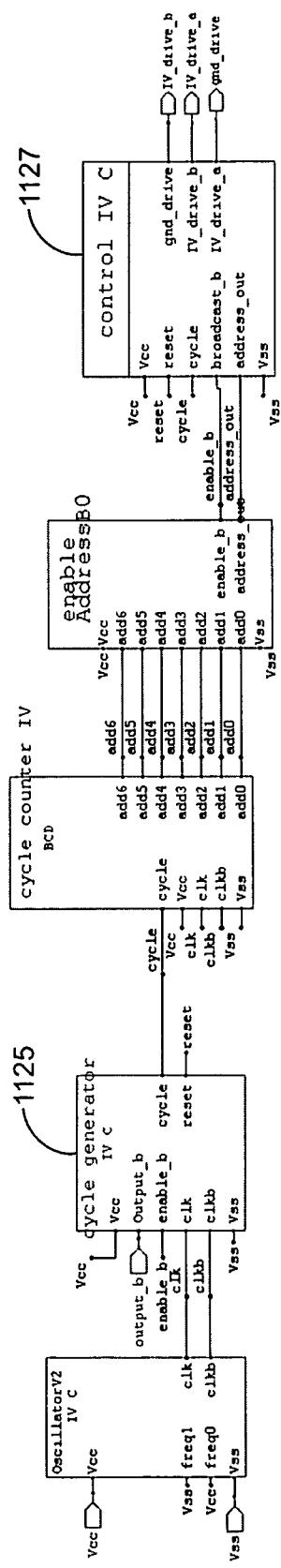

Core circuit 1111 from FIG. 11B is shown in more detail in FIG. 11D. It is similar to the core circuit discussed in FIG. 9D, except the cycle generator 1125 and the control block 1127 are different.

Figure 11E:
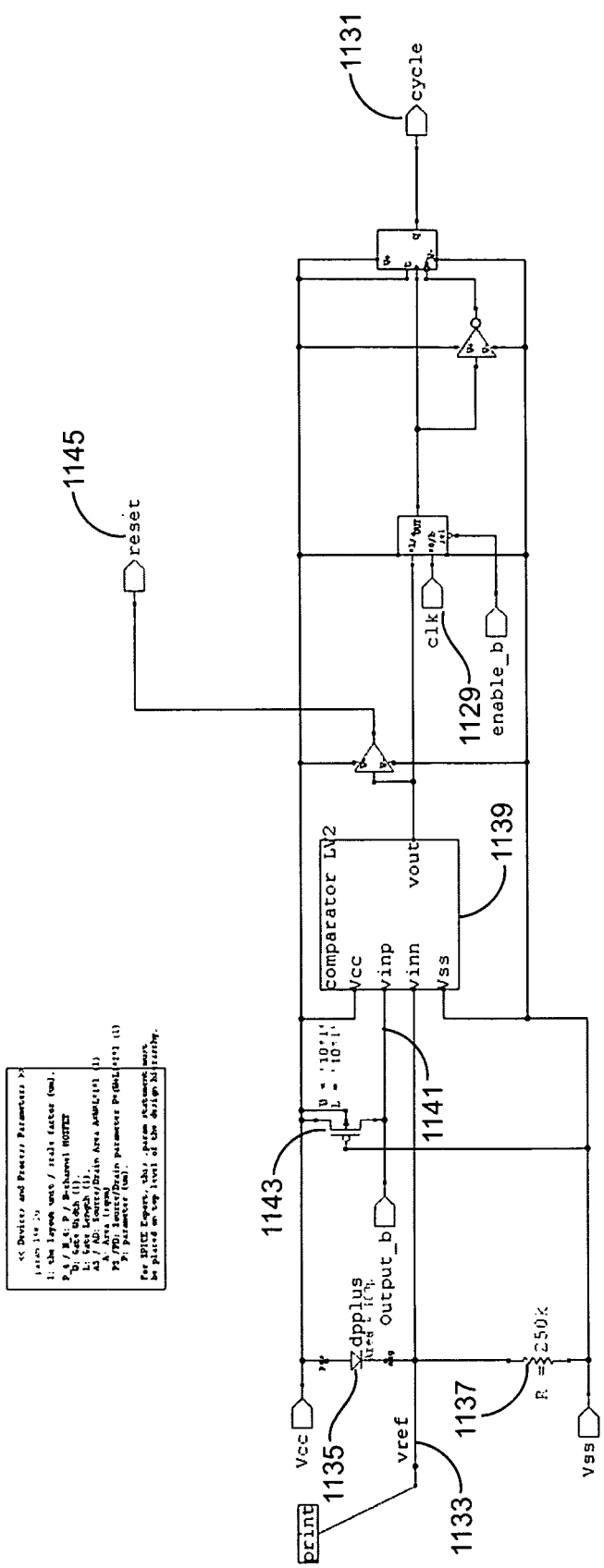

FIG. 11E shows the cycle generator 1125 from FIG. 11D. When broadcasting is enabled, clock 1129 is sent out as cycle 1131. In between broadcasts, the rest of the circuit acts as the ramp up system. There is a reference voltage 1133 made from diode 1135 and resistor 1137. Reference voltage 1133 is fed into comparator 1139, which compares reference voltage 1133 to the voltage on the capacitor 1141. Current source 1143 provides the ramp to drive up the capacitor voltage. When the voltage goes above the threshold, reset 1145 is triggered, which shorts the capacitor to ground. Once the comparator determines that the voltage is below the threshold, the voltage is ramped up again.

Figure 11F:
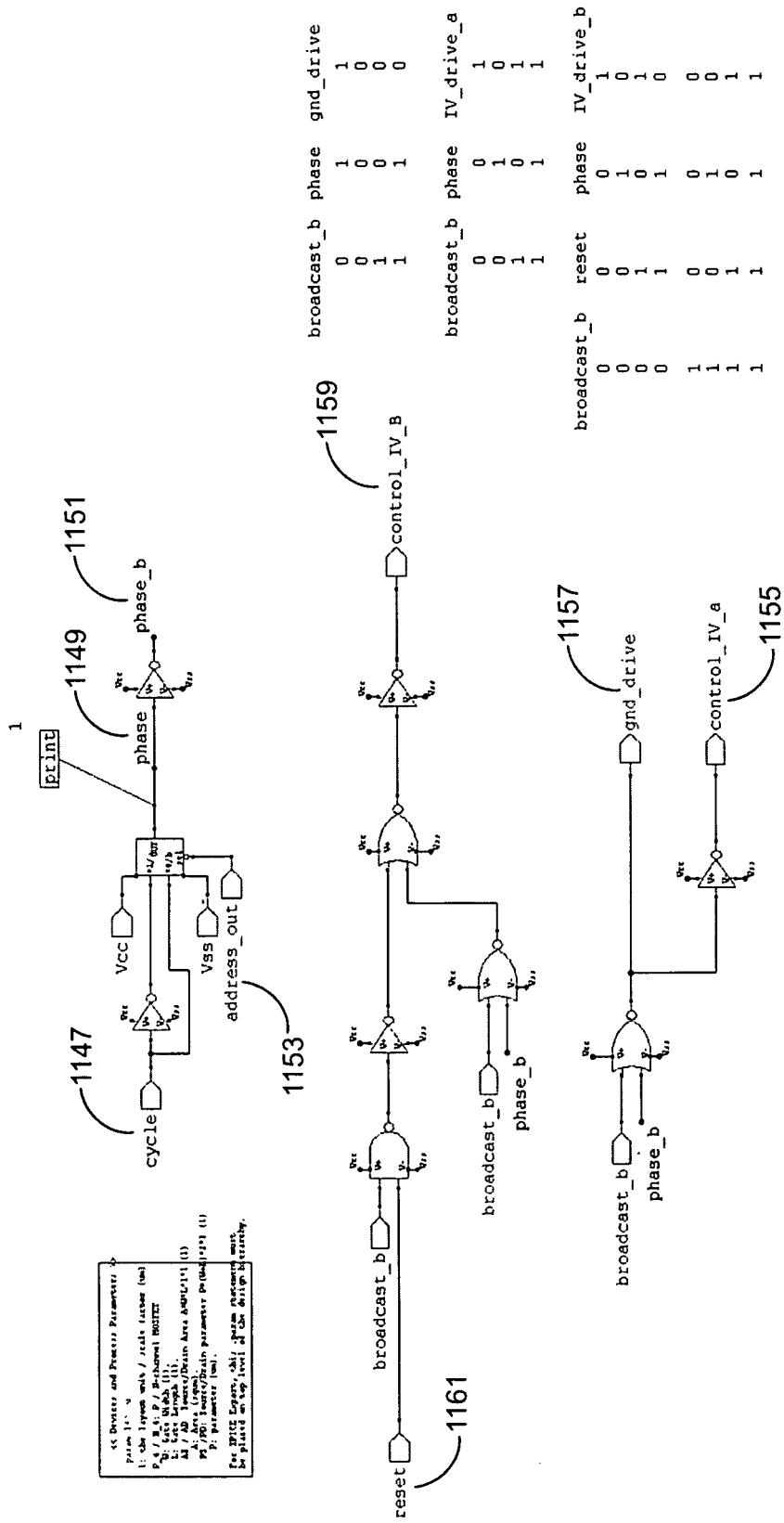

The control block is shown in more detail in FIG. 11F. Cycle 1147 is used to generate a phase 1149 and a phase bar 1151 based on the address 1153. The phase is used in conjunction with the broadcast enable bit to control outputs control A 1155, ground drive 1157, and control B 1159. When not broadcasting, control A 1155 is tied to ground while output B 1159 goes high unless reset 1161 is activated. When broadcasting, the reset does not matter, and the phase determines the signal at control A 1155 and control B 1159.

A simple implementation of a receiver which monitors multiple frequencies and picks up the signal sent by the IV bag broadcaster is depicted in FIGS. 12A-12F. This circuit was made for demonstration purposes only, and can contain much more complexity and more features in other embodiments.

Figure 12B:
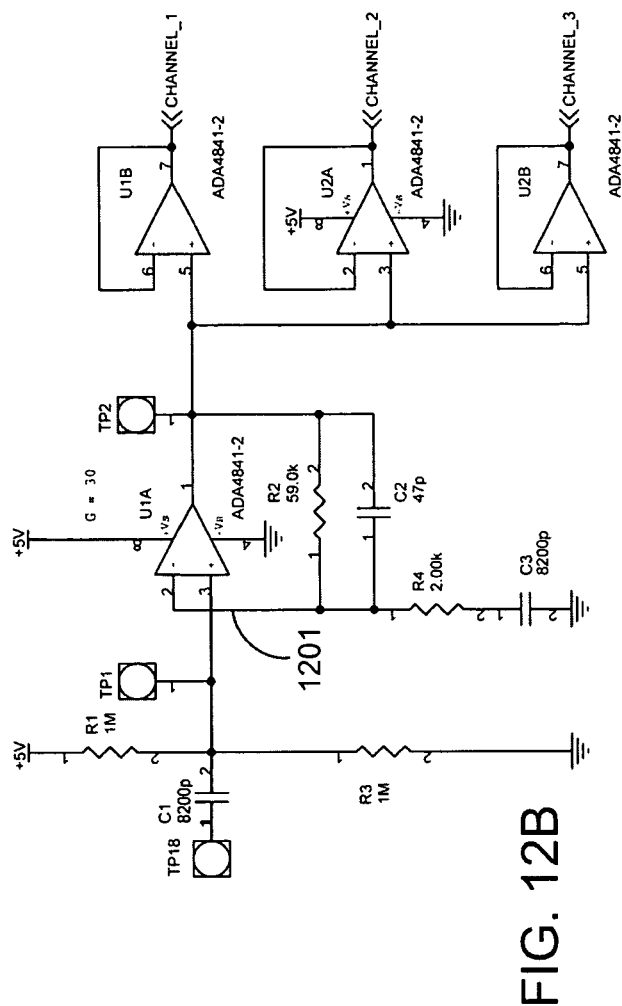
FIGS. 12A-12F depict a receiver circuit for the IV bag system.
Figure 12A:
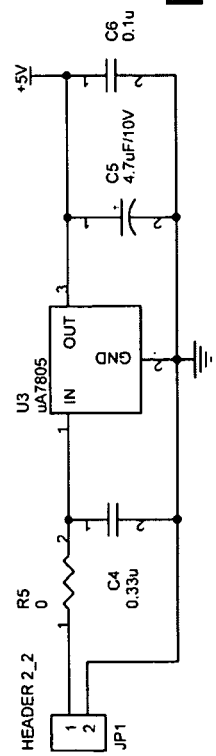

FIG. 12A shows a linear regulator. FIG. 12B is the first gain stage of the receive channel. There is a high pass filter 1201, and the signal is amplified, followed by some band limiting and buffers.

Figure 12C:
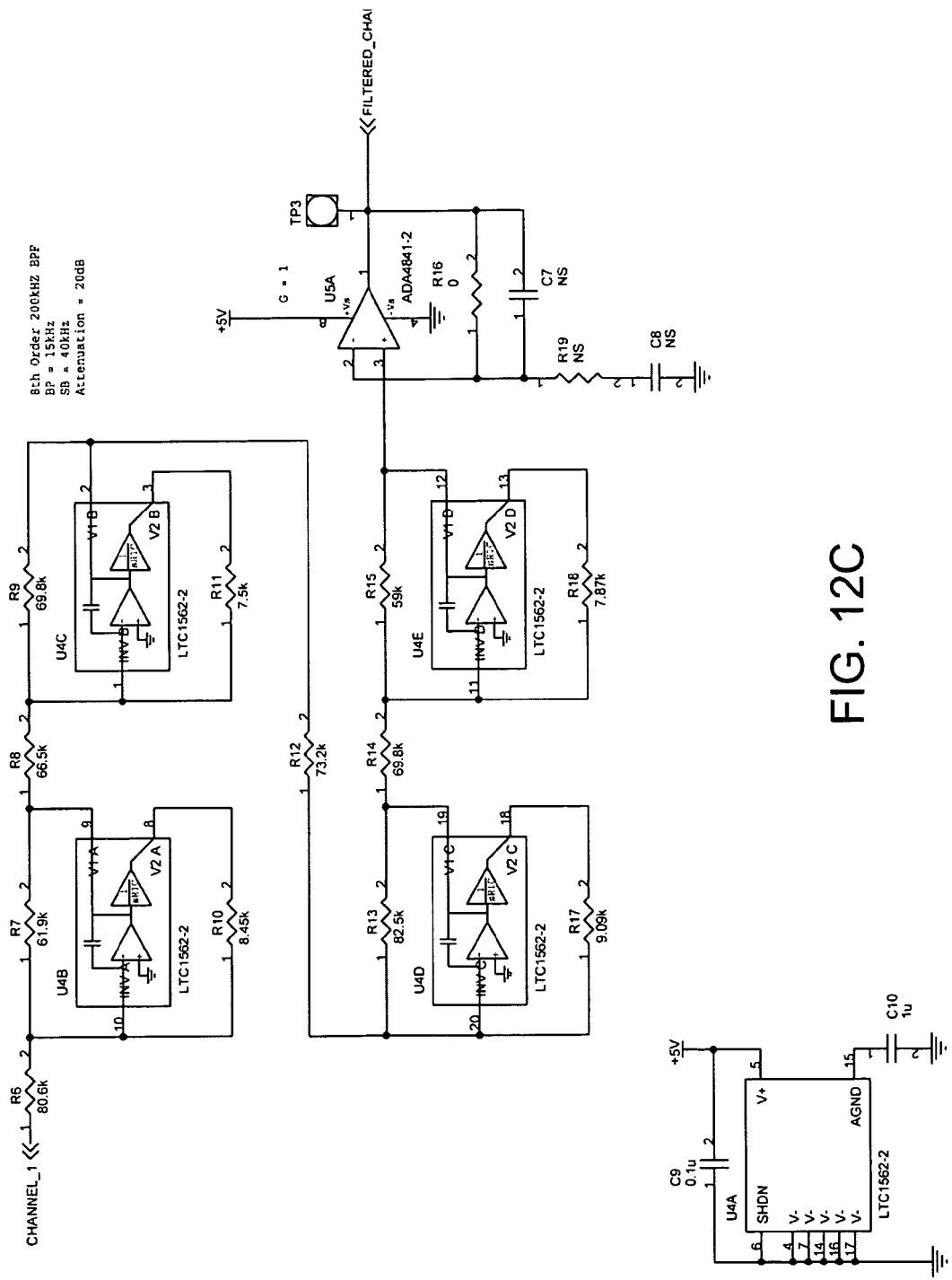
Figure 12D:
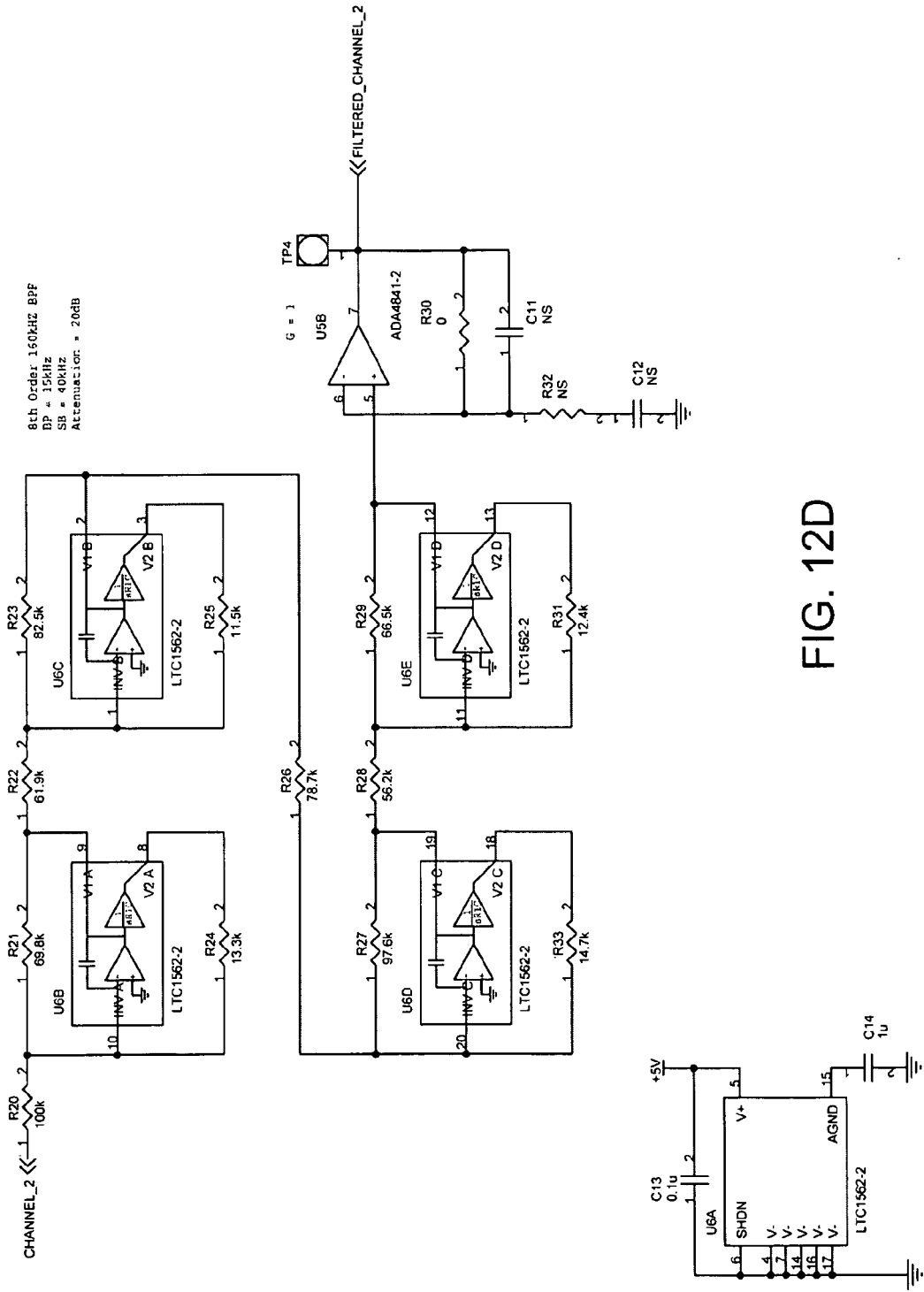
Figure 12E:
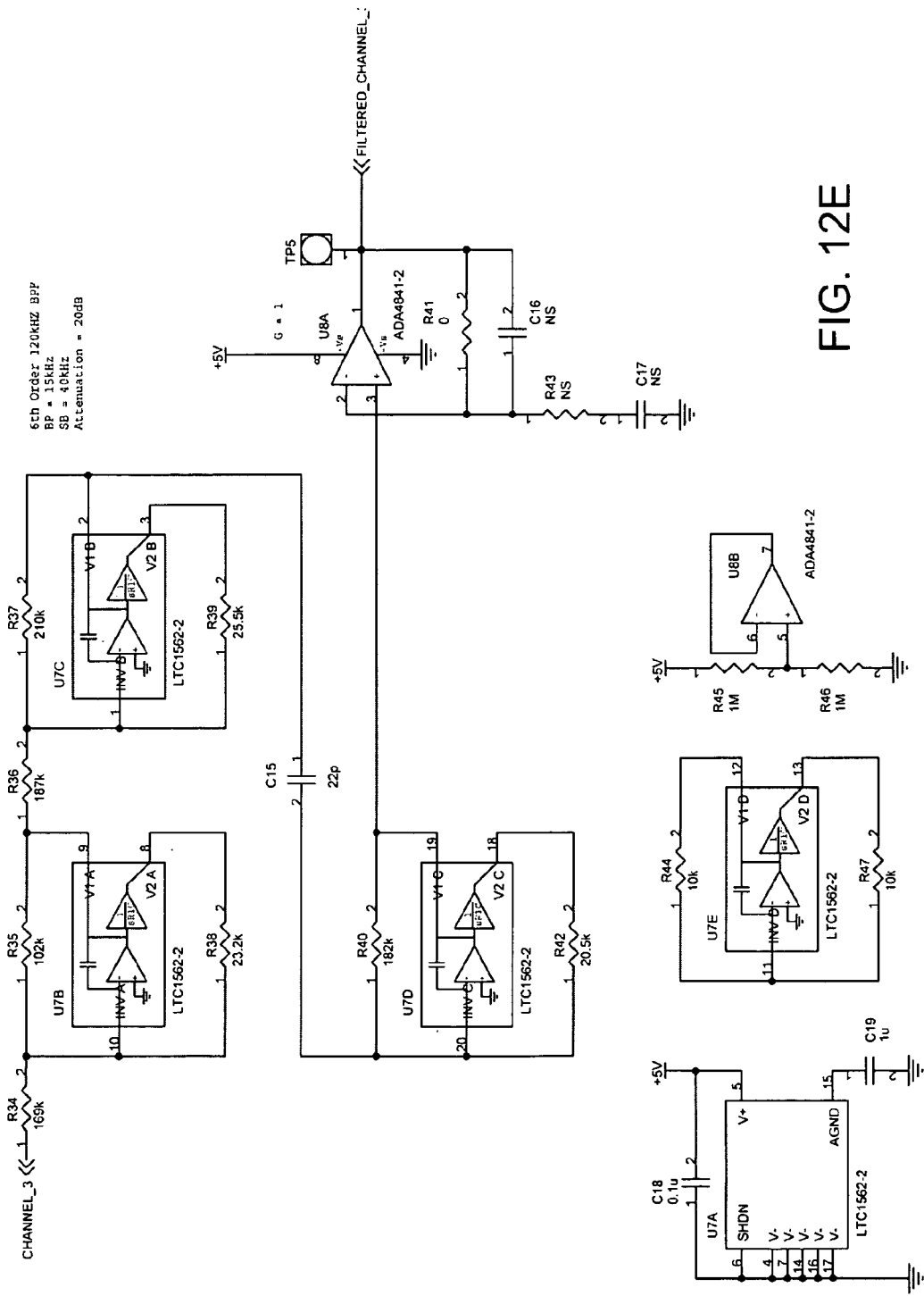

FIGS. 12C-12E are band-pass filters, each with different center frequencies. They are eighth order band-pass filters built around a commercially available part from Linear Technologies. At the output, there is another buffer stage.

Figure 12F:
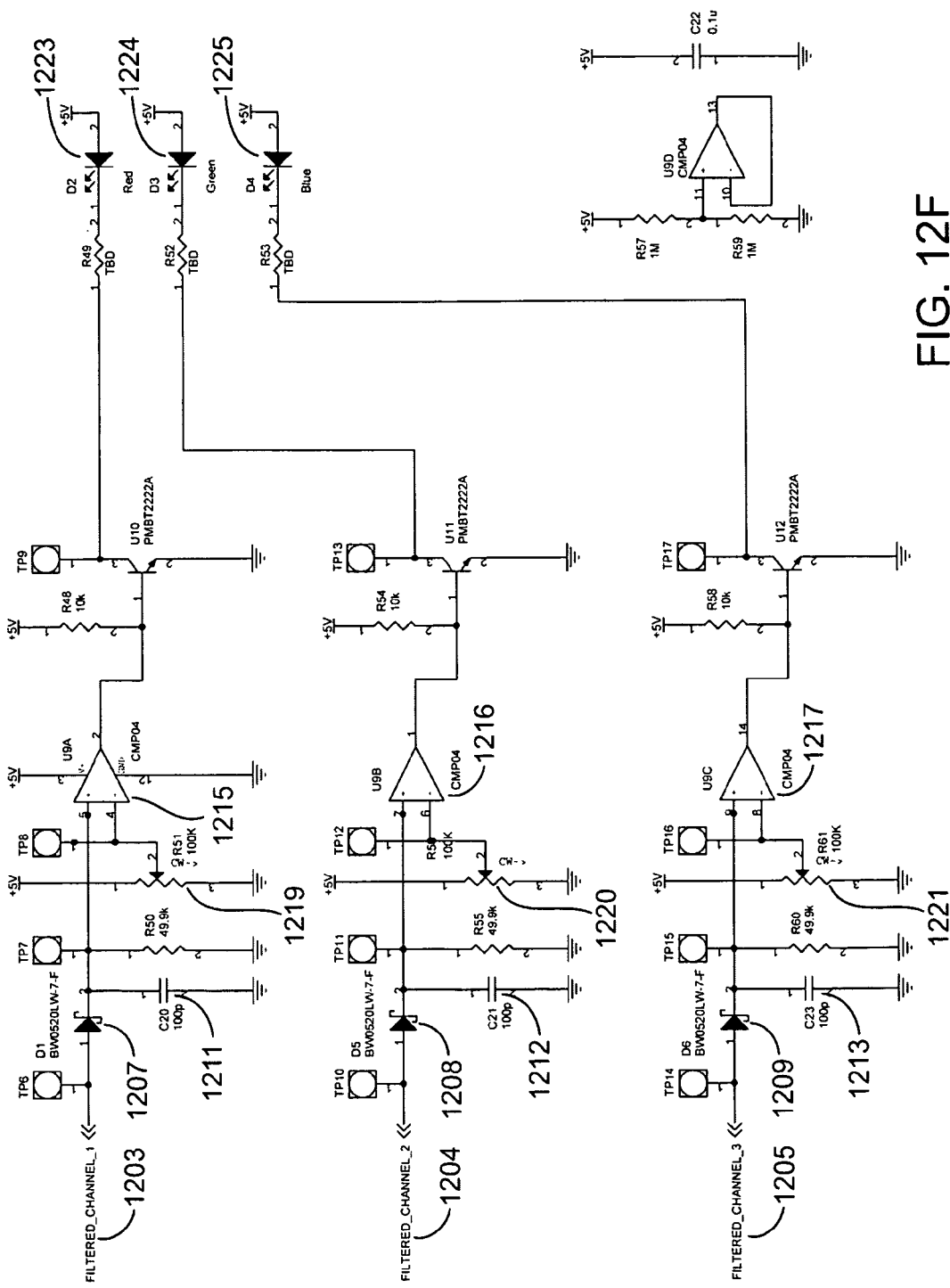

The circuit in FIG. 12F measures the energy level of the received signal at each of the three filter pass-bands. The received signal 1203-1205 at each frequency is rectified through Schottky diodes 1207-1209 and capacitors 1211-1213. The rectified signals go into comparators 1215-1217 which compare the voltage against a reference voltage set by potentiometers 1219-1221. If the voltage is above the threshold, LEDs 1223-1225 light up, with a different color corresponding to a different frequency.

Applications

As indicated above, the systems and methods of the invention find use in a variety of different applications, which applications may be categorized as prospective applications, real-time applications and historical applications.

In certain embodiments of the invention, all medication orders are provided in a HIS. Patients in the hospital wear a patient associated identifier that is continuously updated, e.g., via a wireless link, with their personal updated medication orders. During fluid delivery, an IV pump only delivers medication to the patient after confirmation between the delivery device and patient associated identifier. Alerts may be distributed for situations where confirmation is not obtained. Furthermore, confirmation may be required for drug delivery to occur, and drug deliver may be inhibited in the absence of confirmation.

Kits

Also provided are kits for practicing the subject methods. Kits may include one or more receivers of the invention, as described above. In addition, the kits may include one or more parenteral dosage devices, e.g., preloaded syringes, vials, IV bags, etc. The dosage amount of the one or more pharmacological agents provided in a kit may be sufficient for a single application or for multiple applications. In certain embodiments, the kits may include a smart parenteral delivery system that provides specific identification and detection of parenteral beneficial agents or beneficial agents taken into the body through other methods, for example, through the use of a syringe, inhaler, or other device that administers medicine, such as described above.

The subject kits may also include instructions for how to practice the subject methods using the components of the kit. The instructions may be recorded on a suitable recording medium or substrate. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Some or all components of the subject kits may be packaged in suitable packaging to maintain sterility. In many embodiments of the subject kits, the components of the kit are packaged in a kit containment element to make a single, easily handled unit, where the kit containment element, e.g., box or analogous structure, may or may not be an airtight container, e.g., to further preserve the sterility of some or all of the components of the kit.

It is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

What is claimed is:

1. A system comprising:
an identifier configured to be stably associated with a patient of the system; and
an inhaler configured to:
communicate to the identifier, by using the patient's body as a signal conduction medium, a fluid transfer signal notifying a fluid transfer event of administering fluid contained in the inhaler to the patient;
initiate the fluid transfer event in response to a receipt of a first signal approving the fluid transfer event from the identifier; and
continue or terminate the fluid transfer event in response to a second signal indicating a response of the patient to the fluid transfer event from the identifier.

2. The system of claim 1, wherein the fluid transfer event occurs if a proper match between the patient and the fluid transfer event is detected.

3. The system of claim 2, wherein the fluid comprises medication.

4. The system of claim 3, wherein when the fluid transfer event occurs, the inhaler is configured to detect whether the patient is inhaling or not through detecting air stream generated by the patient.

5. The system of claim 4, wherein the inhaler is configured to transmit a signal encoding a type and amount of the medication inhaled by the patient and delivery time of the medication to a receiver stably associated with the patient.

6. The system of claim 5, wherein an alert is generated to indicate whether the medication has been properly delivered to the patient or not.

7. The system according to claim 1, further comprising an external processing system with a remote receiver, wherein at least one of the inhaler or the identifier is configured to transmit a signal to the remote receiver.

8. The system according to claim 7, wherein the external processing system is a hospital information system or a home health care information system.

9. The system according to claim 1, wherein the identifier is implanted in the patient.

10. The system according to claim 1, wherein the identifier is topically positioned on the patient.

* * * * *